(12) United States Patent
Heye

(10) Patent No.: US 12,239,394 B2
(45) Date of Patent: Mar. 4, 2025

(54) MEDICAL TOOL WITH LENGTH CONSERVATION MECHANISM FOR ACTUATING TENSION BANDS

(71) Applicant: INTUITIVE SURGICAL OPERATIONS, INC., Sunnyvale, CA (US)

(72) Inventor: Isabelle Heye, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 622 days.

(21) Appl. No.: 17/617,645

(22) PCT Filed: Jun. 11, 2020

(86) PCT No.: PCT/US2020/037265
§ 371 (c)(1),
(2) Date: Dec. 9, 2021

(87) PCT Pub. No.: WO2020/252184
PCT Pub. Date: Dec. 17, 2020

(65) Prior Publication Data
US 2023/0329807 A1  Oct. 19, 2023

Related U.S. Application Data

(60) Provisional application No. 62/860,938, filed on Jun. 13, 2019.

(51) Int. Cl.
*A61B 17/00* (2006.01)
*A61B 17/29* (2006.01)
(Continued)

(52) U.S. Cl.
CPC .............. *A61B 34/30* (2016.02); *A61B 17/29* (2013.01); *A61B 2017/00327* (2013.01); *A61B 34/70* (2016.02)

(58) Field of Classification Search
CPC .......... A61B 17/29; A61B 2017/00327; A61B 2017/2902; A61B 2017/2903;
(Continued)

(56) References Cited

U.S. PATENT DOCUMENTS 2,091,317 A  8/1937 Hill
3,365,966 A  1/1968 Don et al.
(Continued)

FOREIGN PATENT DOCUMENTS

AU  2014208189 A1  4/2015
CN  101627894 A  1/2010
(Continued)

OTHER PUBLICATIONS

Extended European Search Report for Application No. EP18887892.0 mailed on Jul. 20, 2021, 7 pages.
(Continued)

*Primary Examiner* — Kelly J Bekker
*Assistant Examiner* — Lindsey R. Rivers

(57) ABSTRACT

An actuation assembly for a medical instrument connects four bands to three motorized degrees of freedom. The actuation assembly includes a first actuator, a second actuator and a third actuator. The first actuator is coupled to a first band and a second band, the first actuator being operable to pull in one of the first and second bands and feed out the other of the first and second bands. The third actuator is coupled to a third band and a fourth band, the third actuator being operable to pull in one of the third and fourth bands and feed out the other of the third and fourth bands. Each of the first, second, third, and fourth bands pass through a second actuator, and the second actuator is operable to increase the travel path of both the first and second bands or both the third and fourth bands.

12 Claims, 32 Drawing Sheets

(51) Int. Cl.
*A61B 34/00* (2016.01)
*A61B 34/30* (2016.01)
*A61B 34/37* (2016.01)

(58) Field of Classification Search
CPC . A61B 2017/2912; A61B 34/30; A61B 34/70; A61B 34/71; A61B 2034/306
See application file for complete search history.

(56) References Cited

U.S. PATENT DOCUMENTS

| | | |
|---|---|---|
| 4,084,594 A | 4/1978 | Mosior |
| 4,319,673 A | 3/1982 | Kojima |
| 4,785,683 A | 11/1988 | Buckley et al. |
| 4,850,241 A | 7/1989 | Buckley et al. |
| 5,207,691 A | 5/1993 | Nardella |
| 5,352,235 A | 10/1994 | Koros et al. |
| 5,531,744 A | 7/1996 | Nardella et al. |
| 5,713,896 A | 2/1998 | Nardella |
| 5,730,740 A | 3/1998 | Wales et al. |
| 5,792,135 A | 8/1998 | Madhani et al. |
| 5,797,938 A | 8/1998 | Paraschac et al. |
| 5,800,449 A | 9/1998 | Wales |
| 5,807,377 A | 9/1998 | Madhani et al. |
| 5,817,128 A | 10/1998 | Storz |
| 5,876,325 A | 3/1999 | Mizuno et al. |
| 6,007,550 A | 12/1999 | Wang et al. |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,817,974 B2 | 11/2004 | Cooper et al. |
| 6,994,708 B2 | 2/2006 | Manzo |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,371,210 B2 | 5/2008 | Brock et al. |
| 7,608,083 B2 | 10/2009 | Lee et al. |
| 7,666,191 B2 | 2/2010 | Orban, III et al. |
| 7,935,130 B2 | 5/2011 | Williams |
| 8,142,421 B2 | 3/2012 | Cooper et al. |
| 8,224,484 B2 | 7/2012 | Swarup et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,597,280 B2 | 12/2013 | Cooper et al. |
| 8,602,288 B2 | 12/2013 | Shelton, IV et al. |
| 8,771,270 B2 | 7/2014 | Burbank |
| 8,800,838 B2 | 8/2014 | Shelton, IV |
| 8,808,166 B2 | 8/2014 | Hosaka |
| 8,911,471 B2 | 12/2014 | Spivey et al. |
| 8,939,963 B2 | 1/2015 | Rogers et al. |
| 8,992,565 B2 | 3/2015 | Brisson et al. |
| 9,028,494 B2 | 5/2015 | Shelton, IV et al. |
| 9,078,684 B2 | 7/2015 | Williams |
| 9,186,221 B2 | 11/2015 | Burbank |
| 9,198,729 B2 | 12/2015 | Rogers |
| 9,204,923 B2 | 12/2015 | Manzo et al. |
| 9,232,979 B2 | 1/2016 | Parihar et al. |
| 9,259,274 B2 | 2/2016 | Prisco |
| 9,259,275 B2 | 2/2016 | Burbank |
| 9,572,616 B2 | 2/2017 | Vaughn |
| 9,664,262 B2 | 5/2017 | Donlon et al. |
| 9,803,727 B2 | 10/2017 | Solomon et al. |
| 9,839,439 B2 | 12/2017 | Cooper et al. |
| 9,913,694 B2 | 3/2018 | Brisson et al. |
| 9,931,106 B2 | 4/2018 | Au et al. |
| 9,962,228 B2 | 5/2018 | Schuh et al. |
| 10,016,244 B2 | 7/2018 | Cooper et al. |
| 10,022,193 B2 | 7/2018 | Cooper et al. |
| 10,130,366 B2 | 11/2018 | Shelton, IV et al. |
| 10,219,874 B2 | 3/2019 | Yu et al. |
| 10,288,837 B2 | 5/2019 | Miyatani et al. |
| 10,299,873 B2 | 5/2019 | Hares et al. |
| 10,314,583 B2 | 6/2019 | Smith et al. |
| 10,357,321 B2 | 7/2019 | Donlon et al. |
| 10,470,830 B2 | 11/2019 | Hill et al. |
| 10,478,256 B2 | 11/2019 | Shelton, IV et al. |
| 10,550,918 B2 | 2/2020 | Cooper et al. |
| 10,595,836 B2 | 3/2020 | Smaby et al. |
| 10,595,948 B2 | 3/2020 | Solomon et al. |
| 10,595,949 B2 | 3/2020 | Donlon et al. |
| 10,624,709 B2 | 4/2020 | Remm |
| 10,682,141 B2 | 6/2020 | Moore et al. |
| 10,799,303 B2 | 10/2020 | Cooper et al. |
| 10,806,530 B2 | 10/2020 | Liao et al. |
| 10,813,706 B2 | 10/2020 | Chaplin et al. |
| 10,881,280 B2 | 1/2021 | Baez, Jr. |
| 10,932,868 B2 | 3/2021 | Solomon et al. |
| 11,013,566 B2 | 5/2021 | Diel et al. |
| 11,020,112 B2 | 6/2021 | Shelton, IV et al. |
| 11,045,270 B2 | 6/2021 | Shelton, IV et al. |
| 11,129,686 B2 | 9/2021 | Chaplin et al. |
| 11,207,145 B2 | 12/2021 | Lambrecht et al. |
| 11,241,290 B2 | 2/2022 | Waterbury et al. |
| 11,248,686 B2 | 2/2022 | Cooper et al. |
| 11,304,770 B2 | 4/2022 | Crews et al. |
| 11,517,397 B2 | 12/2022 | Lambrecht et al. |
| 2002/0111635 A1 | 8/2002 | Jensen et al. |
| 2006/0190034 A1 | 8/2006 | Nishizawa et al. |
| 2006/0217742 A1 | 9/2006 | Messerly et al. |
| 2006/0276775 A1 | 12/2006 | Rosenberg et al. |
| 2007/0043338 A1 | 2/2007 | Moll et al. |
| 2007/0119274 A1 | 5/2007 | Devengenzo et al. |
| 2007/0137371 A1 | 6/2007 | Devengenzo et al. |
| 2007/0232858 A1 | 10/2007 | Macnamara et al. |
| 2008/0009838 A1 | 1/2008 | Schena et al. |
| 2008/0015566 A1 | 1/2008 | Livneh |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0088774 A1 | 4/2009 | Swarup et al. |
| 2009/0198272 A1 | 8/2009 | Kerver et al. |
| 2009/0222022 A1 | 9/2009 | Laporte et al. |
| 2010/0011900 A1 | 1/2010 | Burbank et al. |
| 2010/0175701 A1 | 7/2010 | Reis et al. |
| 2010/0198253 A1 | 8/2010 | Jinno et al. |
| 2010/0318101 A1 | 12/2010 | Choi et al. |
| 2011/0015650 A1 | 1/2011 | Choi et al. |
| 2011/0065992 A1 | 3/2011 | Bissinger |
| 2011/0071543 A1 | 3/2011 | Prisco et al. |
| 2011/0118754 A1 | 5/2011 | Dachs, II et al. |
| 2011/0184241 A1 | 7/2011 | Zubiate et al. |
| 2011/0251612 A1 | 10/2011 | Faller et al. |
| 2011/0277580 A1 | 11/2011 | Cooper et al. |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0046522 A1 | 2/2012 | Naito |
| 2012/0123441 A1 | 5/2012 | Au et al. |
| 2012/0150192 A1 | 6/2012 | Dachs, II et al. |
| 2012/0289974 A1 | 11/2012 | Rogers et al. |
| 2012/0292367 A1 | 11/2012 | Morgan et al. |
| 2012/0298719 A1 | 11/2012 | Shelton, IV et al. |
| 2012/0330287 A1* | 12/2012 | Yim ............... A61B 34/71 606/1 |
| 2013/0046318 A1 | 2/2013 | Radgowski et al. |
| 2013/0079810 A1 | 3/2013 | Isenberg |
| 2013/0144395 A1 | 6/2013 | Stefanchik et al. |
| 2013/0239735 A1 | 9/2013 | Solomon et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0114327 A1 | 4/2014 | Boudreaux et al. |
| 2014/0128849 A1* | 5/2014 | Au ............... A61B 17/00 606/1 |
| 2014/0257333 A1 | 9/2014 | Blumenkranz |
| 2014/0309625 A1 | 10/2014 | Okamoto et al. |
| 2015/0005786 A1 | 1/2015 | Burbank |
| 2015/0150635 A1 | 6/2015 | Kilroy et al. |
| 2015/0150636 A1 | 6/2015 | Hagn et al. |

(56) References Cited

U.S. PATENT DOCUMENTS

| | | |
|---|---|---|
| 2015/0157355 A1 | 6/2015 | Price et al. |
| 2016/0045770 A1 | 2/2016 | Yamada |
| 2016/0157926 A1 | 6/2016 | Boudreaux |
| 2016/0184034 A1 | 6/2016 | Holop et al. |
| 2016/0199138 A1 | 7/2016 | Cooper et al. |
| 2016/0296219 A1 | 10/2016 | Srivastava et al. |
| 2016/0302819 A1 | 10/2016 | Stulen et al. |
| 2016/0338762 A1 | 11/2016 | Krastins et al. |
| 2016/0361049 A1 | 12/2016 | Dachs, II et al. |
| 2016/0361107 A1 | 12/2016 | Zergiebel et al. |
| 2017/0007345 A1 | 1/2017 | Smith et al. |
| 2017/0165017 A1 | 6/2017 | Chaplin et al. |
| 2017/0172672 A1 | 6/2017 | Bailey et al. |
| 2017/0234411 A1 | 8/2017 | Dewaele et al. |
| 2018/0080533 A1 | 3/2018 | Awtar |
| 2018/0126504 A1 | 5/2018 | Shelton, IV et al. |
| 2018/0214223 A1 | 8/2018 | Turner |
| 2018/0333164 A1 | 11/2018 | Arata et al. |
| 2019/0038282 A1 | 2/2019 | Shelton, IV et al. |
| 2019/0117325 A1 | 4/2019 | Kishi |
| 2019/0125468 A1 | 5/2019 | Adams |
| 2019/0159846 A1 | 5/2019 | Yates et al. |
| 2019/0223960 A1 | 7/2019 | Chaplin et al. |
| 2019/0231464 A1 | 8/2019 | Wixey et al. |
| 2019/0298323 A1 | 10/2019 | Lambrecht et al. |
| 2019/0307522 A1 | 10/2019 | Lambrecht et al. |
| 2019/0328467 A1 | 10/2019 | Waterbury et al. |
| 2019/0380800 A1 | 12/2019 | Jogasaki et al. |
| 2020/0093554 A1 | 3/2020 | Schuh et al. |
| 2020/0138473 A1 | 5/2020 | Shelton, IV et al. |
| 2020/0197117 A1 | 6/2020 | Donlon et al. |
| 2020/0383738 A1 | 12/2020 | Abbott et al. |
| 2020/0383739 A1 | 12/2020 | Abbott et al. |
| 2021/0045819 A1 | 2/2021 | Castillo et al. |
| 2021/0169597 A1 | 6/2021 | Abbott et al. |
| 2021/0372508 A1 | 12/2021 | Abbott |
| 2022/0000572 A1 | 1/2022 | Ragosta et al. |
| 2022/0039895 A1 | 2/2022 | Adams et al. |
| 2022/0192764 A1 | 6/2022 | Waterbury et al. |
| 2023/0079266 A1 | 3/2023 | Wixey et al. |
| 2023/0119001 A1 | 4/2023 | Abbott |
| 2023/0119775 A1 | 4/2023 | Lambrecht et al. |
| 2023/0279931 A1 | 9/2023 | Cooper et al. |
| 2023/0355328 A1 | 11/2023 | Lambrecht et al. |
| 2024/0090972 A1 | 3/2024 | Lambrecht et al. |
| 2024/0156551 A1 | 5/2024 | Lambrecht et al. |
| 2024/0197423 A1 | 6/2024 | Ragosta et al. |

FOREIGN PATENT DOCUMENTS

| | | |
|---|---|---|
| CN | 101893060 A | 11/2010 |
| CN | 104116547 A | 10/2014 |
| CN | 104799891 A | 7/2015 |
| CN | 109505951 A | 3/2019 |
| DE | 102016112546 A1 | 3/2017 |
| EP | 2362285 A2 | 8/2011 |
| EP | 2415418 A1 | 2/2012 |
| EP | 2548529 A1 | 1/2013 |
| EP | 2783643 A1 | 10/2014 |
| EP | 3103374 A1 | 12/2016 |
| EP | 3195993 A1 | 7/2017 |
| FR | 3014678 A1 | 6/2015 |
| JP | H06114000 A | 4/1994 |
| JP | H10249777 A | 9/1998 |
| JP | 2002200091 A | 7/2002 |
| JP | 2004301275 A | 10/2004 |
| JP | 2005288590 A | 10/2005 |
| JP | 2014534080 A | 12/2014 |
| WO | WO-9729690 A1 | 8/1997 |
| WO | WO-0030557 A1 | 6/2000 |
| WO | WO-2010009224 A1 | 1/2010 |
| WO | WO-2010081050 A1 | 7/2010 |
| WO | WO-2011060046 A2 | 5/2011 |
| WO | WO-2012068156 A2 | 5/2012 |
| WO | WO-2015142290 A1 | 9/2015 |
| WO | WO-2016172299 A1 | 10/2016 |
| WO | WO-2016189284 A1 | 12/2016 |
| WO | WO-2017064303 A1 | 4/2017 |
| WO | WO-2017188851 A1 | 11/2017 |
| WO | WO-2018013313 A1 | 1/2018 |
| WO | WO-2018049217 A1 | 3/2018 |
| WO | WO-2018069679 A1 | 4/2018 |
| WO | WO-2018094191 A1 | 5/2018 |
| WO | WO-2018123024 A1 | 7/2018 |
| WO | WO-2018179140 A1 | 10/2018 |
| WO | WO-2020102776 A1 | 5/2020 |
| WO | WO-2020102780 A1 | 5/2020 |
| WO | WO-2021155707 A1 | 8/2021 |
| WO | WO-2023055684 A2 | 4/2023 |
| WO | WO-2023177554 A1 | 9/2023 |

OTHER PUBLICATIONS

Extended European Search Report for Application No. EP18889541.1 mailed on Sep. 14, 2021, 7 pages.

Extended European Search Report for Application No. EP20180889370.5 mailed on Aug. 24, 2021, 7 pages.

International Search Report and Written Opinion for Application No. PCT/US2020/037265, mailed Sep. 4, 2020, 12 pages.

International Search Report and Written Opinion for Application No. PCT/US2018/064725, mailed on Mar. 28, 2019, 9 pages.

Office Action for JP Application No. 2020-532549, mailed Jul. 13, 2021, 16 pages.

Office Action for JP Application No. 2020-532669, mailed Jul. 20, 2021, 14 pages.

Office Action for JP Application No. 2020-532725, mailed Jul. 13, 2021, 15 pages.

Office Action for U.S. Appl. No. 16/769,116, mailed Oct. 5, 2021, 33 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action mailed May 15, 2024 for U.S. Appl. No. 18/376,726, filed Oct. 4, 2023, 10 pages.

Office Action for EP Application No. EP20751736.8, mailed Jul. 5, 2024, 07 Pages.

* cited by examiner

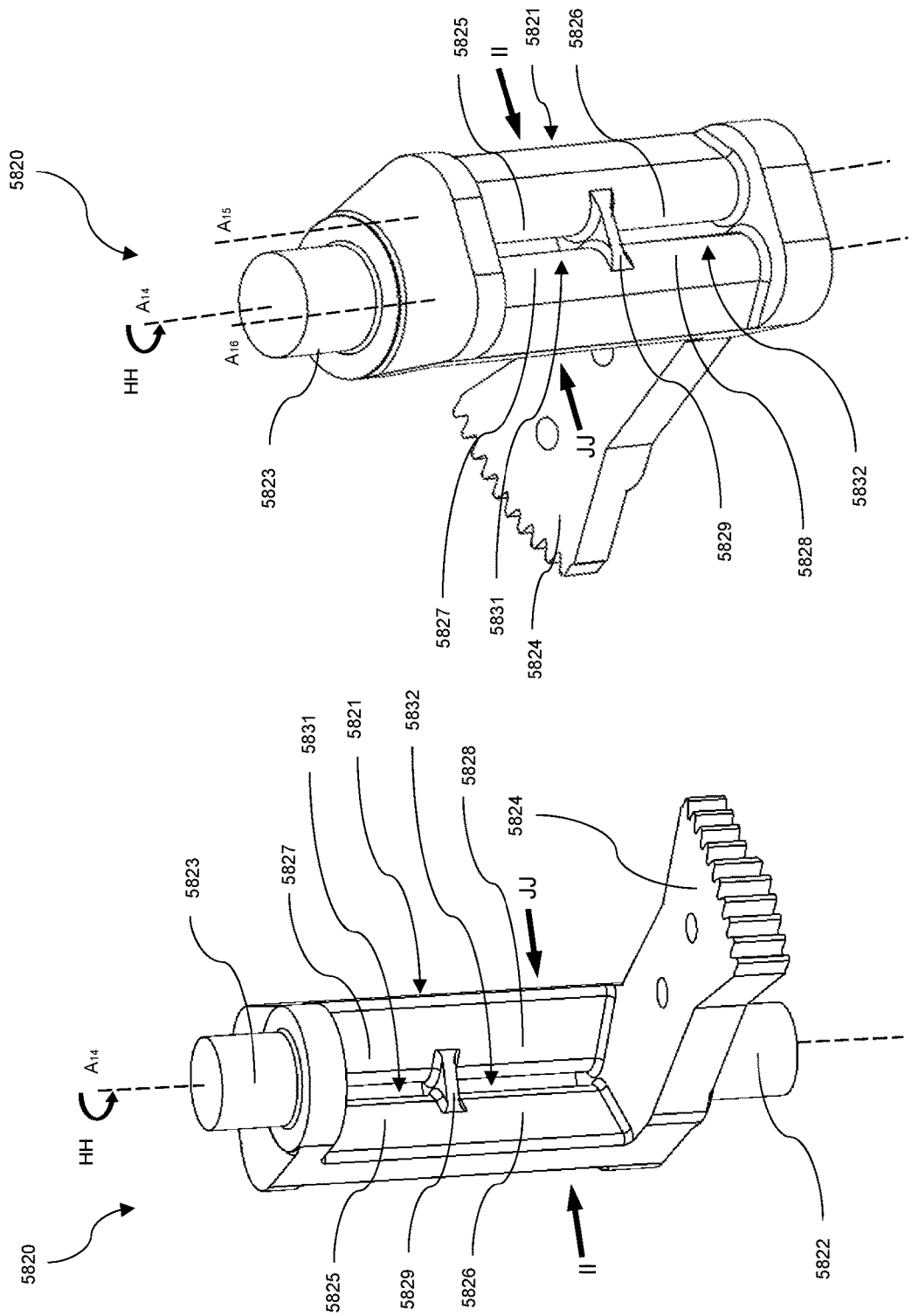

MEDICAL TOOL WITH LENGTH CONSERVATION MECHANISM FOR ACTUATING TENSION BANDS

RELATED APPLICATION

This application is a U.S. national stage filing under 35 U.S.C. § 371 of International Application No. PCT/US2020/037265 (filed Jun. 11, 2020), entitled "MEDICAL TOOL WITH LENGTH CONSERVATION MECHANISM FOR ACTUATING TENSION BANDS," which claims priority to and the filing date benefit of U.S. Provisional Patent Application No. 62/860,938 (filed Jun. 13, 2019), entitled "MEDICAL TOOL WITH LENGTH CONSERVATION MECHANISM FOR ACTUATING TENSION BANDS," each of which is incorporated herein by reference in its entirety.

BACKGROUND

The embodiments described herein relate to grasping tools, more specifically to medical devices, and still more specifically to endoscopic tools. More particularly, the embodiments described herein relate to devices that include tension bands and a mechanism for conserving the length of the bands during a range of motion of a wrist joint.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of a shaft. During an MIS procedure, the end effector, wrist mechanism, and the distal end of the shaft can be inserted into a small incision or a natural orifice of a patient to position the end effector at a work site within the patient's body. The optional wrist mechanism can be used to change the end effector's orientation with respect to the shaft to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension elements (e.g., cables) that extend through the shaft of the instrument and that connect the wrist mechanism to an actuator (also referred to herein as a backend mechanism). The actuator moves the cables to operate the wrist mechanism. For robotic or teleoperated systems, the backend mechanism is motor driven and can be operably coupled to a processing system to provide a user interface for a clinical user (e.g., a surgeon) to control the instrument.

Patients benefit from continual efforts to improve the effectiveness of MIS methods and tools. For example, reducing the size and/or the operating footprint of the shaft and wrist mechanism can allow for smaller entry incisions and reduced need for space at the surgical site, thereby reducing the negative effects of surgery, such as pain, scarring, and undesirable healing time. But, producing small medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Further, the wrist mechanism generally provides specific degrees of freedom for movement of the end effector. For example, for forceps or other grasping tools, the wrist may be able to change the pitch, yaw, and grip of the end effector. More degrees of freedom could be implemented through the wrist, but would require additional actuation members in the wrist and shaft, which competes for the limited space that exists given the size restrictions required by MIS applications. Other degrees of freedom, such as roll or insertion/extraction through movement of the main tube also competes for space at or in the shaft of the device.

A conventional architecture for a wrist mechanism in a robotically controlled medical instrument uses cables to turn a capstan in the wrist mechanism and thereby rotate the portion of the wrist mechanism that is connected to the capstan. For example, a wrist mechanism can include three capstans for rotations about a pitch axis, a yaw axis, or a grip axis. Each capstan can be controlled using two cables that are attached to the capstan so that one side pays out cable while the other side pulls in an equal length of cable. With this architecture, three degrees of freedom call for a total of six cables extending from the wrist mechanism back along the length of the main tube to the backend mechanism of the instrument. Efficient implementation of a wrist mechanism can be complicated because the cables must be carefully routed through the wrist mechanism to maintain stability of the wrist throughout the range of motion of the wrist mechanism and to minimize the interactions (or coupling effects) of one rotation axis upon another. Further, pulleys are generally needed to reduce cable friction, which extends instrument life and permits operation without excessive forces being applied to the cables or other structures in the wrist mechanism.

Thus, a need exists for improved endoscopic tools, including improved backend mechanisms to enable a wrist to be operated with a small number of tension elements, to facilitate miniaturization of the instrument and reduce costs of the instrument, and to reduce manufacturing cost by reducing the number of parts required.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a medical device includes a shaft of a medical instrument, an end effector, a housing, a first actuator, a second actuator, a first band, and a second band. The shaft of the medical instrument includes a proximal end and a distal end, and the end effector is coupled to the distal end of the shaft. The housing is coupled to the proximal end of the shaft. The first actuator and the second actuator are rotatably supported in the housing. The first band has a first end portion and a second end portion, the first end portion of the first band is coupled to the first actuator, and the second end portion of the first band is coupled to the end effector. The second band has a first end portion and a second end portion, the first end portion is coupled to the first actuator, and the second end portion is coupled to the end effector. The first actuator is configured to move the first band in a first direction and the second band in a second direction, opposite to the first direction, to actuate the end effector in a first degree of freedom. The second actuator includes a first guide structure, which has a first guide surface and a second guide surface. The first guide surface is in contact with the first end portion of the first band, the second guide surface is in contact with the first end portion of the second band, and movement of the second actuator actuates both the first band and the second band in the first direction to actuate the end effector in a second degree of freedom.

In some embodiments, the medical device further includes a third actuator, a fourth actuator, a third band, a fourth band, and the end effectors include a first jaw member and a second jaw member. The second end portions of the first and second bands are coupled to the first jaw member. The first end portions of the third and fourth bands are coupled to the third actuator, and the second end portions of the third and fourth bands are coupled to the second jaw member. Movement of the third actuator actuates the third band in the first direction and the fourth band in the second direction to actuate the second jaw of the end effector. The fourth actuator includes a second guide structure, which has a third guide surface and a fourth guide surface. The third guide surface is in contact with the first end portion of the third band and the fourth guide surface is in contact with the first end portion of the fourth band. Movement of the fourth actuator actuates both the third band and the fourth bands in the second direction to actuate the end effector in a second degree of freedom.

In some embodiments, the first and second guide surfaces each have a curved surface monolithically constructed with the second actuator. The first and second guide surfaces are curved about a first guide structure axis of the second actuator. The first guide surface has a first width extending along the first guide structure axis, and the second guide surface has a second width extending along the first guide structure axis which is spaced apart from the first guide surface along the first guide structure axis. When the first actuator moves the first and second bands, the first end portion of the first band slides along the first guide surface and the first end portion of the second band slides along the second guide surface. The third and fourth guide surfaces are curved about a second guide structure axis of the second actuator. The third guide surface has a third width extending along the second guide structure axis, and the fourth guide surface has a fourth width extending along the second guide structure axis which is spaced apart from the fourth guide surface along the second guide structure axis. When the third actuator moves the third and fourth bands, the first end portion of the third band slides along the third guide surface and the first end portion of the fourth band slides along the fourth guide surface.

In some embodiments, the second actuator includes a bridge portion. The bridge portion extends from a first location between the first guide surface and the second guide surface to a second location between the third guide surface and the fourth guide surface. In some embodiments, the second actuator includes a base portion with a rotational axis. The first guide surface is a first width of the second actuator parallel to the rotational axis, the second guide surface is a second width of the second actuator parallel to the rotational axis, the third guide surface is a third width of the second actuator parallel to the rotational axis, and the fourth guide surface is a fourth width of the second actuator parallel to the rotation axis. In this manner, the first width, the second width, the third width, and the fourth width are each spaced apart from one other relative to the rotational axis. In some embodiments, the medical device includes a drive gear rotatably supported in the housing and the second actuator includes a sector gear operable to transfer motion from the drive gear to the second actuator.

In some embodiments, the shaft of the medical instrument defines a lumen extending along a central axis of the shaft from the proximal end to the distal end of the shaft. The medical device includes a guide member coupled to the housing and the guide member includes a first guide groove and a second guide groove. At least a portion of the guide member extends over the lumen at the proximal end of the shaft. A central portion of the first band is routed within the first guide groove and into the lumen, and a central portion of the second band is routed within the second guide groove and into the lumen. The first guide groove is located at a first distance away from the central axis of the shaft and the second guide groove is located at a second distance away from the central axis. The first distance is different from the second distance. In some embodiments, the first actuator includes a hook portion, and the first end portion of the first band is coupled to the first actuator via the hook portion. In some embodiments, simultaneous movement of both the first actuator and the third actuator actuates the end effector in a third degree of motion. During this simultaneous movement, the first actuator moves the first band in the first direction and the second band in the second direction. The third actuator moves the third band in the first direction and the second band in the second direction.

In some embodiments, a medical device includes a shaft of a medical instrument, an end effector, a housing, a first actuator, a second actuator, a first band, a second band, and a guide member. The shaft of the medical instrument includes a proximal end and a distal end, and the shaft defines a lumen extending along a central axis of the shaft from the proximal end to the distal end. The end effector is coupled to the distal end of the shaft and the housing is coupled to the proximal end of the shaft. The first actuator and the second actuator are rotatably supported in the housing. The first band has a first end portion and a second end portion, the first end portion of the first band being coupled to the first actuator, and the second end portion being coupled to the end effector. The second band has a first end portion and a second end portion. The first end portion of the second band is coupled to the first actuator and the second end portion of the second band is coupled to the end effector. The guide member is coupled to the housing and at least a portion of the guide member extends over the lumen at the proximal end of the shaft. The guide member includes a first guide element and a second guide element. A central portion of the first band is routed over the first guide element and into the lumen, and a central portion of the second band is routed over the second guide element and into the lumen. The first guide element is at a first offset distance from the proximal end of the shaft along the central axis, the second guide element is at a second offset distance from the proximal end of the shaft along the central axis, and the first offset distance is different from the axial second distance. The first actuator is configured to move the first band in a first direction and the second band in a second direction, opposite to the first direction, to actuate the end effector in a first degree of freedom. The second actuator is configured to move the first band and the second band in the first direction to actuate the end effector in a second degree of freedom.

In some embodiments, the first guide element includes a first rod and a first bearing rotatable about the first rod when the first band moves. The second guide element includes a second rod and a second bearing rotatable about the second rod when the second band moves. The first and second bearings are operable to rotate in opposite directions when the first actuator moves the first band in the first direction and the second band in the second direction. The first and second bearings are operable to rotate in the same direction when the second actuator moves the first band and the second band in the first direction. In some embodiments, the central portions of the first and second bands exit the guide member and enters the lumen of the shaft at about 90 degrees. In some embodiments, the first guide element is perpendicularly offset from the central axis by a first offset distance. The second guide element is perpendicularly offset from the central axis by a second offset distance, with the first distance being different from the second distance.

In some embodiments, the medical device further includes a third actuator, a third band, a fourth band, and the end effector includes a first jaw member and a second jaw member. The second end portions of the first and second bands are coupled to the first jaw member. The first end portions of the third and fourth bands are coupled to the third actuator, and the second end portions of the third and fourth bands are coupled to the second jaw member. Movement of the third actuator actuates the third band in the first direction and the fourth band in the second direction to actuate the second jaw of the end effector.

In some embodiments, the guide member includes a third guide element and a fourth guide element. A central portion of the third band is routed over the third guide element and into the lumen of the shaft. A central portion of the fourth band is routed over the fourth guide element and into the lumen. The third guide element is perpendicularly offset from the central axis by a third offset distance, and the fourth guide element is perpendicularly offset from the central axis by a fourth offset distance, the third offset distance being different from the fourth offset distance.

In some embodiments, a medical device includes a shaft of a medical instrument, an end effector, a housing, a first actuator, a second actuator, a first band, and a guide member. The shaft includes a proximal end and a distal end and defines a lumen extending along a central axis of the shaft from the proximal end to the distal end. The end effector is coupled to the distal end of the shaft and the housing is coupled to the proximal end of the shaft. The first actuator and the second actuator are rotatably supported in the housing. The first band has a first end portion and a second end portion, the first end portion being coupled to the first actuator, and the second end portion being coupled to the end effector. The second band has a first end portion and a second end portion, the first end portion being coupled to the first actuator, and the second end portion being coupled to the end effector. The guide member is coupled to the housing and at least a portion of the guide member extends over the lumen at the proximal end of the shaft. A central portion of the first band is routed through the guide member and into the lumen of the shaft, and the first band is twisted along a longitudinal center line of the first band between the first end portion of the first band and the central portion of the first band. A central portion of the second band is routed through the guide member and into the lumen of the shaft, the second band is twisted along a longitudinal center line of the second band between the first end portion of the second band and the central portion of the second band. The first actuator is configured to move the first band in a first direction and the second band in a second direction, opposite to the first direction, to actuate the end effector in a first degree of freedom. The second actuator is configured to move the first band and the second band in the first direction to actuate the end effector in a second degree of freedom.

In some embodiments, the medical device further includes a third actuator, a third band, a fourth band, and the end effectors include a first jaw member and a second jaw member. The second end portions of the first and second bands are coupled to the first jaw member. The first end portions of the third and fourth bands are coupled to the third actuator, and the second end portions of the third and fourth bands are coupled to the second jaw member. Movement of the third actuator actuates the third band in the first direction and the fourth band in the second direction to actuate the second jaw of the end effector. A central portion of the third and fourth bands are routed through the guide member and into the lumen of the shaft. The third band is twisted along a longitudinal center line of the third band between the first end portion and the central portion of the third band. The fourth band is twisted along a longitudinal center line of the fourth band between the first end portion and the central portion of the fourth band. In some embodiments, the first band is twisted through a twist angle of about 90 degrees. In some embodiments, the first band is twisted through a first direction of rotation, and the second band is also twisted in the first direction. In some embodiments, the first band is twisted through a first direction of rotation, and the second band is twisted through a second direction of rotation which is different from the first direction. In some embodiments, the first band is twisted through a first direction of rotation, and the third band is also twisted in the first direction In some embodiments, the first band is twisted through a first direction of rotation, and the third band is twisted through a second direction of rotation which is different from the first direction. In some embodiment, the first band is twisted through a first direction of rotation, the second band is twisted through the first direction of rotation, the third band is twisted through a second direction of rotation, the fourth band is twisted through the second direction of rotation, and the first direction of rotation is different from the second direction of rotation. In some embodiment, the first band is twisted through a first direction of rotation, the second band is twisted through the first direction of rotation, the third band is twisted through a first direction of rotation, the fourth band is twisted through a first direction of rotation, Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIGS. 21 and 22 are a front perspective view (FIG. 21) and a rear perspective view (FIG. 22) of a second actuator of the actuator assembly in FIG. 20.

DETAILED DESCRIPTION

Figure 1:
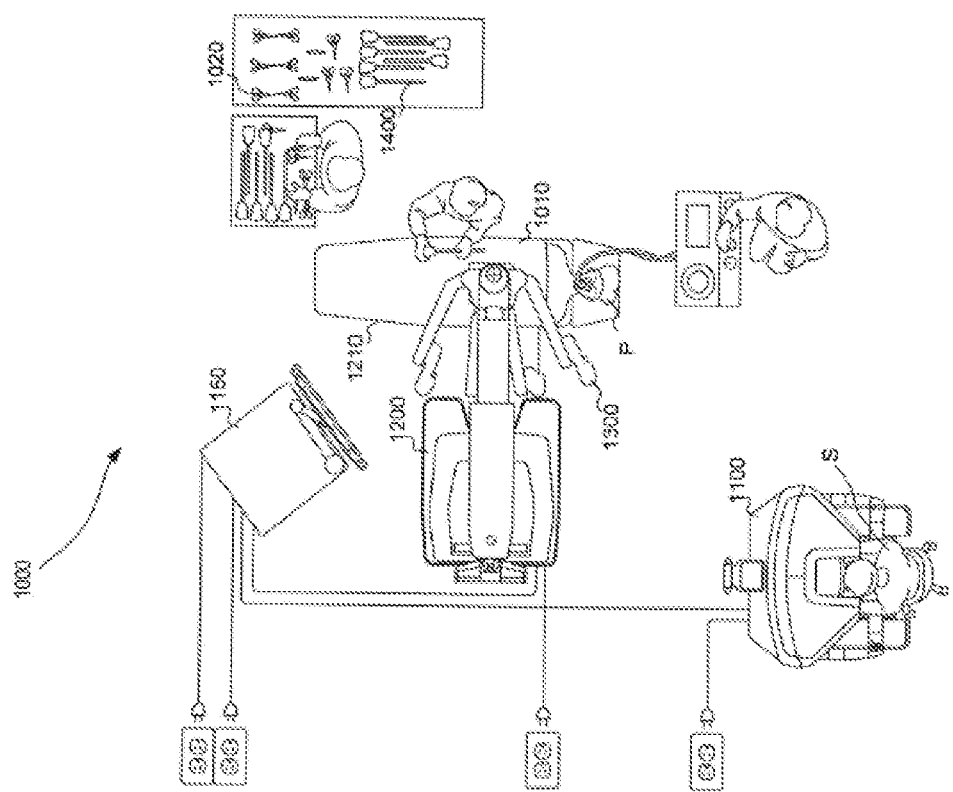
FIG. 1 is a plan view of a minimally invasive teleoperated medical system according to an embodiment being used to perform a medical procedure such as surgery.

The embodiments described herein can advantageously be used in a wide variety of grasping, cutting, and manipulating operations associated with minimally invasive surgery.

The length conservation mechanism of the present application enables motion in three degrees of freedom (e.g., about a pitch axis, a yaw axis, and a grip axis) using only four tension elements, thereby reducing the total number of tension elements required, reducing the space required within the shaft and wrist, reducing overall cost, and enables further miniaturization of the wrist and shaft assemblies to promote MIS procedures. Moreover, the instruments described herein include one or more tension bands that can be moved to actuate the end effector with multiple degrees of freedom. The bands can include regions having a larger cross-sectional area to promote increased strength, or can be twisted to allow efficient routing within the transmission of the instrument.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled instruments 1400 (also referred to herein as a "tool") through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
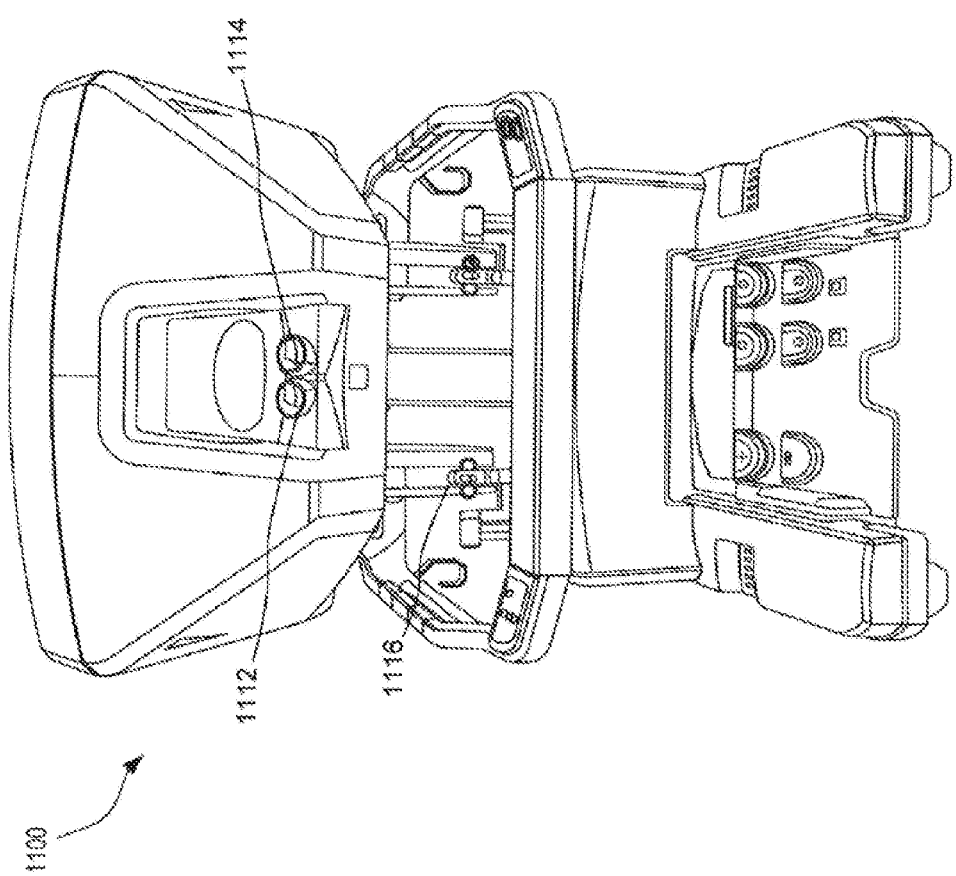
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
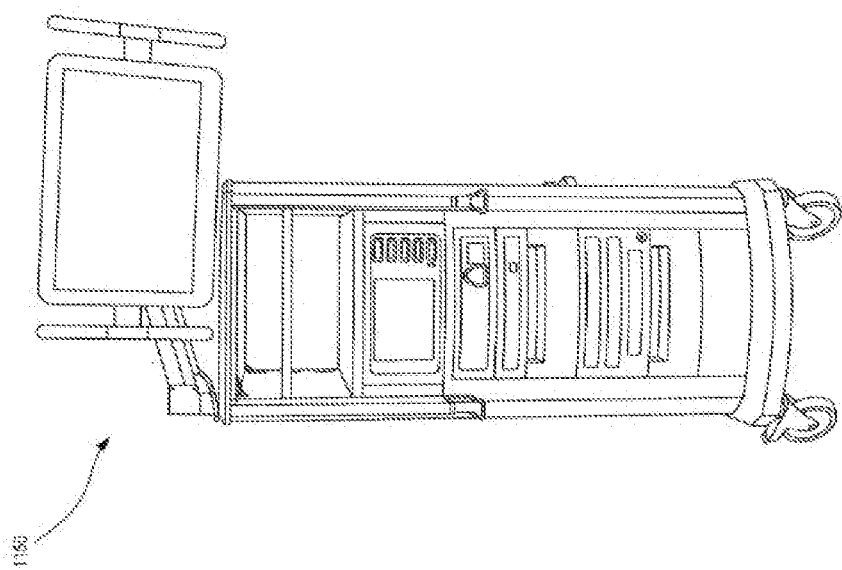
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
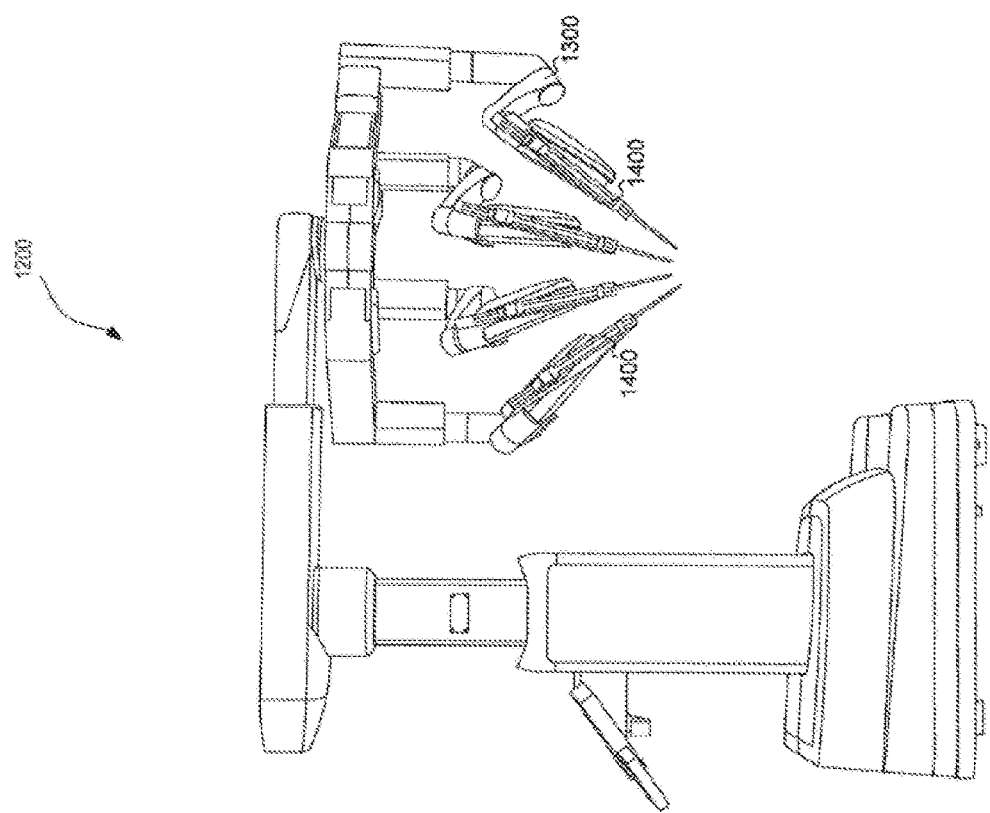
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a software and/or kinematic remote center of motion is maintained at the incision or orifice. In this manner, the incision size can be minimized.

Figure 5:
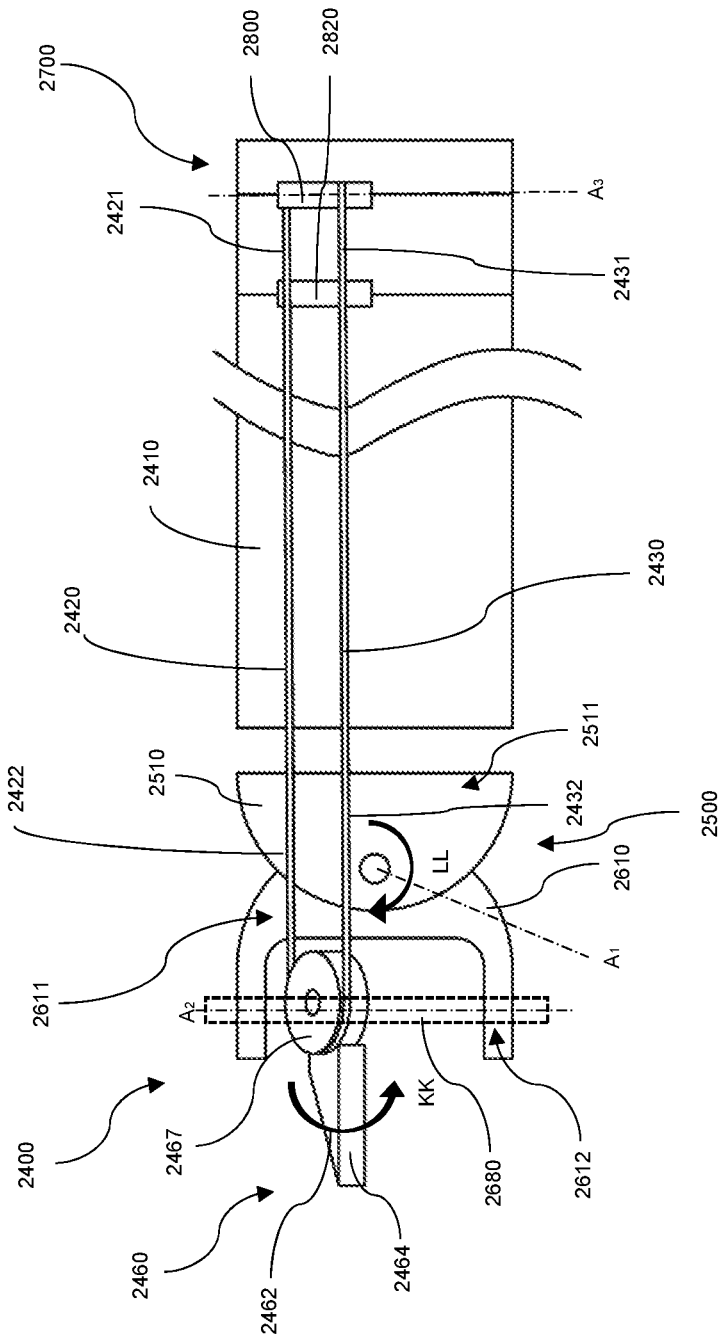
FIG. 5 is a diagrammatic illustration of a portion of an instrument including a first set of bands and two actuators, according to an embodiment.
Figure 6:
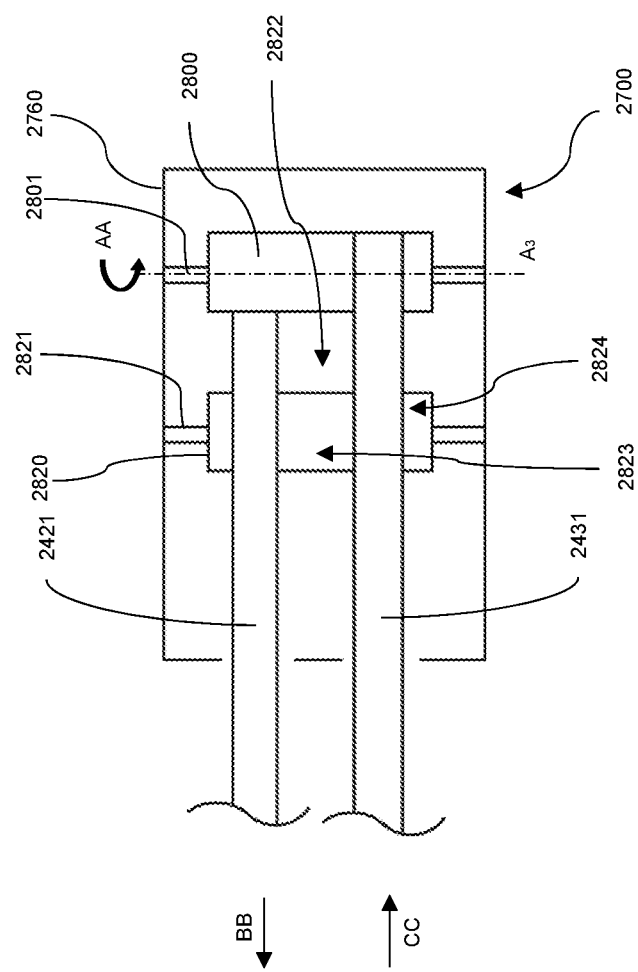
FIG. 6 is an enlarged diagrammatic illustration of the actuator assembly of the portion of the instrument of FIG. 5 depicting an operating state of the first actuator.
Figure 7:
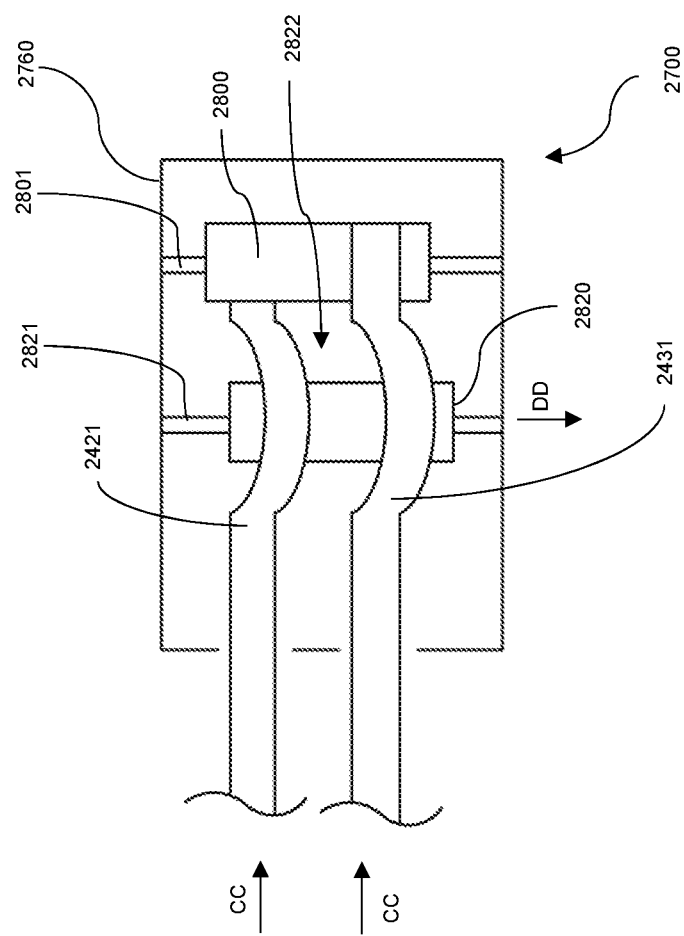
FIG. 7 is an enlarged diagrammatic illustration of the actuator assembly of the portion of the instrument of FIG. 5 depicting an operating state of the second actuator.

FIGS. 5-7 are diagrammatic illustrations of a portion of an instrument 2400, according to an embodiment. The instrument 2400 includes a wrist assembly 2500, a first band 2420 (which acts as a first tension member), a second band 2430 (which acts as a second tension member), an end effector 2460, and an actuator assembly 2700. The instrument 2400 is configured such that movement of the first band 2420 and second band 2430 produces movement of the wrist assembly 2500 about a first axis of rotation $A_1$ (which functions as the pitch axis, the term pitch is arbitrary), movement of the end effector 2460 about the second axis of rotation $A_2$ (which functions as the yaw axis, the term yaw is arbitrary), or both movement of the wrist assembly 2500 and movement of the end effector 2460. Although illustrated as bands, any of the bands discussed in this application may be substituted with other forms of tension members including, but not limited to, cables, wires, beams, rods, or a combination of one or more of bands, cables, wires, beams, or rods.

The wrist assembly 2500 (also referred to as a joint assembly) includes a first link 2510 and a second link 2610. The first link 2510 has a proximal portion 2511 that is coupled to a shaft 2410. The shaft 2410 can be any suitable elongated shaft that couples the wrist assembly 2500 to the actuator assembly 2700. For example, in some embodiments, the shaft 2410 can be a cylindrical shaft within which the first band 2420, the second band 2430 and other components routed from the actuator assembly 2700 to the wrist assembly 2500 are disposed (e.g., electrical wires, ground wires, or the like). The proximal portion 2511 can be coupled to the shaft 2410 via any suitable mechanism. For example, in some embodiments, the proximal portion 2511 can be matingly disposed within a portion of the shaft 2410 (e.g., via an interference fit). In some embodiments, the proximal portion 2511 can include one or more protrusions, recesses, openings, or connectors that couple the proximal portion 2511 to the shaft 2410. In some embodiments, the proximal portion 2511 can be welded, glued, or fused to the shaft 2410.

The second link 2610 has a proximal portion 2611 and a distal end portion 2612. The proximal portion 2611 is rotatably coupled to the first link 2510 to form the wrist assembly 2500 having the first axis of rotation $A_1$ about which the second link 2610 rotates relative to the first link 2510. The wrist assembly 2500 can include any suitable coupling mechanism. For example, in some embodiments, the second link 2610 can be coupled to the first link 2510 via a pinned joint of the types shown and described herein.

The distal end portion 2612 of the second link 2610 includes a connector 2680 that is coupled to a pulley portion 2467 of the end effector 2460 such that the end effector 2460 rotates relative to the wrist assembly 2500 about the second axis of rotation $A_2$. The second axis of rotation $A_2$ is non-parallel to the first axis of rotation $A_1$. The axis $A_2$ functions both as a yaw axis (the term yaw is arbitrary) in embodiments having multiple tool members as the tool members rotate together, and also as a grip axis as tool members rotate in opposition to each other. Thus, the instrument 2400 provides at least three degrees of freedom (i.e., a pitch motion about the first axis of rotation $A_1$, a yaw rotation about the second axis of rotation $A_2$, and a grip motion about the second axis of rotation $A_2$). The connector 2680 can be any suitable connector to rotatably couple the end effector 2460 to the wrist assembly 2500. For example, in some embodiments, the first link 2510 and/or the second link 2610 can include a clevis and a pin, such as the pinned joints shown and described in U.S. Pat. No. 9,204,923 B2 (filed Jul. 16, 2008), entitled "Medical Instrument Electronically Energized Using Drive Cables," which is incorporated herein by reference in its entirety. In other embodiments, the first link 2510 and/or the second link 2610 can include a compliant mechanism, such as the compliant mechanisms shown and described in International Patent Publication No. WO 2016/123139 A2 (filed Jan. 26, 2016), entitled "Rolling-Contact Joint Mechanisms and Methods," which is incorporated herein by reference in its entirety. In yet other embodiments, the wrist assembly 2500 can include any of the connectors or features shown and described in International Patent Application No. PCT/US18/64721 (filed Dec. 10, 2018), entitled "Medical Tools Having Tension Bands," which is incorporated herein by reference in its entirety.

The end effector 2460 is coupled to the wrist assembly 2500 and includes at least one tool member 2462. The tool member 2462 can include a contact portion 2464 and a pulley portion 2467. The contact portion 2464 is configured to engage or manipulate a target tissue during a surgical procedure. For example, in some embodiments, the contact portion 2464 can include an engagement surface that functions as a gripper, cutter, tissue manipulator, or the like. In other embodiments, the contact portion 2464 can be an energized tool member that is used for cauterization or electrosurgical procedures. As described above, the pulley portion 2467 is rotatably coupled to the second link 2610 such that the tool member 2462 rotates relative to the wrist assembly 2500 about the second axis of rotation $A_2$ in the direction of the arrow KK. In this manner, the contact portion 2464 of the tool member 2462 can be actuated about the second axis of rotation $A_2$ to engage or manipulate a target tissue during a surgical procedure. The tool member 2462 (or any of the tool members described herein) can be any suitable medical tool member. Moreover, although only one tool member 2462 is shown, in other embodiments, the instrument 2400 can include two moving tool members that cooperatively perform gripping or shearing functions.

The first band 2420 includes a proximal portion 2421 and a distal portion 2422, and the first band 2420 extends from the actuator assembly 2700, through the shaft 2410, and into the wrist assembly 2500. The proximal portion 2421 of the first band 2420 is attached to a first actuator 2800 of the actuator assembly 2700 and the distal portion 2422 is attached to the pulley portion 2467. The second band 2430 includes a proximal portion 2431 and a distal portion 2432, and the second band 2430 extends from the actuator assembly 2700, through the shaft 2410, and into the wrist assembly 2500. The proximal portion 2431 of the second band 2430 is attached to a first actuator 2800 of the actuator assembly 2700 and the distal portion 2432 is attached to the pulley portion 2467.

The first band 2420, second band 2430, and any of the bands described herein can have any suitable shape. For example, in some embodiments, any of the bands described herein can have a rectangular cross-sectional shape (taken within a cross-sectional plane normal to the longitudinal center line of the band). In other embodiments, any of the bands described herein can have a trapezoidal shape. In yet other embodiments, any of the bands described herein can include slightly curved surfaces. Moreover, any of the bands described herein can be constructed from any suitable materials. For example, in some embodiments, the first band 2420, the second band 2430, and any of the bands described herein can be constructed from a series of laminates that are bonded together (e.g., via an adhesive). In other embodiments, the laminates can be joined by any other suitable method. The laminates can be constructed from any suitable material, including tungsten, steel, or any suitable polymer. The bands can be similar to any of the bands shown and described in International Patent Application No. PCT/US18/64721 (filed Dec. 10, 2018), entitled "Medical Tools Having Tension Bands," which is incorporated herein by reference in its entirety.

As shown in FIGS. 6 and 7, the actuator assembly 2700 (which can function as a transmission or backend assembly) produces movement of the first band 2420 and the second band 2430, which operate to produce the desired articulation movements (pitch, yaw, or grip) at the wrist assembly 2500. Accordingly, as described herein, the actuator assembly 2700 includes components and controls to move one of the bands in a proximal direction (i.e., to pull in a certain band) while simultaneously allowing the distal movement (i.e., releasing or "paying out") of other of the bands. The actuator assembly 2700 can also move both the first band 2420 and the second band 2430 in the same direction. In this manner, the actuator assembly 2700 can maintain the desired tension within the bands to produce the desired movements at the wrist assembly 2500. Moreover, in some embodiments, the actuator assembly 2700 can ensure that the lengths of the bands are conserved (i.e., moved in equal amounts) during the entire range of motion of the wrist assembly 2500.

Specifically, the actuator assembly 2700 includes a housing 2760, a first actuator 2800, and a second actuator 2820. The housing 2760 (which functions as a chassis) provides the structural support for mounting and aligning the components of the actuator assembly 2700. For example, the housing 2760 can define openings, protrusions and/or brackets for mounting of shafts or other components. The first actuator 2800 is mounted to the actuator assembly 2700 (e.g., within the housing 2760) via a first actuator support member 2801. For example, the first actuator support member 2801 can be a mount, shaft, or any other suitable support structure to secure the first actuator 2800 to the actuator assembly 2700. In some embodiments, the proximal portion 2421 of the first band 2420 is attached to the first actuator 2800 at a first location, and the proximal portion 2431 of the second band 2430 is attached to the first actuator 2800 at a second location different from the first location. Both the proximal portion 2421 and the proximal portion 2431 can be attached to the first actuator 2800 via one or more fasteners. For example, the proximal portion 2421 of the first band 2420 and the proximal portion 2431 of the second band 2430 may be secured to the first actuator 2800 via bolts or screws.

As shown in FIGS. 5-7, the second actuator 2820 is mounted to the actuator assembly 2700 (e.g., within the housing 2760) via a second actuator support member 2821. For example, the second actuator support member 2821 can be a mount, shaft, or any other suitable support structure to secure the second actuator 2820 to the actuator assembly 2700. In some embodiments, the second actuator 2820 is a linear actuator operable to produce a linear movement in the direction shown by the arrow DD. The direction of travel of the second actuator 2820 is non-parallel to the directions of travel indicated by the arrows BB and CC for the first band 2420 and the second band 2430 (i.e., include a component of travel that is perpendicular to the arrows BB and CC). In other embodiments, the second actuator 2820 includes a lever or cam operable to produce linear movement in the direction of the arrow DD.

The second actuator 2820 includes a guide structure 2822 with a first guide surface 2823 and a second guide surface 2824. The first guide surface 2823 is in contact with the proximal portion 2421 of the first band 2420. The second guide surface 2824 is in contact with the proximal portion 2431 of the second band 2430. In this manner, as described herein, movement of the second actuator 2820 will produce a movement of the first band 2420 and the second band 2430. Moreover, such movement can be independent from the movement of the first band 2420 and the second band 2430 produced by the first actuator 2800. The first guide surface 2823 and the second guide surface 2824 can be any suitable surfaces and can include any suitable features to contact and impart movement to the first band 2420 and the second band 2430. In some embodiments, the proximal portion 2421 of the first band 2420 may be spaced apart from the first guide surface 2823, and the proximal portion 2431 of the second band 2430 may be spaced apart from the second guide surface 2824 when the second actuator 2820 is in a neutral position prior to being actuated and moved in the direction of the arrow DD, as described below.

Movement produced by the first actuator 2800 is translated to the proximal portion 2421 of the first band 2420 and to the proximal portion 2431 of the second band 2430. In some embodiments, the first actuator 2800 is operable to produce a rotational movement about a first actuator axis $A_3$ in the direction of the arrow AA. The proximal portion 2421 can be attached to the first actuator 2800 in a first orientation, and the proximal portion 2431 can be attached to the first actuator 2800 in a second orientation opposite to the first orientation, such that when the first actuator 2800 is rotated in the direction of the arrow AA, the first band 2420 is moved in a distal direction (i.e., released) in the direction of the arrow BB, while simultaneously the second band 2430 is moved in a proximal direction (i.e., pulled) in the direction of the arrow CC. The length of the first band 2420 being released can be the same length of the second band 2430 being pulled or taken up to ensure that the lengths of the bands can be conserved (i.e., moved in equal amounts) during the entire range of motion of the wrist assembly 2500. In other embodiments, the first actuator 2800 may be configured as a linear actuator to move the first band 2420 and the second band 2430 in the directions shown by the arrows BB and CC, respectively.

As the first band 2420 is moved in the direction of the arrow BB and the second band 2430 is moved in the direction of the arrow CC, the distal portion 2422 of the first band 2420 is fed to the pulley portion 2467 while the distal portion 2432 of the second band 2430 is taken up from the pulley portion 2467, causing the pulley portion 2467 and the tool member 2462 to rotate about the second axis of rotation $A_2$ in the direction shown by the arrow KK in FIG. 5. Conversely, when the first actuator 2800 is rotated in a direction opposite of the arrow AA in FIG. 6, the distal portion 2422 of the first band 2420 is taken up from the pulley portion 2467, and the distal portion 2432 of the second band 2430 is fed to the pulley portion 2467, urging the pulley portion 2467 and the tool member 2462 to rotate about the second axis of rotation $A_2$ in the direction opposite of the arrow KK in FIG. 5.

When the second actuator 2820 is moved in the direction of the arrow DD, as shown in FIG. 7, length from both the first band 2420 and the second band 2430, external to the actuator assembly 2700, are taken up. As the lengths are taken up, the distal portion 2422 of the first band 2420 and the distal portion 2432 of the second band 2430 are moved in direction of the arrow CC. The movement of the distal portion 2422 and the distal portion 2432 in turn applies a force on the pulley 2467 and urges the second link 2610 to rotate about the first axis of rotation $A_1$ in the direction of the arrow LL. Thus, the combination of the first actuator 2800, the second actuator 2820, and one set of bands (the first band 2420 and the second band 2430) are operable to control the end effector 2460 and the wrist assembly 2500 of instrument 2400 in at least 2 DOFs (e.g., pitch and yaw).

As discussed above, although the end effector 2460 in FIG. 5 is shown with only one tool member 2462, two (or more) tool members may be provided and a second tool member may be fixed or rotatably mounted relative to the second link 2610. For example, FIGS. 8-11 are diagrammatic illustrations of various portions of an instrument 3400, according to an embodiment. The instrument 3400 includes a wrist assembly 3500, a first band 3420 (which acts as a first tension member), a second band 3430 (which acts as a second tension member), a third band 3440 (which acts as a third tension member), a fourth band 3450 (which acts as a fourth tension member), an end effector 3460, and an actuator assembly 3700. The end effector 3460 can include a first tool member 3462 coupled to a first pulley portion 3467 and a second tool member 3472 coupled to a second pulley portion 3477. Although shown as including the first band 3420, a second band 3430, a third band 3440, and a fourth band 3450, in other embodiments, other forms of tension members may be employed as described herein.

The wrist assembly 3500 (also referred to as a joint assembly) includes a first link 3510 and a second link 3610. The first link 3510 has a proximal portion 3511 that is coupled to a shaft 3410. The shaft 3410 can be any suitable elongated shaft such as those described above with reference to shaft 2410. The second link 3610 has a proximal portion 3611 and a distal end portion 3612. The proximal portion 3611 is rotatably coupled to the first link 3510 to form the wrist assembly 3500 having the first axis of rotation $A_1$ (which functions as the pitch axis, the term pitch is arbitrary) about which the second link 3610 rotates relative to the first link 3510. The wrist assembly 3500 can include any suitable coupling mechanism shown and described herein. The distal end portion 3612 of the second link 3610 includes a connector 3680 that is coupled to the first pulley portion 3467 of the first tool member 3462 and the second pulley portion 3477 of the second tool member 3472. The first pulley portion 3467 and the second pulley portion 3477 are coupled to rotate, either independently or in unison, relative to the wrist assembly 3500 about a second axis of rotation $A_2$. The second axis of rotation $A_2$ is non-parallel to the first axis of rotation $A_1$. The axis $A_2$ functions both as a yaw axis (the term yaw is arbitrary) when the first and second tool members 3462, 3472 rotate together, and as a grip axis when the first and second tool members 3462, 3472 rotate in opposition to each other. The connector 3680 can be any suitable connector to rotatably couple the end effector 3460 to the wrist assembly 3500 as described herein.

The first tool member 3462 can include a contact portion 3464 and the second tool member 3472 can include a contact portion 3474. The contact portions 3464, 3474 are configured to engage or manipulate a target tissue during a surgical procedure. For example, the contact portions 3464, 3474 can include engagement surfaces that function as a gripper, cutter, tissue manipulator, or the like. In other embodiments, the contact portions 3464, 3474 can be energized tool members used for cauterization or electrosurgical procedures. As described above, the first and second tool members 3462, 3472 are rotatably coupled to the second link 3610 such that the first tool member 3462 and the second tool member 3472 can rotate relative to the wrist assembly 3500 about the second axis of rotation $A_2$. In this manner, the contact portion 3464 of the first tool member 3462 can be actuated in a direction of the arrow KK and the contact portion 3474 of the second tool member 3472 can be actuated in a direction opposite of the arrow KK to bring the contact portions 3464, 3474 closer together to grasp, cut, engage, or manipulate a target tissue during a surgical procedure. Conversely, the contact portion 3464 of the first tool member 3462 can be actuated in a direction opposite of the arrow KK and the contact portion 3474 of the second tool member 3472 can be actuated in the direction of the arrow KK to separate the contact portions 3464, 3474 from each other and release the target tissue.

Figure 8:
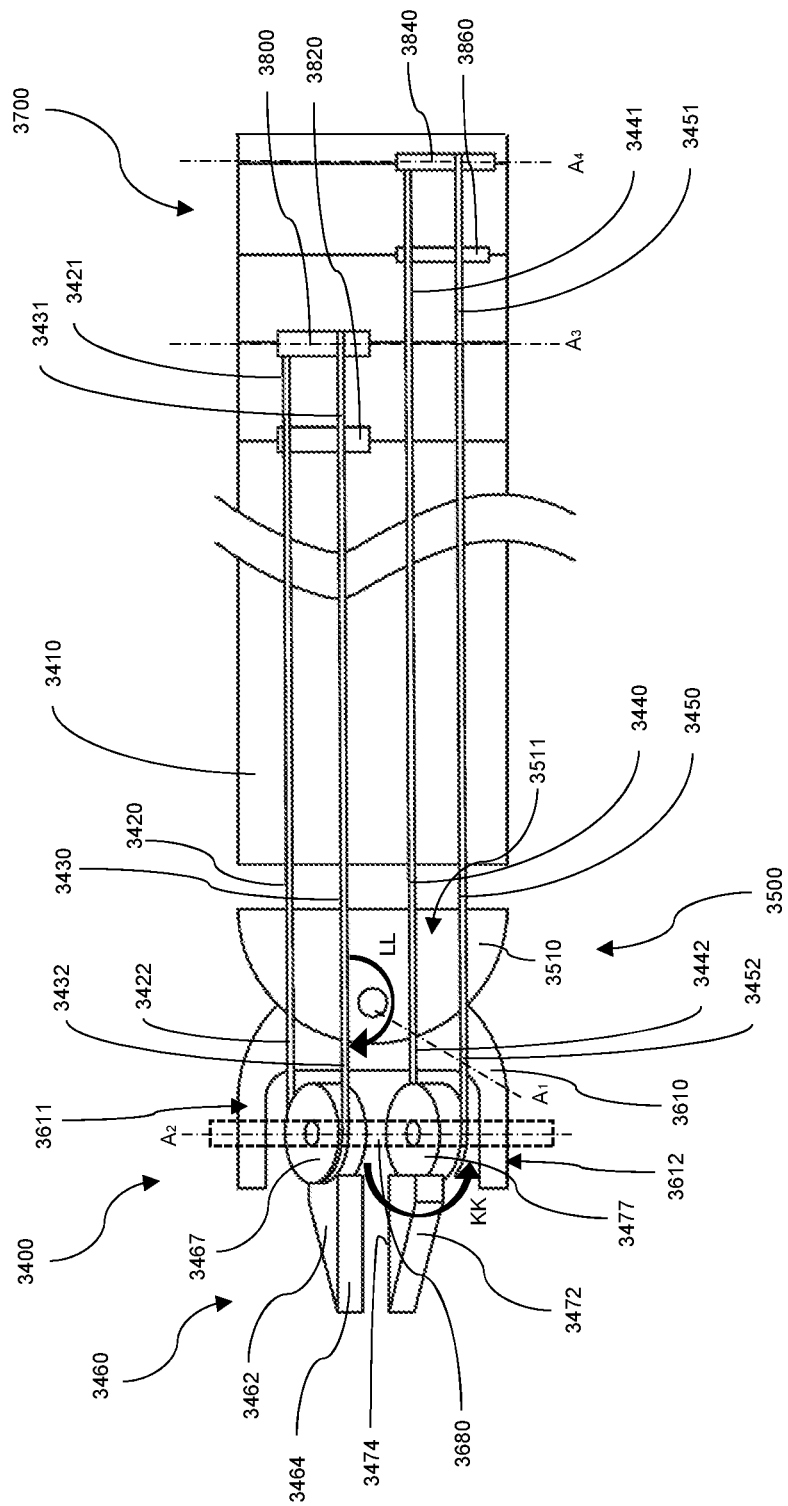
FIG. 8 is a diagrammatic illustration of a portion of an instrument including two sets of bands and four actuators, according to an embodiment.

As shown in FIG. 8, the first pulley portion 3467 is coupled to a distal portion 3422 of the first band 3420 and to a distal portion 3432 of the second band 3430. The second pulley portion 3477 is coupled to a distal portion 3442 of the third band 3440 and to a distal portion 3452 of the fourth band 3450. Each of the first, second, third, and fourth bands 3420, 3430, 3440, 3450 extend from their respective distal portions out of the wrist assembly 3500, through the shaft 3410, and into the actuator assembly 3700.

Figure 9:
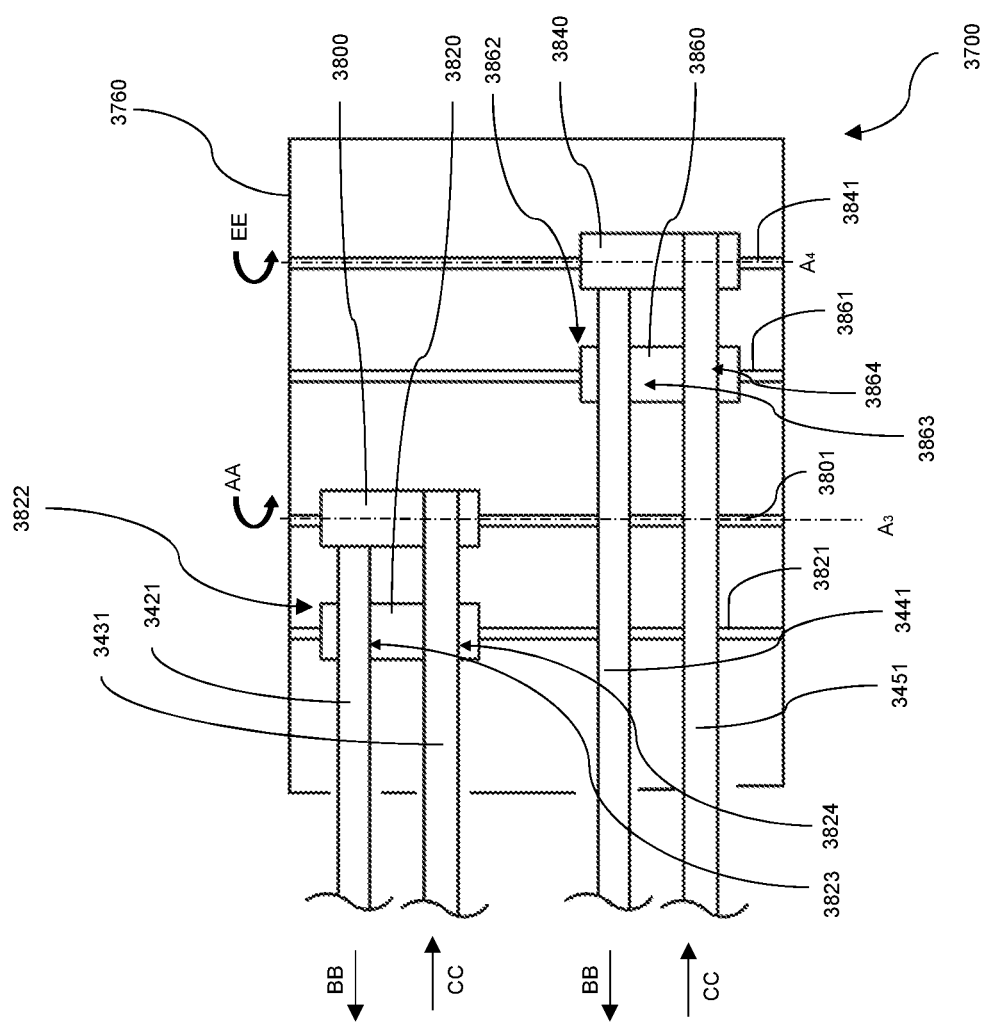
FIG. 9 an enlarged diagrammatic illustration of the actuator assembly of the portion of the instrument of FIG. 8 depicting operating states of the first and third actuators.
Figure 10:
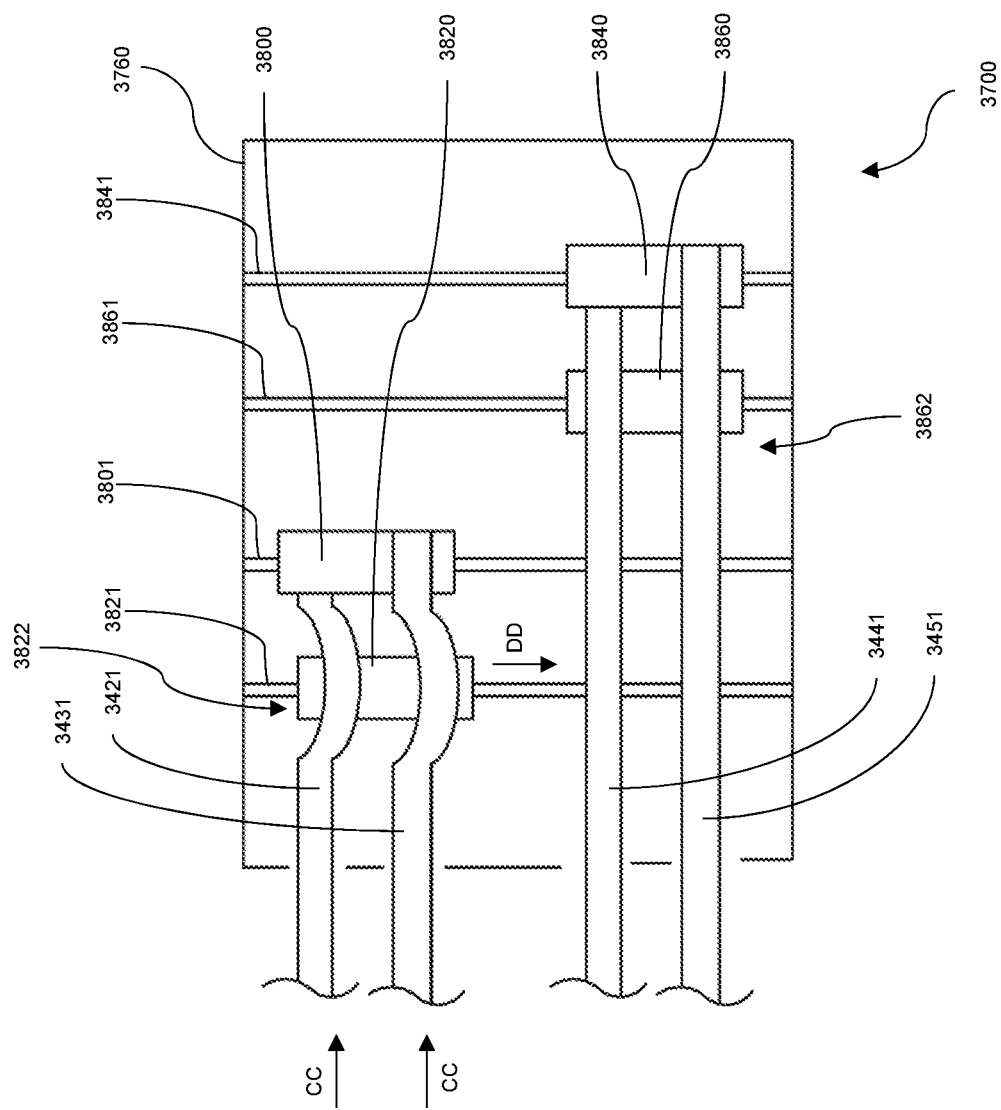
FIG. 10 is an enlarged diagrammatic illustration of the actuator assembly of the portion of the instrument of FIG. 8 depicting an operating state of the second actuator.
Figure 11:
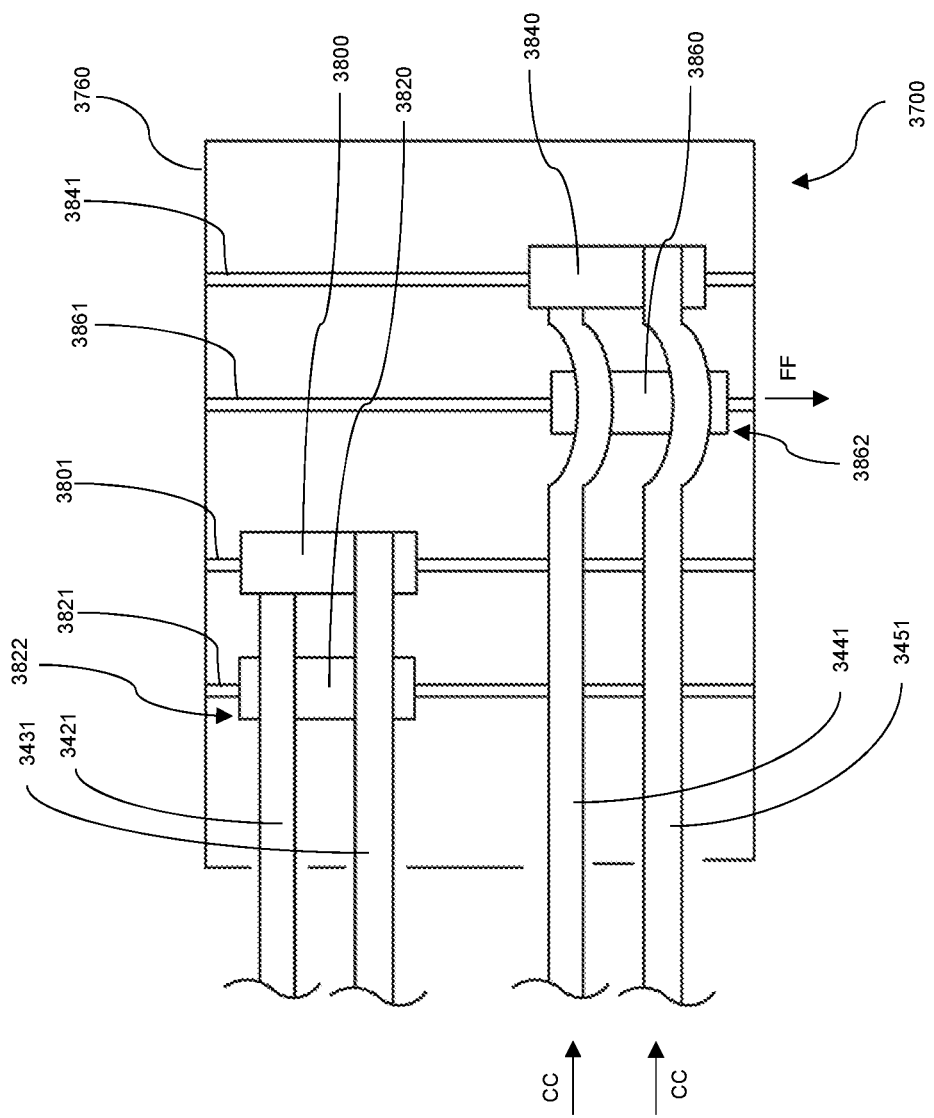
FIG. 11 is an enlarged diagrammatic illustration of the actuator assembly of the portion of the instrument of FIG. 8 depicting an operating state of the fourth actuator.

As shown in FIGS. 9-11, the actuator assembly 3700 (which can function as a transmission assembly) produces movement of the first band 3420 and the second band 3430 (collectively the first set of bands) and/or produces movement of the third band 3440 and the fourth band 3450 (collectively the second set of bands). In this manner, different combinations of movement of the bands operate to produce the desired articulation movements (pitch, yaw, or grip) at the wrist assembly 3500. Accordingly, as described herein, the actuator assembly 3700 includes components and controls each set of bands to move one of the bands in a proximal direction (i.e., to pull in a certain band) while simultaneously allowing the distal movement (i.e., releasing or "paying out") of other of the bands. The actuator assembly 3700 can also move both bands of either the first set or second set of bands in the same direction. In this manner, the actuator assembly 3700 can generate the desired torque via the bands to produce the desired movements at the wrist assembly 3500. Moreover, in some embodiments, the actuator assembly 3700 can ensure that the lengths of the bands are conserved (i.e., moved in equal amounts) during the entire range of motion of the wrist assembly 3500.

Specifically, the actuator assembly 3700 includes a housing 3760, a first actuator 3800, a second actuator 3820, a third actuator 3840, and a fourth actuator 3860. The housing 3760 (which functions as a chassis) provides the structural support for mounting and aligning the components of the actuator assembly 3700. For example, the housing 3760 can define openings, protrusions and/or brackets for mounting shafts or other components. The first actuator 3800 is mounted to the actuator assembly 3700 via a first actuator support member 3801, the second actuator 3820 is mounted to the actuator assembly 3700 via a second actuator support member 3821, the third actuator 3840 is mounted to the actuator assembly 3700 via a third actuator support member 3841, and the fourth actuator 3860 is mounted to the actuator assembly 3700 via a fourth actuator support member 3861. As described herein, the support members 3801, 3821, 3841, 3861 may be any suitable support structure that secures the support member to the actuator assembly 3700 while enabling the corresponding actuators to transmit rotation and or linear movement to one or more attached bands.

As shown in FIG. 9, the proximal portion 3421 of the first band 3420 is attached to the first actuator 3800 at a first location, and the proximal portion 3431 of the second band 3430 is attached to the first actuator 3800 at a second location different from the first location. Both the proximal portion 3421 and the proximal portion 3431 can be attached to the first actuator 3800 via one or more fasteners as described herein. The proximal portion 3441 of the third band 3440 is attached to the third actuator 3840 at a first location, and the proximal portion 3451 of the fourth band 3450 is attached to the third actuator 3840 at a second location different from the first location. Both the proximal portion 3421 and the proximal portion 3431 can be attached to the third actuator 3840 via one or more fasteners as described herein.

Operation of the first actuator 3800 coupled to the first band 3420 and the second band 3430 is similar to the operation of the first actuator 2800 coupled to the first band 2420 and the second band 2430, as described above with reference to FIGS. 5 and 6. For example, movement produced by the first actuator 3800 about a first actuator axis $A_3$ in the direction of the arrow AA urges the first band 3420 to move in the direction of the arrow BB and urges the second band 3430 to move in the direction of the arrow CC, as shown in FIG. 9. The movement of the first band 3420 and the second band 3430 in turn urges the first pulley portion 3467 and first tool member 3462 to rotate relative to the wrist assembly 3500 about the second axis of rotation $A_2$ in the direction of the arrow KK. Conversely, rotation of the first actuator 3800 in the direction opposite of arrow AA urges the first pulley portion 3467 and first tool member 3462 to rotate in the direction opposite of the arrow KK in FIG. 9.

Operation of the third actuator 3840 coupled to the third band 3440 and the fourth band 3450 is similar to that of the first actuator 3800 on the first band 3420 and the second band 3430. For example, movement produced by the third actuator 3840 about a third actuator axis $A_4$ in the direction of the arrow EE urges the second pulley portion 3477 and the second tool member 3472 to rotate relative to the wrist assembly 3500 about the second axis of rotation $A_2$ in the direction of the arrow KK. Conversely, rotation of the third actuator 3840 in the direction opposite of arrow EE urges the second pulley portion 3477 and second tool member 3472 to rotate in the direction opposite of the arrow KK in FIG. 9.

In one operating state, both the first actuator 3800 and the third actuator 3840 can be operated to actuate together (i.e., together in the direction of the arrow AA and the arrow EE for the first actuator 3800 and the third actuator 3840, respectively, or together in the direction opposite of the arrows) to urge both the first pulley portion 3467 and second pulley portion 3477 to rotate together in the direction of the arrow KK, or rotate together in the direction opposite of the arrow KK, thereby enabling control of the first tool member 3462 and the second tool member 3472 about the second axis of rotation $A_2$ (e.g., yaw). In another operating state, both of the first actuator 3800 and the third actuator 3840 can be operated to actuate in opposite directions (i.e., in the direction of the arrow AA for the first actuator 3800 and the direction opposite of the arrow EE for the third actuator 3840) to urge both the first pulley portion 3467 and second pulley portion 3477 to rotate in opposite directions about the second axis of rotation $A_2$ in order to bring the first tool member 3462 and the second tool member 3472 closer together or apart, thereby enabling a second DOF about the second axis of rotation $A_2$ (e.g., grip). In yet another operating state, one of the first actuator 3800 or the third actuator 3840 is actuated (i.e., in the direction of the arrow AA for the first actuator 3800 or in the direction opposite of the arrow EE for the third actuator 3840) while the other of the first tool member 3462 or the second tool member 3472 is kept stationary. In this state, the tool member associated with the stationary actuator can be maintained at a fixed position while the other tool member associated with the active actuator is moved towards the fixed tool member, which may be beneficial for certain procedures where continued contact or support of a target tissue is required prior to a grasping, shearing or cauterization with both the tool members. Other combinations of simultaneous yaw and grip actuation via control of one or both the first actuator 3800 or the third actuator 3840 will be evident to one skilled in the art in view of the present disclosure.

With reference to FIGS. 9 and 10, the second actuator 3820 includes a guide structure 3822 with a first guide surface 3823 and a second guide surface 3824. The first guide surface 3823 and the second guide surface 3824 may be spaced from each other in a longitudinal direction relative to a central axis of the second actuator 3820 The first guide surface 3823 is in contact with the proximal portion 3421 of the first band 3420. The second guide surface 3824 is in contact with the proximal portion 3431 of the second band 3430. In some embodiments, the proximal portion 3421 of the first band 3420 may be spaced apart from the first guide surface 3823, and the proximal portion 3431 of the second band 3430 may be spaced apart from the second guide surface 3824 when the second actuator 3820 is in a neutral position prior to being actuated and moved in the direction of the arrow DD as shown in FIG. 10. The operation of the second actuator 3820 on the first band 3420 and the second band 3430 is similar to the operation of the second actuator 2820 on the first band 2420 and the second band 2430. For example, the second actuator 3820 is a linear actuator operable to produce a linear movement in the direction shown by the arrow DD. The direction of travel of the second actuator 3820 is non-parallel to the directions of travel indicated by the arrows BB and CC for the first band 3420 and the second band 3430 in FIG. 9 (i.e., include a component of travel that is perpendicular to the arrows BB and CC). In other embodiments, the second actuator 3820 includes a lever or cam operable to produce linear movement in the direction of the arrow DD.

When the second actuator 3820 is moved in the direction of the arrow DD, as shown in FIG. 10, length from both the first band 3420 and the second band 3430, external to the actuator assembly 3700, are taken up. As the lengths are taken up, the distal portion 3422 of the first band 3420 and the distal portion 3432 of the second band 3430 are moved in direction of the arrow CC. The movement of the distal portions 3422, 3432 in turn applies a force on the first pulley 3467 and urges the second link 3610 to rotate about the first axis of rotation $A_1$ in the direction of the arrow LL.

With reference to FIGS. 9 and 11, the fourth actuator 3860 includes a guide structure 3862 with a first guide surface 3863 and a second guide surface 3864. The first guide surface 3863 and the second guide surface 3864 may be spaced from each other in a longitudinal direction relative to a central axis of the fourth actuator 3860. The first guide surface 3863 is in contact with the proximal portion 3441 of the third band 3440. The second guide surface 3864 is in contact with the proximal portion 3451 of the fourth band 3450. In some embodiments, the proximal portion 3441 of the third band 3440 may be spaced apart from the first guide surface 3863, and the proximal portion 3451 of the fourth band 3450 may be spaced apart from the second guide surface 3864 when the fourth actuator 3860 is in a neutral position prior to being actuated and moved in the direction of the arrow FF as shown in FIG. 11. The operation of the fourth actuator 3860 on the third band 3440 and the fourth band 3450 is similar to the operation of the second actuator 3820 on the first band 3420 and the second band 3430. For example, the fourth actuator 3860 is a linear actuator operable to produce a linear movement in the direction shown by the arrow FF. The direction of travel of the fourth actuator 3860 is non-parallel to the directions of travel indicated by the arrows BB and CC for the third band 3440 and the fourth band 3450 in FIG. 9 (i.e., include a component of travel that is perpendicular to the arrows BB and CC). In other embodiments, the fourth actuator 3860 includes a lever or cam operable to produce linear movement in the direction of the arrow FF.

When the fourth actuator 3860 is moved in the direction of the arrow FF, as shown in FIG. 11, length from both the third band 3440 and the fourth band 3450, external to the actuator assembly 3700, are taken up. As the lengths are taken up, the distal portion 3442 of the third band 3440 and the distal portion 3452 of the fourth band 3450 are moved in direction of the arrow CC. The movement of the distal portion 3442 and the distal portion 3452 in turn applies a force on the second pulley 3477 and urges the second link 3610 to rotate about the first axis of rotation $A_1$ in the direction opposite of the arrow LL. By alternating actuation between the second actuator 3820 and the fourth actuator 3860, the second link 3610 is operable to pivot back and forth about the first axis of rotation $A_1$ (e.g., pitch, the term pitch is arbitrary). Thus, the combination of at least four actuators (the first, second, third and fourth actuators 3800, 3820, 3840, 3860), a first set of bands (the first and second bands 3420, 3430) and a second set of bands (the third and fourth bands 3440, 3450) are operable to provide the end effector 3460 and the wrist assembly 3500 of instrument 3400 with at least 3 DOFs (e.g., pitch, yaw, and grip).

Although the actuator assembly 3700 is shown as having the second actuator 3820 separate from the fourth actuator 3860, in other embodiments, an actuator assembly can include any suitable arrangement of actuators. For example, FIGS. 12-15 are diagrammatic illustrations of various portions of an instrument 4400, according to an embodiment. The instrument 4400 includes a wrist assembly 4500, a first band 4420 (which acts as a first tension member), a second band 4430 (which acts as a second tension member), a third band 4440 (which acts as a third tension member), a fourth band 4450 (which acts as a fourth tension member), an end effector 4460, and an actuator assembly 4700. The end effector 4460 can include a first tool member 4462 coupled to a first pulley portion 4467 and a second tool member 4472 coupled to a second pulley portion 4477. Although shown as including the first band 4420, a second band 4430, a third band 4440, and a fourth band 4450, in other embodiments, other forms of tension members may be employed as described herein.

The wrist assembly 4500 (also referred to as a joint assembly) includes a first link 4510 and a second link 4610. The first link 4510 has a proximal portion 4511 that is coupled to a shaft 4410. The shaft 4410 can be any suitable elongated shaft such as those described above with reference to shaft 2410. The second link 4610 has a proximal end portion 4611 and a distal end portion 4612. The proximal end portion 4611 is rotatably coupled to the first link 4510 to form the wrist assembly 4500 having the first axis of rotation $A_1$ (which functions as the pitch axis, the term pitch is arbitrary) about which the second link 4610 rotates relative to the first link 4510. The wrist assembly 4500 can include any suitable coupling mechanism shown and described herein. The distal end portion 4612 of the second link 4610 includes a connector 4680 that is coupled to the first pulley portion 4467 of the first tool member 4462 and the second pulley portion 4477 of the second tool member 4472. The first pulley portion 4467 and the second pulley portion 4477 are coupled to rotate, either independently or in unison, relative to the wrist assembly 4500 about a second axis of rotation $A_2$. The second axis of rotation $A_2$ is non-parallel to the first axis of rotation $A_1$. The axis $A_2$ functions both as a yaw axis (the term yaw is arbitrary) as the first and second tool members 4462, 4472 rotate together and as a grip axis as the first and second tool members 4462, 4472 rotate in opposition to each other. The connector 4680 can be any suitable connector to rotatably couple the end effector 4460 to the wrist assembly 4500 as described herein.

The first tool member 4462 can include a contact portion 4464 and the second tool member 4472 can include a contact portion 4474. The contact portions 4464, 4474 are configured to engage or manipulate a target tissue during a surgical procedure. For example, the contact portions 4464, 4474 can include engagement surfaces that function as a gripper, cutter, tissue manipulator, or the like. In other embodiments, the contact portions 4464, 4474 can be energized tool members used for cauterization or electrosurgical procedures. As described above, the first and second tool members 4462, 4472 are rotatably coupled to the second link 4610 such that the first tool member 4462 and the second tool member 4472 can rotate relative to the wrist assembly 4500 about the second axis of rotation $A_2$. In this manner, the contact portion 4464 of the first tool member 4462 can be actuated in a direction shown by the arrow KK and the contact portion 4474 of the second tool member 4472 can be actuated in a direction opposite of the arrow KK to bring the contact portions 4464, 4474 closer together to grasp, cut, engage, or manipulate a target tissue during a surgical procedure. Conversely, the contact portion 4464 of the first tool member 4462 can be actuated in a direction opposite of the arrow KK and the contact portion 4474 of the second tool member 4472 can be actuated in the direction of the arrow KK to separate the contact portions 4464, 4474 and release the target tissue.

Figure 12:
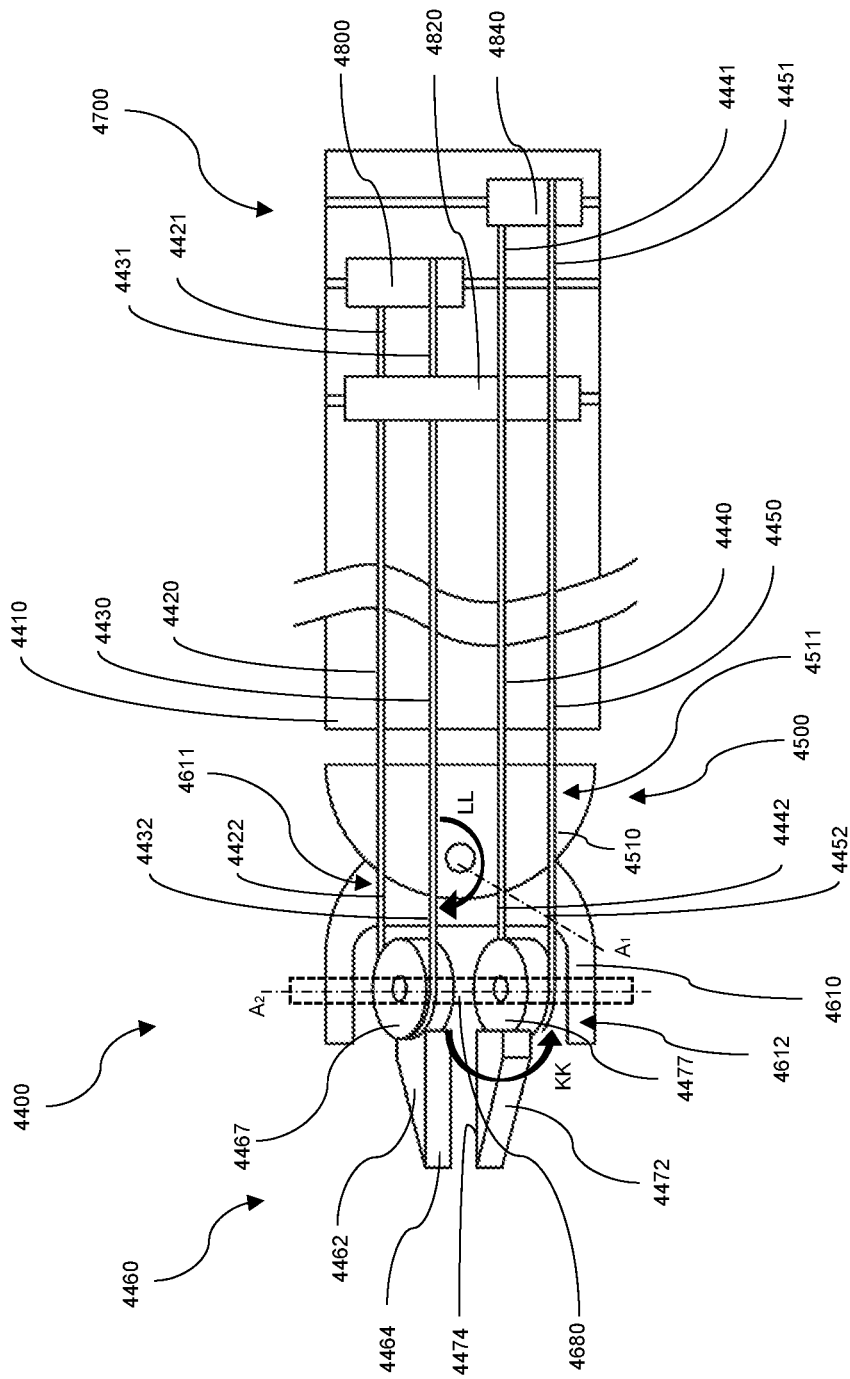
FIG. 12 is a diagrammatic illustration of a portion of an including two sets of bands and three actuators, according to an embodiment.

As shown in FIG. 12, the first pulley portion 4467 is coupled to a distal portion 4422 of the first band 4420 and to a distal portion 4432 of the second band 4430. The second pulley portion 4477 is coupled to a distal portion 4442 of the third band 4440 and to a distal portion 4452 of the fourth band 4450. Each of the first band 4420, the second band 4430, the third band 4440, and the fourth band 4450 extend from their respective distal portions out of the wrist assembly 4300, through the shaft 4410, and into the actuator assembly 4700.

Figure 13:
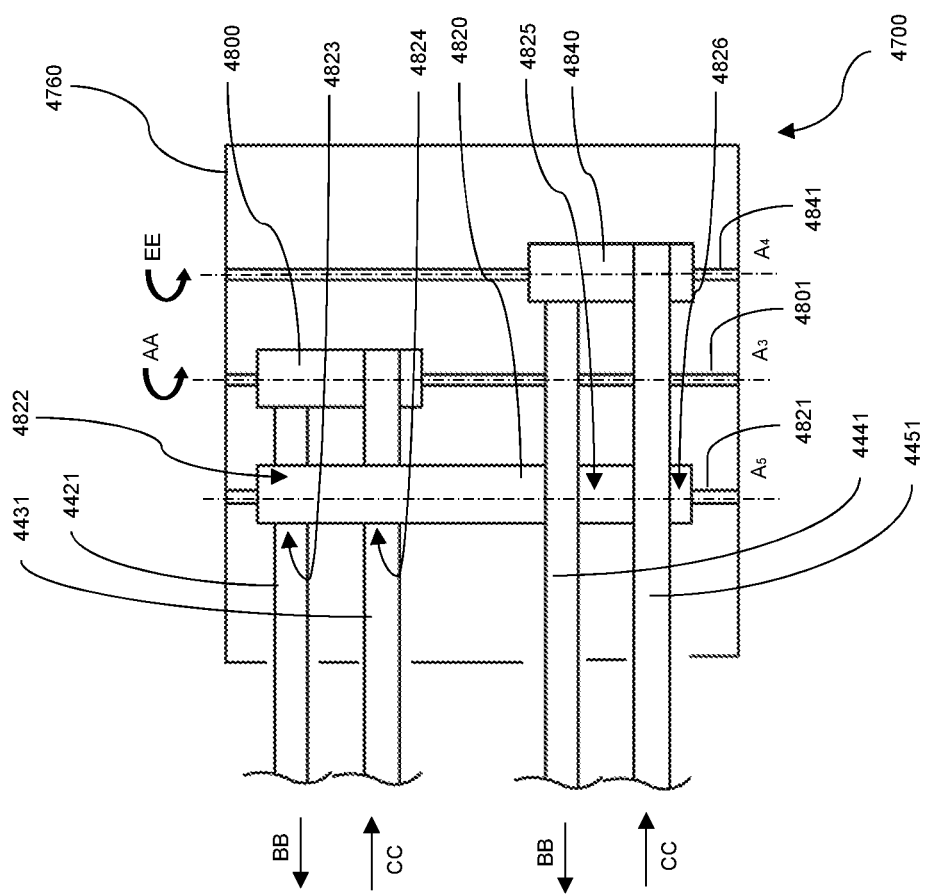
FIG. 13 is an enlarged diagrammatic illustration of the actuator assembly of the portion of the instrument of FIG. 12 depicting an operating state of the first actuator.
Figure 14:
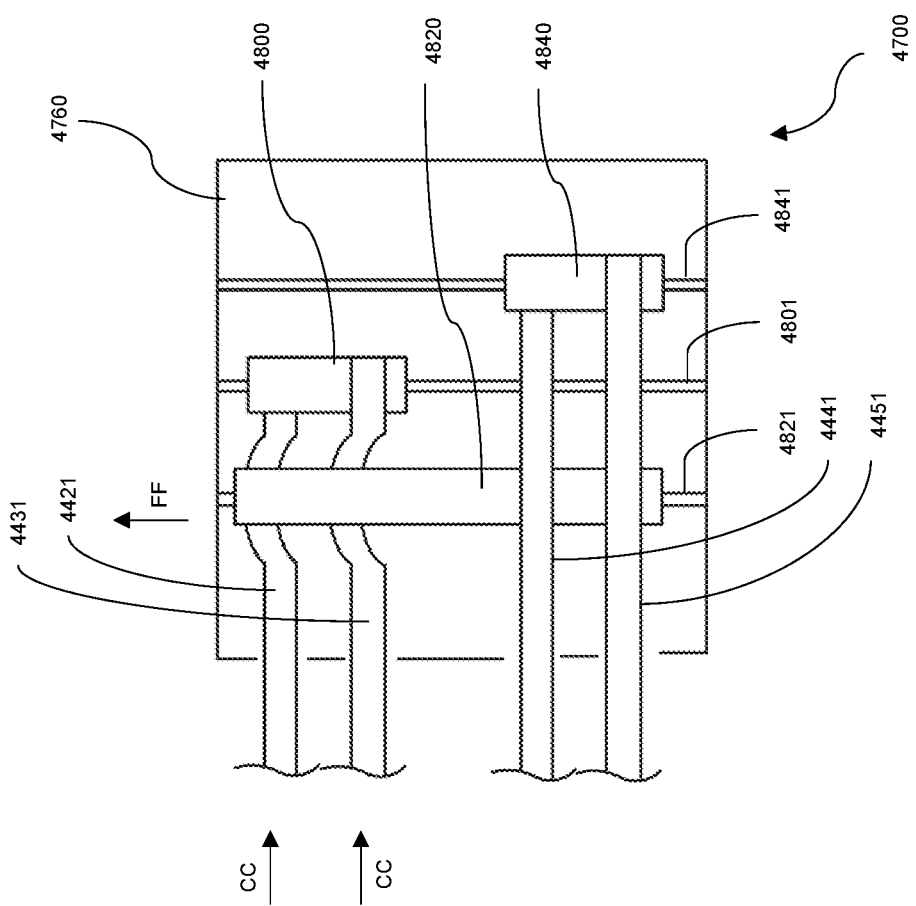
FIG. 14 is an enlarged diagrammatic illustration of the actuator assembly of the portion of the instrument of FIG. 12 depicting an operating state of the third actuator.
Figure 15:
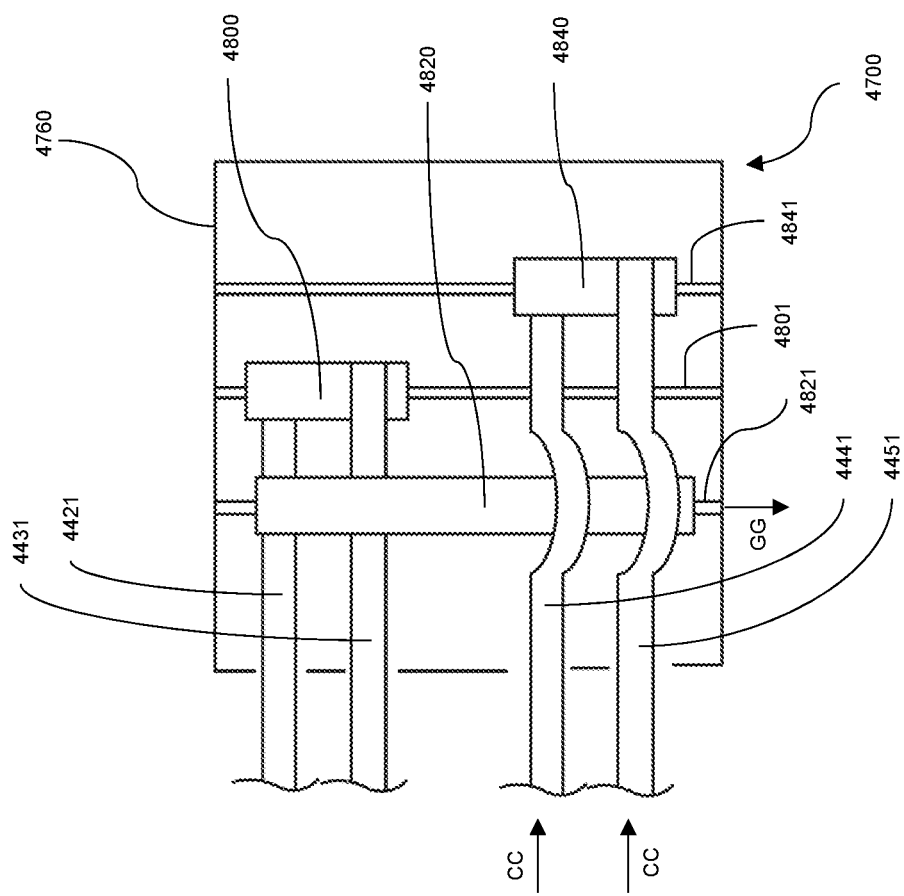
FIG. 15 is an enlarged diagrammatic illustration of the actuator assembly of the portion of the instrument of FIG. 12 depicting an operating state of the second actuator.
Figure 16:
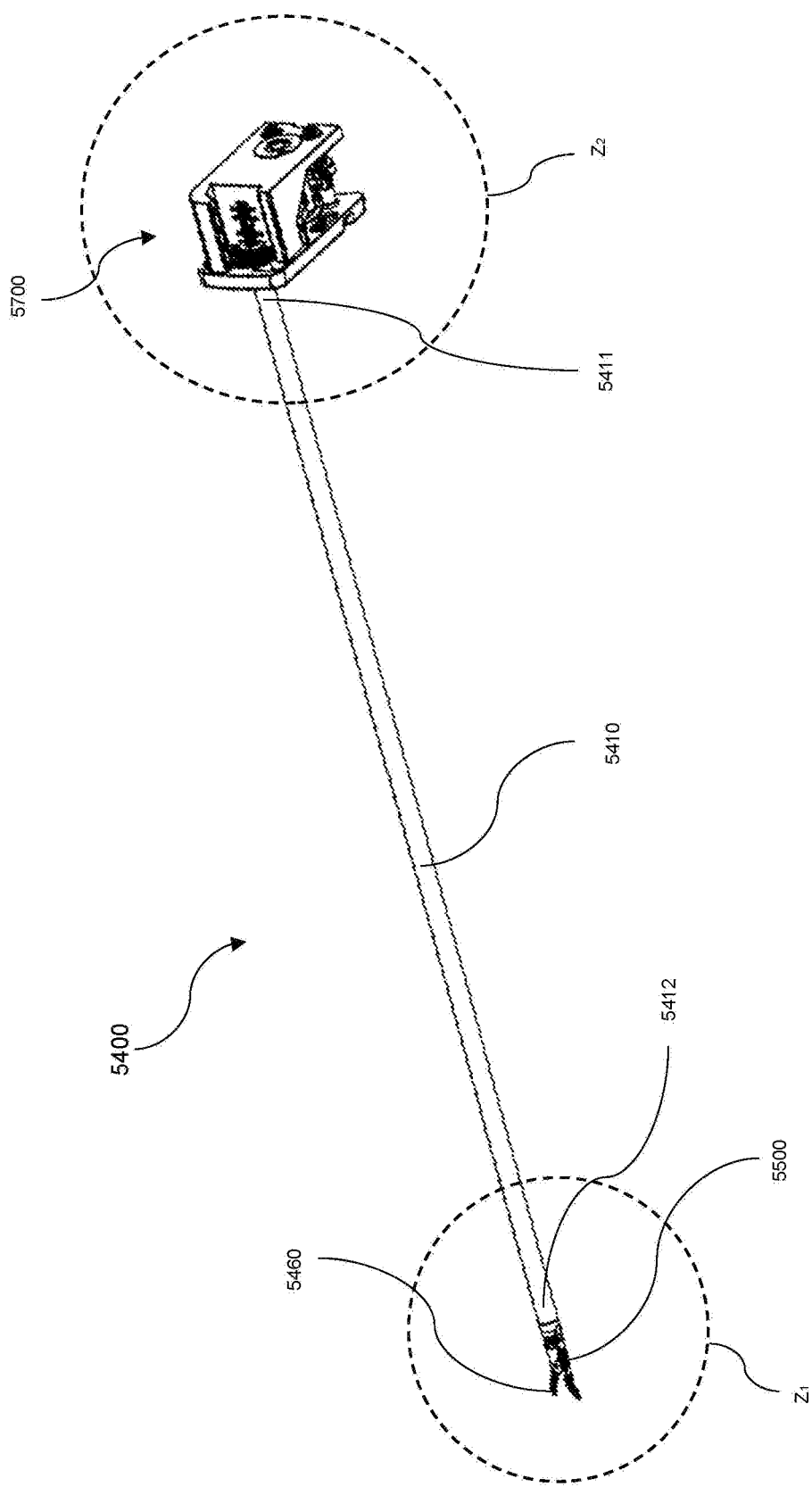
FIG. 16 is a perspective view of an instrument of a surgery system, according to an embodiment.
Figure 18:
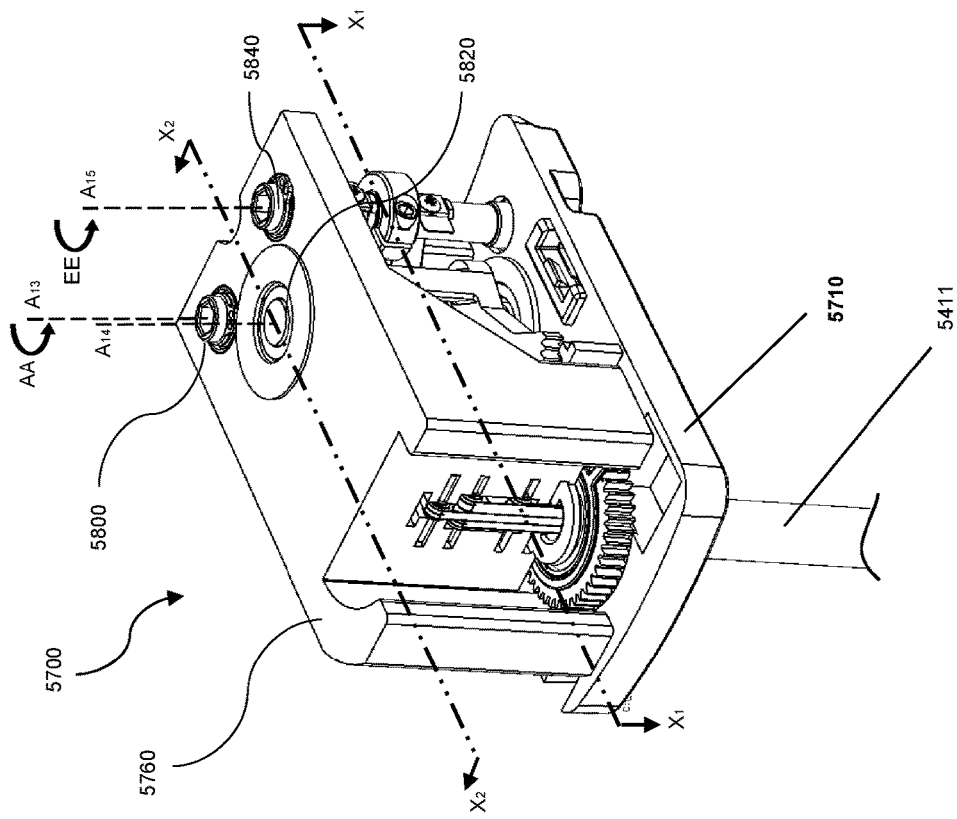
FIG. 18 is an enlarged perspective view of an actuator assembly at the proximal end portion of the instrument indicated by the region $Z_2$ shown in FIG. 16.
Figure 17:
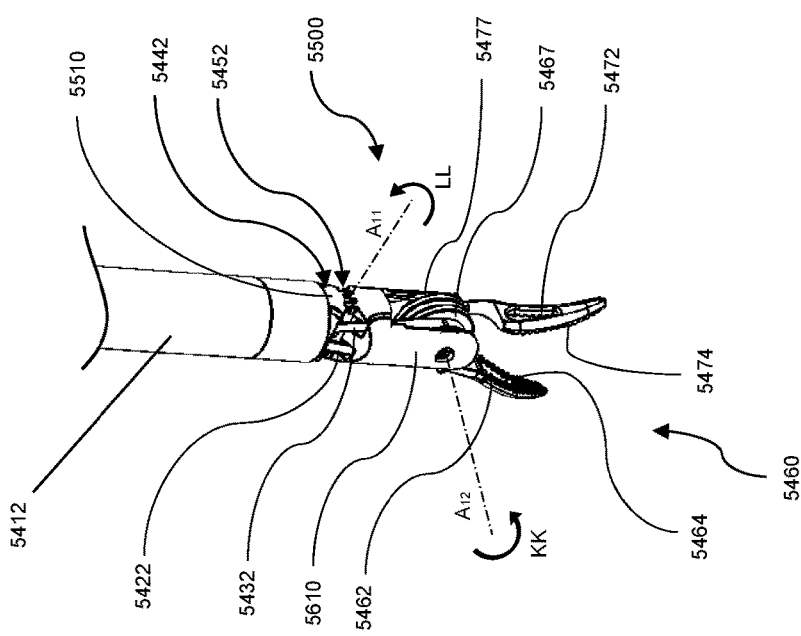
FIG. 17 is an enlarged perspective view of an end effector and a wrist assembly at the distal end portion of the instrument indicated by the region $Z_1$ shown in FIG. 16.

As shown in FIGS. 13-15, the actuator assembly 4700 (which can function as a transmission assembly) produces movement of the first band 4420 and the second band 4430 (collectively the first set of bands) and/or produce movement of the third band 4440 and the fourth band 4450 (collectively the second set of bands). In this manner, different combinations of movement of the bands operate to produce the desired articulation movements (pitch, yaw, or grip) at the wrist assembly 4500. Accordingly, as described herein, the actuator assembly 4700 includes components and controls each set of bands to move one of the bands in a proximal direction (i.e., to pull in a certain band) while simultaneously allowing the distal movement (i.e., releasing or "paying out") of other of the bands. The actuator assembly 4700 can also move both bands in either the first set or second set of bands in the same direction. In this manner, the actuator assembly 4700 can maintain the desired tension within the bands to produce the desired movements at the wrist assembly 4500. Moreover, in some embodiments, the actuator assembly 4700 can ensure that the lengths of the bands are conserved (i.e., moved in equal amounts) during the entire range of motion of the wrist assembly 4500.

Specifically, the actuator assembly 4700 includes a housing 4760, a first actuator 4800, a second actuator 4820, a third actuator 4840. The housing 4760 (which functions as a chassis) provides the structural support for mounting and aligning components of the actuator assembly 4700. The first actuator 4800 is mounted to the actuator assembly 4700 via a first actuator support member 4801, the second actuator 4820 is mounted to the actuator assembly 4700 via a second actuator support member 4821, and the third actuator 4840 is mounted to the actuator assembly 4700 via a third actuator support member 4841. As described herein, the support members 4801, 4821, and 4841 may be any suitable support structure that secures the support member to the actuator assembly 4700 and enable the corresponding actuators to transmit rotation and or linear movement to one or more attached bands.

As shown in FIG. 13, the proximal portion 4421 of the first band 4420 is attached to the first actuator 4800 at a first location, and the proximal portion 4431 of the second band 4430 is attached to the first actuator 4800 at a second location different from the first location. Both the proximal portions 4421, 4431 can be attached to the first actuator 4800 via one or more fasteners as described herein. The proximal portion 4441 of the third band 4440 is attached to the third actuator 4840 at a first location, and the proximal portion 4451 of the fourth band 4450 is attached to the third actuator 4840 at a second location different from the first location. Both the proximal portions 4441, 4451 can be attached to the third actuator 4840 via one or more fasteners as described herein.

Operation of the first actuator 4800 coupled to the first band 4420 and the second band 4430 is similar to the operation of the first actuator 3800 coupled to the first band 3420 and the second band 3430, as described above with reference to FIGS. 8 and 9 (which in turn is similar to the operation of the first actuator 2800, the first band 2420 and the second band 2430 described above with reference to FIGS. 5 and 6). For example, movement produced by the first actuator 4800 about a first actuator axis $A_3$ in the direction of the arrow AA urges the first band 4420 to move in the direction of the arrow BB and urges the second band 4430 to move in the direction of the arrow CC, as shown in FIG. 13. The movement of the first band 4420 and the second band 4430 in turn urges the first pulley portion 4467 and first tool member 4462 to rotate relative to the wrist assembly 4500 about the second axis of rotation $A_2$ in the direction of the arrow KK. Conversely, rotation of the first actuator 4800 in the direction opposite of arrow AA urges the first pulley portion 4467 and first tool member 4462 to rotate in the direction opposite of the arrow KK in FIG. 12.

Operation of the third actuator 4840 coupled to the third band 4440 and the fourth band 4450 is similar to that of the third actuator 3840 on the third band 3440 and the fourth band 3450, as described above with reference to FIGS. 8 and 9. For example, movement produced by the third actuator 4840 about a third actuator axis $A_4$ in the direction of the arrow EE urges the second pulley portion 4477 and the second tool member 4472 to rotate relative to the wrist assembly 4500 about the second axis of rotation $A_2$ in the direction of the arrow KK. Conversely, rotation of the third actuator 4840 in the direction opposite of arrow EE urges the second pulley portion 4477 and second tool member 4472 to rotate in the direction opposite of the arrow KK in FIG. 12.

With reference to FIGS. 13-15, the second actuator 4820 includes a guide structure 4822 with a first guide surface 4823, a second guide surface 4824, a third guide surface 4825 and a fourth guide surface 4826. The first guide surface 4823 is in contact with the proximal portion 4421 of the first band 4420. The second guide surface 4824 is in contact with the proximal portion 4431 of the second band 4430. The third guide surface 4825 is in contact with the proximal portion 4441 of the third band 4440. The fourth guide surface 4826 is in contact with the proximal portion 4451 of the fourth band 4450. In some embodiments, each of the first, second, third, and fourth guide surfaces 4823, 4824, 4825, 4826 may be spaced from its respective band while the second actuator 4820 is in a neutral position prior to being actuated in either the direction of the arrow FF or the direction of the arrow GG, as shown in FIGS. 14 and 15. In some embodiments, the first guide surface 4823 and the second guide surface 4824 may be located on a first side of the guide structure 4822. The third guide surface 4825 and the fourth guide surface 4826 may be located on a second side of the guide structure 4822, opposite the first side. The first guide surface 4823 and the second guide surface 4824 may be spaced from each other in a longitudinal direction along a second actuator axis $A_5$. The third guide surface 4825 and the fourth guide surface 4826 may be spaced from each other in a longitudinal direction along a second actuator axis $A_5$.

In some embodiments, the second actuator 4820 can be a linear actuated mounted to the second actuator support member 4821 to translate in the directions of the arrows FF and GG as shown in FIGS. 14 and 15. Both the directions of the arrows FF and GG are non-parallel to the directions of travel indicated by the arrows BB and CC for the first band 4420, the second band 4430, the third band 4440, and the fourth band 4450.

The second actuator support member 4821 can be mounted to a base of the actuator assembly 4700, or can be secured to a track or guide of the actuator assembly 4700, to enable the first guide surface 4823 and the second guide surface 4824 to move in the directions of the arrows FF and GG shown in FIG. 13. In some embodiments, the second actuator 4820 can have a neutral position, as shown in FIG. 13, where the first guide surface 4823 and the second guide surface 4824 do not act on or contact any of the first, second, third, or fourth bands 4420, 4430, 4440, and 4450.

In a first active position of the second actuator 4820 as shown in FIG. 14, the first guide surface 4823 and the second guide surface 4824 of the second actuator 4820 are urged in the direction of the arrow FF, pressing against a proximal portion 4421 of the first band 4420 and a proximal portion 4431 of the second band 4430, respectively. When the first guide surface 4823 presses against the proximal portion 4421 and the second guide surface 4824 presses against the proximal portion 4431, length from both the first band 4420 and the second band 4430, external to the actuator assembly 4700, are taken up. As the lengths are taken up, the distal portion 4422 of the first band 4420 and the distal portion 4432 of the second band 4430 are moved in direction of the arrow CC. The movement of the distal portion 4422 and the distal portion 4432 in turn applies a force on the first pulley portion 4467 and urges the second link 4610 to rotate about the first axis of rotation $A_1$ in the direction of the arrow LL.

In a second active position of the second actuator 4820 as shown in FIG. 15, the third guide surface 4825 and the fourth guide surface 4826 of the second actuator 4820 are urged in the direction of the arrow GG, pressing against a proximal portion 4441 of the third band 4440 and a proximal portion 4451 of the fourth band 4450. When the third guide surface 4825 presses against the proximal portion 4441 and the fourth guide surface 4826 presses against the proximal portion 4451, length from both the third band 4440 and the fourth band 4450, external to the actuator assembly 4700, are taken up. As the lengths are taken up, the distal portion 4442 of the third band 4440 and the distal portion 4452 of the fourth band 4450 are moved in direction of the arrow CC. The movement of the distal portion 4442 and the distal portion 4452 in turn applies a force on second first pulley portion 4477 and urges the second link 4610 to rotate about the first axis of rotation $A_1$ in the direction opposite of the arrow LL.

By alternating actuation between the first active position and the second active position of the second actuator 4820, the second link 4610 is operable to pivot back and forth about the first axis of rotation $A_1$ (e.g., pitch, the term pitch is arbitrary). Thus, the combination of three actuators (the first, second and third actuators 4800, 4820, 4840), a first set of bands (the first and second bands 4420, 4430) and a second set of bands (the third and fourth bands 4440, 4450) are operable to control the end effector 4460 and the wrist assembly 4500 of instrument 4400 with at least 3 DOFs (e.g., pitch, yaw, and grip).

FIGS. 16-31 are various views of an instrument 5400, according to an embodiment. In some embodiments, the instrument 5400 or any of the components therein are optionally parts of a surgical assembly that performs minimally invasive surgical procedures, and which can include a patient-side teleoperated manipulator unit, one or more kinematic linkages, one or more cannulas, or the like. For example, the instrument 5400 may be coupled to and operable with a MIRS system, such as the MIRS system 1000 described with reference to FIGS. 1-4 above. The instrument 5400 includes an actuator assembly 5700 (which functions as a transmission or backend mechanism), a shaft 5410, a wrist assembly 5500, and an end effector 5460. The instrument 5400 also includes a first band 5420, a second band 5430, a third band 5440, and a fourth band 5450 that couple the actuator assembly 5700 to the wrist assembly 5500. The wrist assembly 5500 can be similar to any of the wrist assemblies shown and described herein. The end effector 5460 can include any suitable tool member and can be similar to any of the end effectors described herein. For example, the end effector can include a first tool member 5462 and second tool member 5472 which form a pair of graspers. The first tool member 5462 can include a contact portion 5464 and a pulley portion 5467. Similarly, the second tool member 5472 can include a contact portion 5474 and a pulley portion 5477.

The shaft 5410 can be any suitable elongated shaft that couples the wrist assembly 5500 to the actuator assembly 5700. Specifically, the shaft 5410 includes a proximal end 5411 that is coupled to the actuator assembly 5700, and a distal end 5412 that is coupled to the wrist assembly 5500 (e.g., a proximal link of the wrist assembly 5500, similar to the proximal or first link 2510, 3510, 4510 described above). The shaft 5410 defines a lumen 5413 (see FIG. 30) or multiple passageways through which the bands and other components (e.g., electrical wires, ground wires, or the like) can be routed from the actuator assembly 5700 to the wrist assembly 5500. The instrument 5400 is configured such that movement of the bands can produce rotation of the wrist assembly 5500 about a joint axis $A_{11}$ (e.g., similar to rotation about the pitch axis $A_1$ described above), rotation of the end effector 5460 about an axis of rotation $A_{12}$ (e.g., similar to rotation about the axis $A_2$ described above, also referred to as the yaw axis), grip rotation of the tool members of the end effector 5460 about the axis $A_{12}$, or any combination of these movements. Changing the pitch, yaw, or grip of the instrument 5400 can be performed by manipulating the bands within the actuator assembly 5700.

Figure 20:
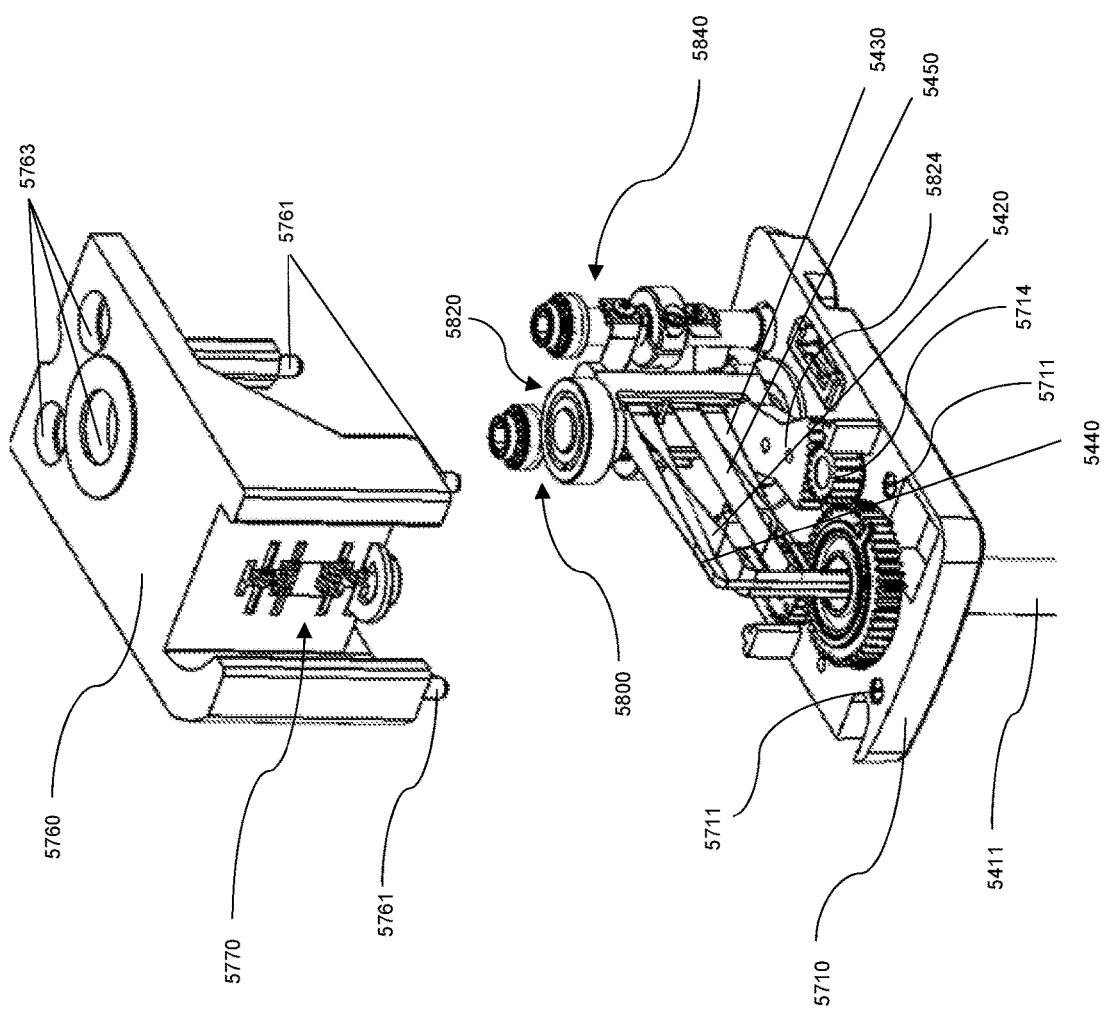
FIG. 20 is a perspective exploded view of the actuator assembly in FIG. 18, showing a housing and guide assembly removed from a base of the actuator assembly.
Figure 24:
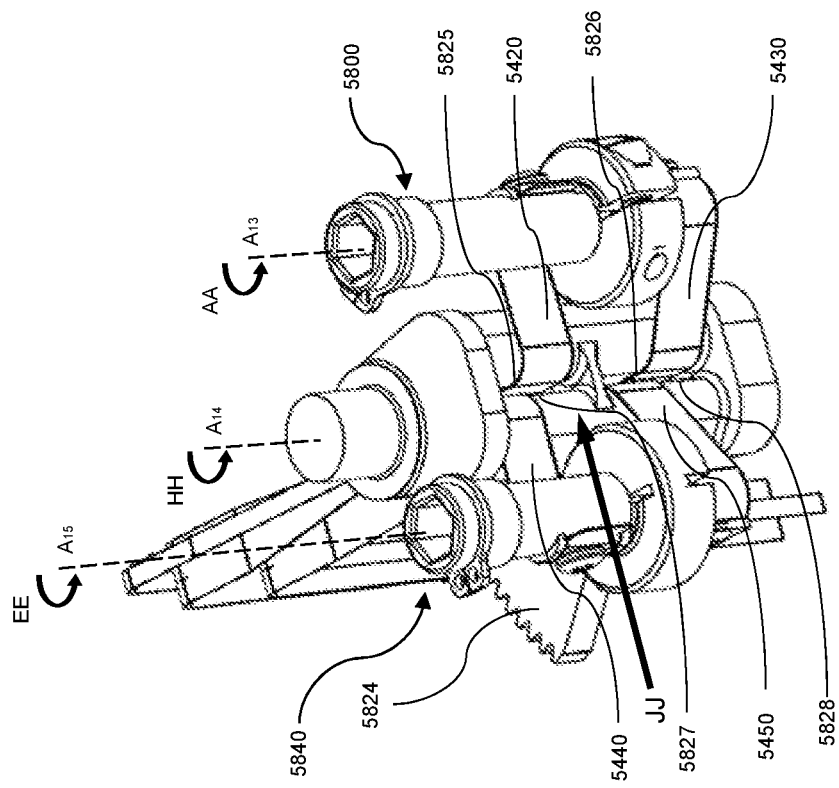
FIGS. 23 and 24 are a front perspective view (FIG. 23) and a rear perspective view (FIG. 24) of the actuators and bands of the actuator assembly in FIG. 20.
Figure 26:
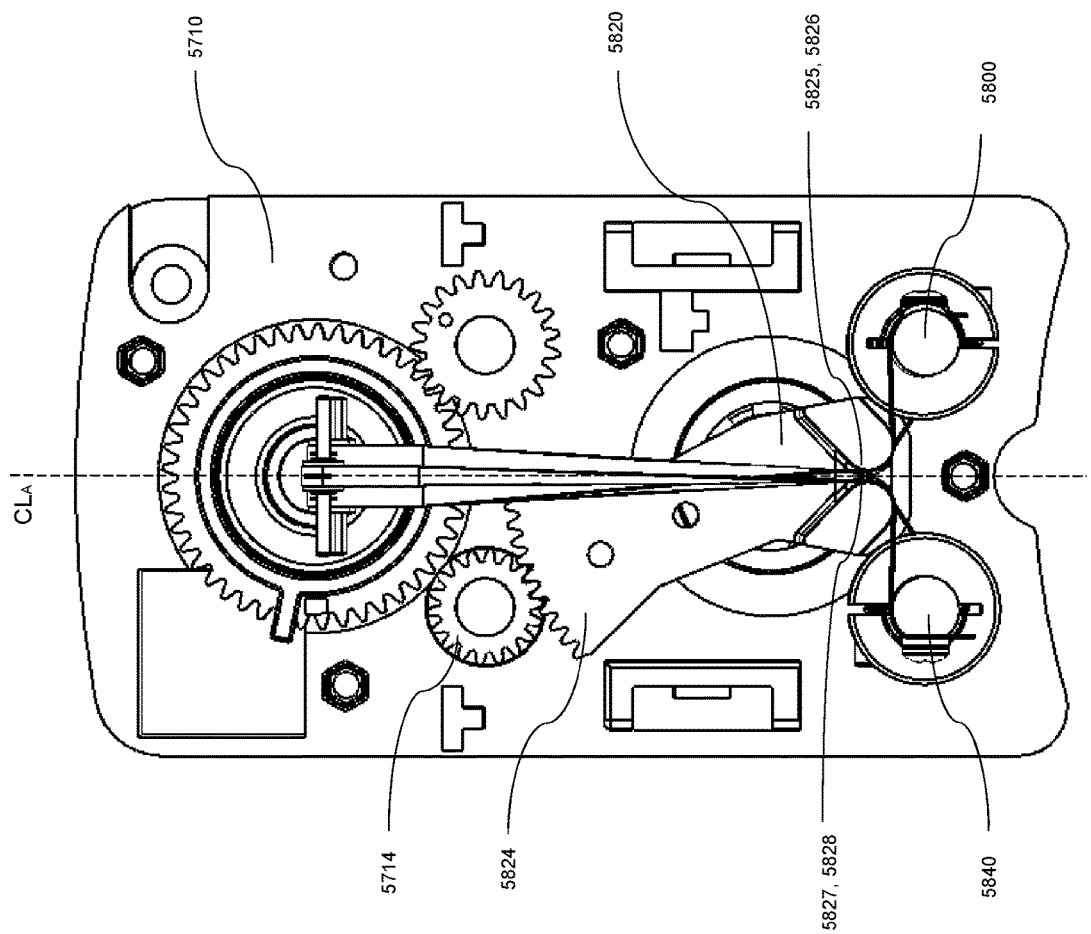
FIG. 26 is a cross-sectional view of a portion of the actuator assembly in FIG. 18 when the second actuator is in a first position, the cross-section taken along line $X_1$-$X_1$ in FIG. 18.
Figure 27:
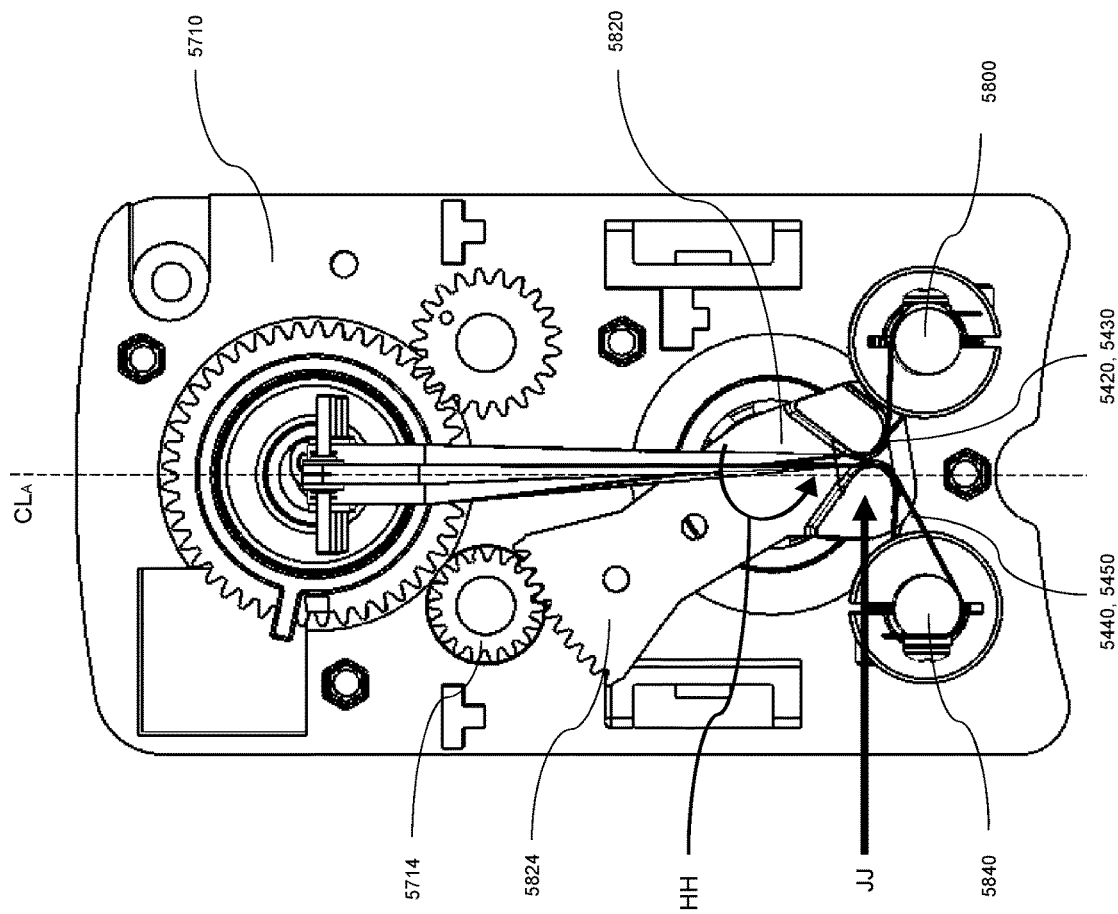
FIG. 27 is a cross-sectional view of a portion of the actuator assembly in FIG. 18 when the second actuator is in a second position, the cross-section taken along line $X_1$-$X_1$ in FIG. 18.

The actuator assembly 5700 includes a base 5710 and a housing 5760, and the housing 5760 can be attached to the base 5710 via one or more fastening members. For example as shown in FIG. 20, the fastening members can be a combination of pins 5761 and mounting holes 5711, however, any suitable fastener can be used to secure the housing 5760 to the base 5710. In some embodiments, the base 5710 and housing 5760 may partially enclose or fully enclose components disposed within the actuator assembly 5700. The base 5710 and the housing 5760 provide structural support for mounting and aligning components in the actuator assembly 5700. For example, referring to FIG. 30, the base 5710 defines a shaft opening 5712 within which a proximal end 5411 of the shaft 5410 is mounted. The base 5710 further defines one or more bearing surfaces or openings 5713 within which the actuators are mounted and rotatably supported. In some embodiments, the housing 5760 includes one more bearing surfaces or openings 5763 within which the actuators are mounted. The openings 5763 of the housing 5760 can be axially aligned with the openings 5713 of the base. Referring to FIGS. 26 and 27, the actuator assembly 5700 defines an assembly center line $CL_A$ that bisects the actuator assembly 5700 into two sides. The assembly center line $CL_A$ extends from the center line of the shaft opening 5712 and center line of the opening 5713 within which the first mounting portion of the second actuator 5820 is mounted (as described below). Similarly stated the assembly center line $CL_A$ is coplanar with the center line of the shaft opening 5412 and the central rotational axis $A_{14}$ of the second actuator 5820. As described in more detail herein, in certain operating conditions, the center line of the bands is coincident with the assembly center line $CL_A$, while in other operating conditions, the center line of the bands is slightly offset from (or nonparallel to) the assembly center line $CL_A$.

In addition to providing mounting support for the internal components of the actuator assembly 5700, the base 5710 can include external features (e.g., recesses, clips, etc.) that interface with a docking port of a drive device (not shown). The drive device can be, for example, a handheld system or a computer-assisted teleoperated system that can receive the instrument 5400 and manipulate the instrument 5400 to perform various surgical operations. The drive device can include one or more motors to drive actuators of the actuator assembly 5700. In other embodiments, the drive device can be an assembly that can receive and manipulate the instrument 5400 to perform various operations.

Specifically, referring to FIGS. 18-24, the actuator assembly 5700 includes a first actuator 5800, a second actuator 5820, and a third actuator 5840. Each of the first, second and third actuators 5800, 5820, 5840 are rotatably supported within a corresponding opening, such as opening 5713 of the base 5710 (shown in FIG. 30), and within a corresponding opening 5763 of the housing 5760. Each of the first, second and third actuators 5800, 5820, 5840 can be driven by a corresponding motor in the drive device. For example, the first actuator 5800 can be driven to rotate about a first actuator axis $A_{13}$, the second actuator 5820 can be driven to rotate about a second actuator axis $A_{14}$ (also referred to as a central rotational axis), and the third actuator 5840 can be driven to rotate about a third actuator axis $A_{15}$.

Figure 25B:
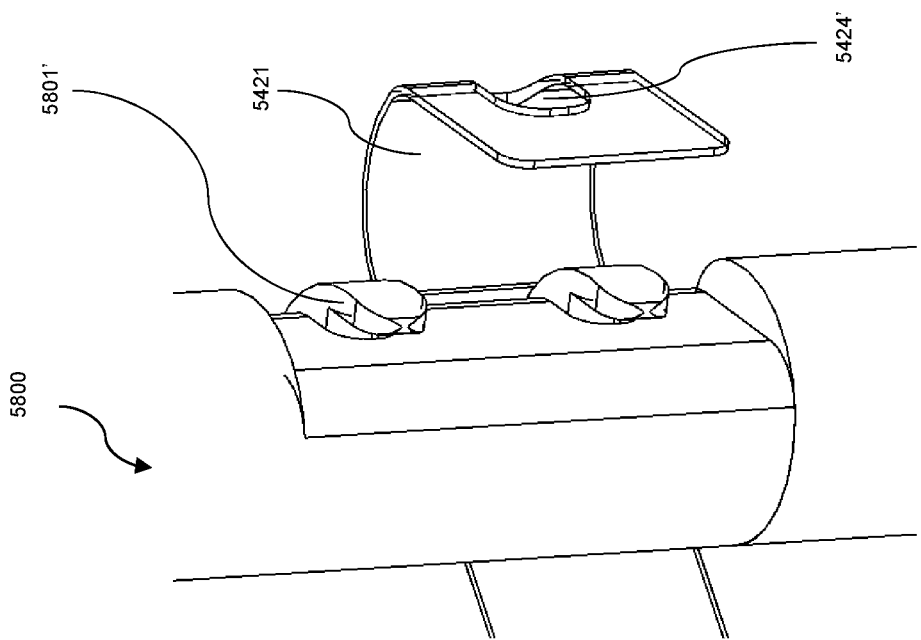
FIG. 25b is a perspective exploded view of a first band attached to a first actuator of the actuator assembly in FIG. 23 in accordance with another embodiment.
Figure 25A:
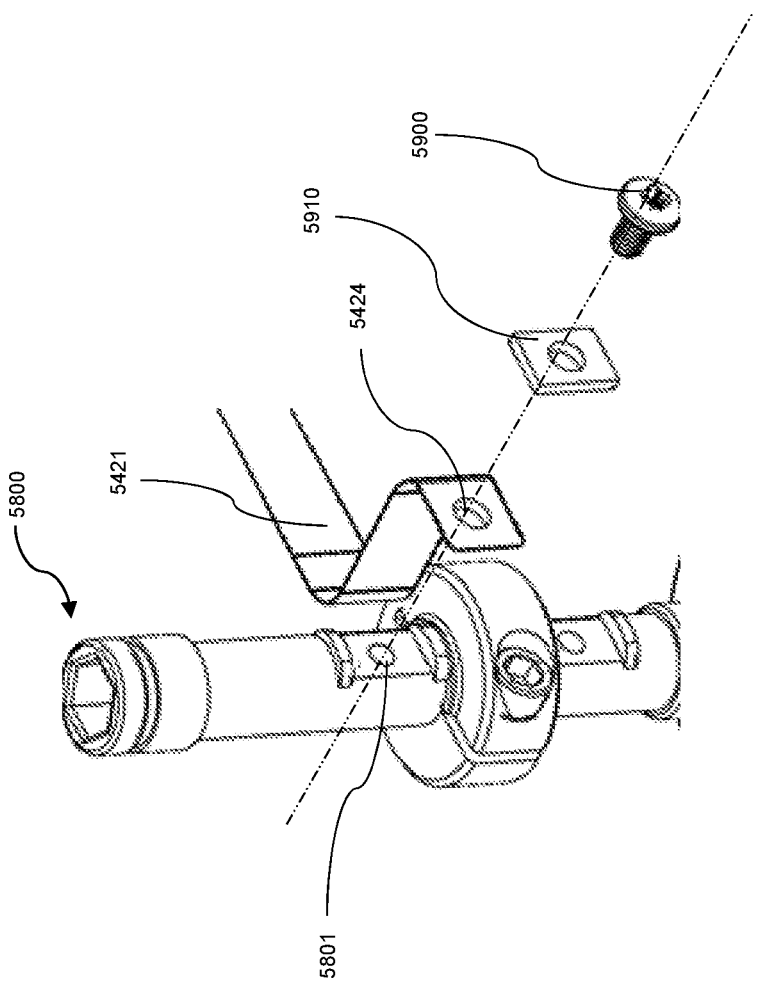
FIG. 25a is a perspective exploded view of a first band attached to a first actuator of the actuator assembly in FIG. 23 in accordance with an embodiment.

As shown in FIGS. 23-25b and 30, the first actuator 5800 includes a shaft about which a first end portion 5421 of a first band 5420 and a first end portion 5431 of a second band 5430 are wrapped. In this manner, the first band 5420 extends tangentially from one side of the first actuator 5800 and the second band 5430 extends tangentially from another side of the first actuator 5800, as shown in greater detail in FIG. 24, for example. The first end portions of the first band 5420 and the second band 5430 are secured to the first actuator 5800 via a fastener mechanism. Specifically, as shown in FIG. 25a, the first end portion 5421 of the first band 5420 includes a through hole 5424 for receiving a fastener 5900. The shaft of the first actuator 5800 can include a threaded mounting hole 5801. The fastener 5900 is inserted through the through hole 5424 and threaded into the threaded mounting hole 5801 to secure the first band 5420 to the first actuator 5800. A washer 5910 can optionally be interposed between the fastener 5900 and the first end portion 5421 to improve contact between the fastener 5900 and the first band 5420. In some embodiments, as shown in FIG. 25b, the shaft of the first actuator 5800 can include a hook portion 5801' and the first end portion 5421 can include a corresponding pocket or opening 5424' for receiving the hook portion 5801'. Although the first band 5420 and the second band 5430 are shown as being coupled to the first actuator 5800 using a mechanical fastener, in other embodiments, any suitable mechanism for fastening the first band 5420 and the second band 5430 to the first actuator 5800 (or the third band 5440 and the fourth band 5450 to the third actuator 5840) can be used. For example, in some embodiments, the bands can be coupled to their respective actuator via an adhesive, via a weld, or by having protrusions that form an interference fit with a mating opening defined by the actuator.

The first band 5420 and the second band 5430 are coupled to the pulley portion 5467 to control the first tool member 5462. Specifically, the first and second bands 5420, 5430 are routed from the first actuator 5800 through the second actuator 5820 and over a guide member 5770 of the housing 5760. As described in more detail herein, the guide member 5770 redirects a longitudinal center line of the first and second bands 5420, 5430 such that a central portion 5423 of the first band 5420 and a central portion 5433 of the second band 5430 are directed into an opening at the proximal end 5411 of the shaft 5410. Specifically, referring to FIG. 30, the longitudinal center line $CL_1$ of the first band 5420 and the longitudinal center line of the second band 5430 (not identified in FIG. 30 to maintain clarity, but similar to that shown for the first band 5420) are redirected by the guide member 5770 by an angle of about ninety degrees. Although the amount of change in direction (or "bend") of the bands is shown as being ninety degrees, in other embodiments, the guide member can redirect the longitudinal center line of the first and second bands 5420, 5430 by any suitable bend angle, such as, for example, by a bend angle of between 45 degrees and 135 degrees, by a bend angle of between 60 degrees and 120 degrees, or a bend angle of between 75 degrees and 105 degrees.

The first and second bands 5420, 5430 extend through a lumen 5413 of the shaft 5410 from the proximal end 5411 to the distal end 5412 substantially parallel with a longitudinal axis of the shaft 5410. From the distal end 5412 of the shaft 5410, a second end portion 5422 of the first band 5420 and a second end portion 5432 of the second band 5430 are routed through the wrist assembly 5500 and are attached to the pulley portion 5467 of the first tool member 5462, as shown in generally detail in FIG. 17, for example. In this manner, the first actuator 5800 is operable rotate about the first actuator axis $A_{13}$ to urge the first and second bands 5420, 5430 to actuate the first tool member 5462 about the axis $A_{12}$ (similar to the transfer of motion from of the first and second bands 4420, 4430 on first tool member 4462 discussed above). For example, rotation of the first actuator 5800 about the axis $A_{13}$ in the direction of arrow AA urges the first tool member 5462 to rotate about the axis $A_{12}$ in the direction of the arrow KK.

The third actuator 5840 includes a shaft about which a first end portion 5441 of a third band 5440 and a first end portion 5451 of a fourth band 5450 are wrapped. In this manner, the third band 5440 extends tangentially from one side of the third actuator 5840 and the fourth band 5450 extends tangentially from another side of the third actuator 5840, as shown in greater detail in FIG. 24, for example. The first end portions of the third band 5440 and the fourth band 5450 are secured to the third actuator 5840 via a fastener mechanism, as shown and described above with respect to the connection of the first and second bands 5420, 5430 to the first actuator 5800. The third band 5440 and the fourth band 5450 are coupled to the pulley portion 5477 to control the second tool member 5472. Specifically, the third and fourth bands 5440, 5450 are routed from the third actuator 5840 through the second actuator 5820 and over the guide member 5770 of the housing 5760. The guide member 5770 redirects a longitudinal center line of the third and fourth bands 5440, 5450 such that a central portion 5443 of the third band 5440 and a central portion 5453 of the fourth band 5450 are directed into an opening at the proximal end 5411 of the shaft 5410. Specifically, referring to FIG. 30, the longitudinal center line $CL_3$ of the third band 5440 and the longitudinal center line of the fourth band 5450 (not identified in FIG. 30 to maintain clarity, but similar to that shown for the third band 5440) are redirected by the guide member 5770 by an angle of about ninety degrees. Although the amount of change in direction (or "bend") of the bands is shown as being ninety degrees, in other embodiments, the guide member can redirect the longitudinal center line of the third and fourth bands 5440, 5450 by any suitable bend angle, such as, for example, by a bend angle of between 45 degrees and 135 degrees, by a bend angle of between 60 degrees and 120 degrees, or a bend angle of between 75 degrees and 105 degrees The third and fourth bands 5440, 5450 extend through the lumen 5413 from the proximal end 5411 to the distal end 5412 substantially parallel with the longitudinal axis of the shaft 5410. From the distal end 5412, a second end portion 5442 of the third band 5440 and a second end portion 5452 of the fourth band 5450 are routed through the wrist assembly 5500 and are attached to the pulley portion 5477 of the second tool member 5472. In this manner, the third actuator 5840 is operable rotate about the third actuator axis $A_{15}$ to urge the third and fourth bands 5440, 5450 to actuate the second tool member 5472 about the axis $A_{12}$ (similar to the transfer of motion from of the third and fourth bands 4440, 4450 on second tool member 4472). For example, rotation of the third actuator 5840 about the axis $A_{15}$ in the direction of arrow EE urges the second tool member 5472 to rotate about the axis $A_{12}$ in the direction of the arrow KK. Together, the first and third actuators 5800, 5840 can be actuated such that the first and second tool members 5462, 5472 can rotate together about the axis $A_{12}$ to control yaw, or in opposition to one another to control grip of the first and second tool members 5462, 5472. Thus, the first and third actuators 5800, 5840 and the two pair of bands 5420, 5430, 5440, 5450 can be operated to control two degrees of freedom (i.e., grip and yaw).

With reference to FIGS. 19-24 and 26-27, the second actuator 5820 (which functions as a length conservation member) includes a first mounting portion 5822, a second mounting portion 5823, a guide structure 5821, and a sector gear 5824. The first mounting portion 5822 is configured to be rotatably supported by one of the openings 5713 of the base 5710. The second mounting portion 5823 is configured to be rotatably supported by one of the openings 5763 of the housing. Both the first and second mounting portions 5822, 5823 extend along the central rotational axis $A_{14}$ of the second actuator 5820. The second actuator 5820 can be driven via the drive device (not shown) to rotate about the central rotational axis $A_{14}$ relative to the base 5710 and the housing 5760. Specifically, sector gear 5824 of the second actuator 5820 is meshed with a drive gear 5714, which in turn can be coupled to a motor of the drive device. In this manner, rotation of the drive gear 5714 urges the second actuator 5820 to be rotated about the central rotational axis $A_{14}$.

The guide structure 5821 of the second actuator 5820 includes a first guide structure axis $A_{15}$ and a second guide structure axis $A_{16}$, the second guide structure axis $A_{16}$ being parallel with and laterally spaced part from the first guide structure axis $A_{15}$. Both the first and second guide structure axes $A_{15}$, $A_{16}$ are parallel with and equally spaced from the central rotational axis $A_{14}$. In other embodiments, however, the first guide structure axis $A_{15}$ can be nonparallel to the second guide structure axis $A_{16}$ and the first and second guide structure axes $A_{15}$, $A_{16}$ can be unequally spaced from the central rotational axis $A_{14}$. The guide structure 5821 includes at least a first guide surface 5825, a second guide surface 5826, a third guide surface 5827, and a fourth guide surface 5828. The first and second guide surfaces 5825, 5826 extend along the first guide structure axis $A_{15}$, while the third and fourth guide surfaces 5827, 5828 extend along the second guide structure axis $A_{16}$. The first guide surface 5825 defines a first width and the second guide surface 5826 defines a second width, the first width and the second width being spaced apart from one another along the first guide structure axis $A_{15}$. The third guide surface 5827 defines a third width and the fourth guide surface 5828 defines a fourth width, the third width and the fourth width being spaced apart from one another along the second guide structure axis $A_{16}$.

The first guide surface 5825 and the third guide surface 5827 define a first band opening 5831 therebetween. Similarly stated, a first band opening 5831 is defined between the first guide surface 5825 and the third guide surface 5827. In use, the first end portion 5421 of the first band 5420 may contact and slide along the first guide surface 5825 as it passes through the first band opening 5831 of the second actuator 5820, and the first end portion 5441 of the third band 5440 may contact and slide along the third guide surface 5827 as it passes through the first band opening 5831 of the second actuator 5820. The second guide surface 5826 and the fourth guide surface 5828 define a second band opening 5832 therebetween. Similarly stated, a second band opening 5832 is defined between the second guide surface 5826 and the fourth guide surface 5828. In use, the first end portion 5431 of the second band 5430 may contact and slide along the second guide surface 5826 as it passes through the band opening 5832 of the second actuator 5820, and the first end portion 5451 of the fourth band 5450 may contact and slide along the fourth guide surface 5828 as it passes through the second band opening 5832 of the second actuator 5820.

In some embodiments, the first and second guide surfaces 5825, 5826 can include a rounded or curved surface defined by a radius extending from the first guide structure axis $A_{15}$. The third and fourth guide surfaces 5827, 5828 can include a rounded or curved surface defined by a radius extending from the second guide structure axis $A_{16}$. By providing rounded or curved surfaces, wear and friction of the bands 5420, 5430, 5440, 5450 can be reduced as the bands 5420, 5430, 5440, 5450 pass through the band openings or are acted on by the guide structure 5821 and corresponding guide surfaces, thus improving longevity of the components. While the first guide surface 5825 and the second guide surface 5826 are illustrated as fixed surfaces relative to the first guide structure axis $A_{15}$, and the third guide surface 5827 and the fourth guide surface 5828 are illustrated as fixed surfaces relative to the second guide structure axis $A_{16}$, in some embodiments one or more of the first, second, third or fourth guide surfaces 5825, 5826, 5827, 5828 may be rotatable relative to the first guide structure axis $A_{15}$ or the second guide structure axis $A_{16}$. For example, one or more of the first, second, third or fourth guide surfaces may be formed as a pulley member rotatable about the first guide structure axis $A_{15}$ or the second guide structure axis $A_{16}$ to further reduce friction of the bands passing through the second actuator 5820.

As shown, the guide structure 5821 includes a bridge portion 5829 extending between the first guide structure axis $A_{15}$ to the second guide structure axis $A_{16}$ from a location between the first and second guide surfaces 5825, 5826 to a location between the third and fourth guide surfaces 5827, 5828. Thus, the bridge portion 5829 separates the first band opening 5831 and the second band opening 5832. In this manner, the bridge portion 5829 can maintain spacing and improve rigidity and stability of the first, second, third, and fourth guide surfaces 5825, 5826, 5827, 5828 during operation of the second actuator 5820 and the bands 5420, 5430, 5440, 5450. In some embodiments, the first, second, third, and fourth guide surfaces 5825, 5826, 5827, 5828 can be formed monolithically with the second actuator 5820. In some embodiments, the bridge portion 5829 can also be formed monolithically with the second actuator 5820. In yet other embodiments, the second actuator 5820 need not include a bridge portion, and the first band opening 5831 can be continuous with the second band opening 5832. Similarly stated, in some embodiments, the second actuator 5820 defines a single opening through which all of the bands can be moved.

With reference to FIGS. 19, 21-24, and 26-27, the sector gear 5824 of the second actuator 5820 can be driven by the drive gear 5714 to rotate about central rotational axis $A_{14}$ in the direction of the arrow HH. Because of the second guide structure axis $A_{16}$ is offset from the central rotational axis $A_{14}$, the third and fourth guide surfaces 5827, 5828 are actuated generally in the direction of the arrow JJ, as shown for example in FIG. 27. In this manner, the third and fourth guide surfaces 5827, 5828 move laterally from one side of the assembly center line $CL_A$ to the other, increasing the travel path of the third and fourth bands 5440, 5450 exiting the actuator assembly 5700. Simultaneously, the first and second guide surfaces 5825, 5826 are actuated generally in the direction of the arrow JJ to move away from the assembly center line $CL_A$, decreasing the travel path of the first and second bands 5420, 5430 exiting the actuator assembly 5700. By increasing the travel path of the third and fourth bands 5440, 5450 and decreasing the travel path of the first and second bands 5420, 5430 within the actuator assembly 5700, length of the third and fourth bands 5440, 5450 is effectively taken up from the outside the actuator assembly 5700 while length of the first and second bands 5420, 5430 is released to outside the actuator assembly 5700. In this manner, movement of the first, second, third and fourth bands 5420, 5430, 5440, 5450 urges the wrist assembly 5500 to rotate about the axis $A_{11}$ in the direction of the arrow LL to achieve a third degree of freedom (i.e., pitch, the term pitch is arbitrary). As will be appreciated by one skilled in the art, rotation of the second actuator 5820 in the direction opposite of the arrow HH would have the effect of increasing the travel path of the first and second bands 5420, 5430 while reducing the travel path of the third and fourth bands 5440, 5450, thereby urging the wrist assembly 5500 to rotate about the axis $A_{11}$ in the direction opposite of the arrow LL.

With reference to FIGS. 18-20, 23-24 and 28-31, the housing 5760 includes the guide member 5770 for redirecting and aligning the bands 5420, 5430, 5440, 5450 entering and exiting the actuator assembly 5700. In some embodiments, to achieve actuation about three degrees of freedom using only two pairs of bands 5420, 5430, 5440, 5450, as described above, the bands 5420, 5430, 5440, 5450 can be arranged to travel in a direction generally perpendicular to the longitudinal axis of the shaft 5410. Further, to enable the travel path of the bands to be altered by the guide structure 5821 of the second actuator 5820, the bands 5420, 5430, 5440, 5450 may initially be spaced apart while traveling through the second actuator 5820. However, due to the space constraints and reduced instrument shaft diameter required for minimally invasive procedures, it is advantageous for the bands to be redirected and guided through the lumen 5413 of the shaft 5410 in a compact manner. As described herein, the actuator assembly 5700 and the guide member 5770 facilitate redirecting the bands through a bend angle such that the longitudinal center line (e.g., the longitudinal center line $CL_1$ of the first band 5420) of each band can be routed into the lumen 5413 of the shaft. The actuator assembly 5700 and the guide member 5770 are also configured to position the bands to enter the shaft 5410 at a desired location. Specifically, the guide member 5770 is configured such that the portion of the first band 5420 that bends is positioned at a first height $h_1$ above the opening into the lumen 5413 of the shaft 5410 and the portion of the second band 5430 that bends is positioned at a second height $h_2$ above the opening into the lumen 5413 of the shaft 5410, where the second height $h_2$ is different than the first height $h_1$ (see, e.g., FIG. 31). Additionally, the guide member 5770 is configured such that the bands can be spaced apart about the longitudinal center line of the shaft 5410. In this manner, the first band 5420, the second band 5430, the third band 5440, and the fourth band 5450 can be routed into the desired position within the shaft lumen 5413. Specifically, the bands can be positioned within the shaft passageway spaced apart from the shaft center line and at different radial or circumferential positions within the shaft passageway. This arrangement can prevent frictional contact of adjacent bands and reduce the likelihood that the bands will become entangled with each other within shaft 5410. Although the guide member 5770 is shown as performing each of these routing (or redirecting) functions, in other embodiments, a guide member can include structure and/or can perform only a subset of these functions.

Figure 28:
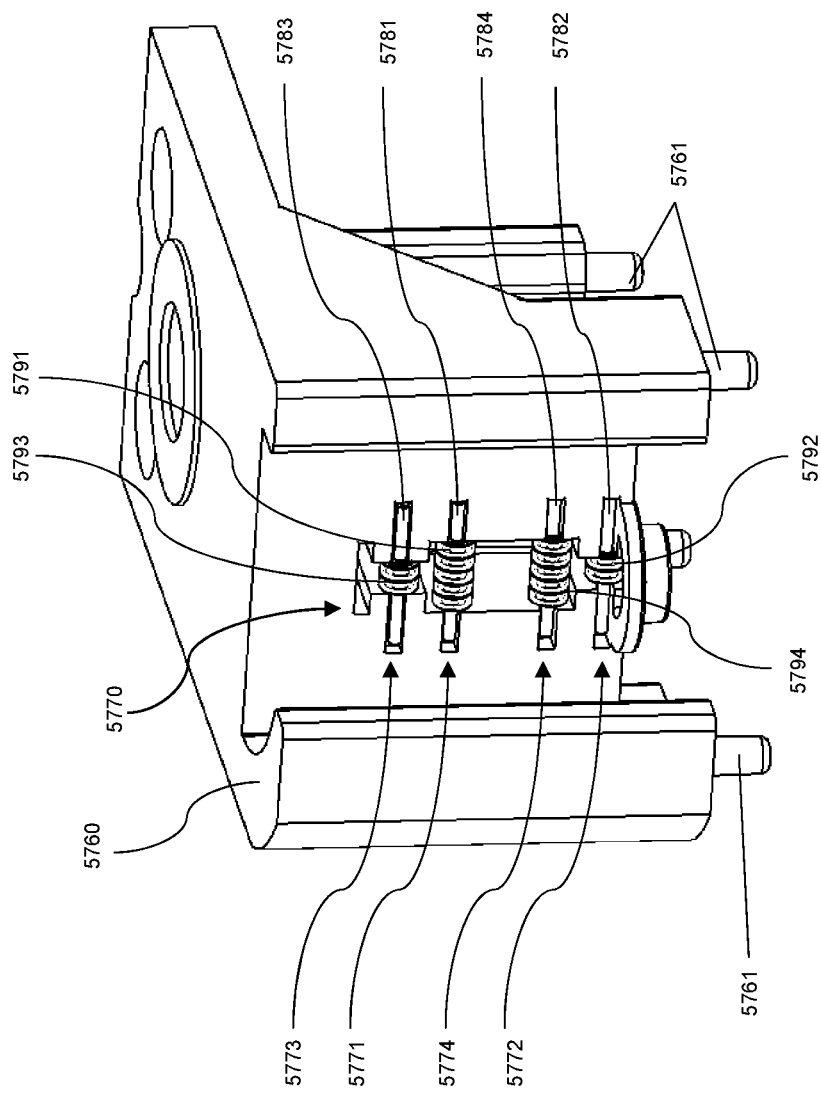
FIG. 28 is an enlarged perspective view of the housing as shown in FIG. 20.
Figure 29:
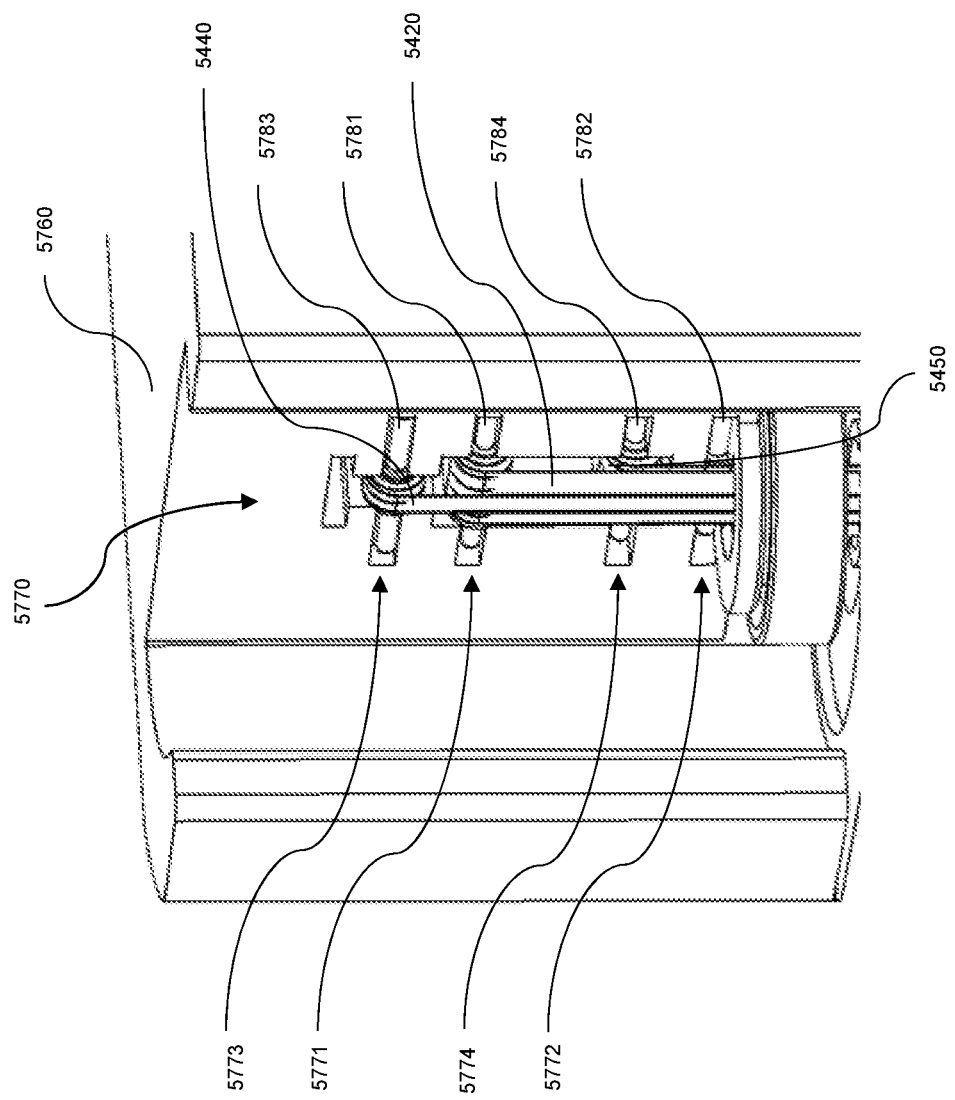
FIG. 29 is an enlarged perspective view of the housing coupled to the device, as shown in FIG. 18.

Referring to FIG. 28, the guide member 5770 includes a first guide element 5771, a second guide element 5772, a third guide element 5773, and a fourth guide element 5774. Each of the first, second, third and fourth guide elements 5771, 5772, 5773, 5774 can be sized to accommodate at least a width of a respective band passing through the guide member 5770. The first guide element 5771 can include a first support pin 5781 and one or more first bearings 5791 for guiding and redirecting the first band 5420 between the actuator assembly 5700 and the shaft 5410. The second guide element 5772 can include a second support pin 5782 and one or more second bearings 5792 for guiding and redirecting the second band 5430. The third guide element 5773 can include a third support pin 5783 and one or more third bearings 5793 for guiding and redirecting the third band 5440. The fourth guide element 5774 can include a third support pin 5784 and one or more fourth bearings 5794 for guiding and redirecting the fourth band 5450. Each of the pins can be fixedly or rotatably mounted to the housing 5760. For example, the pins 5781, 5782, 5783, 5784 can be secured to the housing via friction fit, a removable cover member, and/or one or more fastening members. Each of the bearings 5791, 5792, 5793, 5794 are operable to rotate independently. For example, the bearing 5791 may be operable to rotate in a first direction when the bearing 5792 rotates in a second direction, opposite the first direction, when the first actuator 5800 feeds out length of the first band 5420 while taking up length of the second band 5430.

The bearings can be any type of suitable bearings for the bands 5420, 5430, 5440, 5450 to partially wrap around to slide over or roll with the bearings. For example, the bearings can be one or more of bushings, ball bearings, needle bearings, etc. In some embodiments, the pin and bearings arrangement can be substituted with a fixed rounded member with a smooth or reduced-friction surface for the bands 5420, 5430, 5440, 5450 through the guide member 5770. For example, the fixed rounded member can include a surface treated with Polytetrafluoroethylene (PTFE) or other anti-friction coatings. In some embodiments, each of the guide members 5771, 5772, 5773, 5774 may include two or more bearings 5791, 5792, 5793, 5794 to provide even distribution of support and facilitate rotation motion, particularly given the small sizes involved. For example, the first guide member 5771 can have four bearings 5791 and the second guide member 5772 can have two bearings 5792 where a width of the first band 5420 is larger than a width of the second band 5430.

Figure 30:
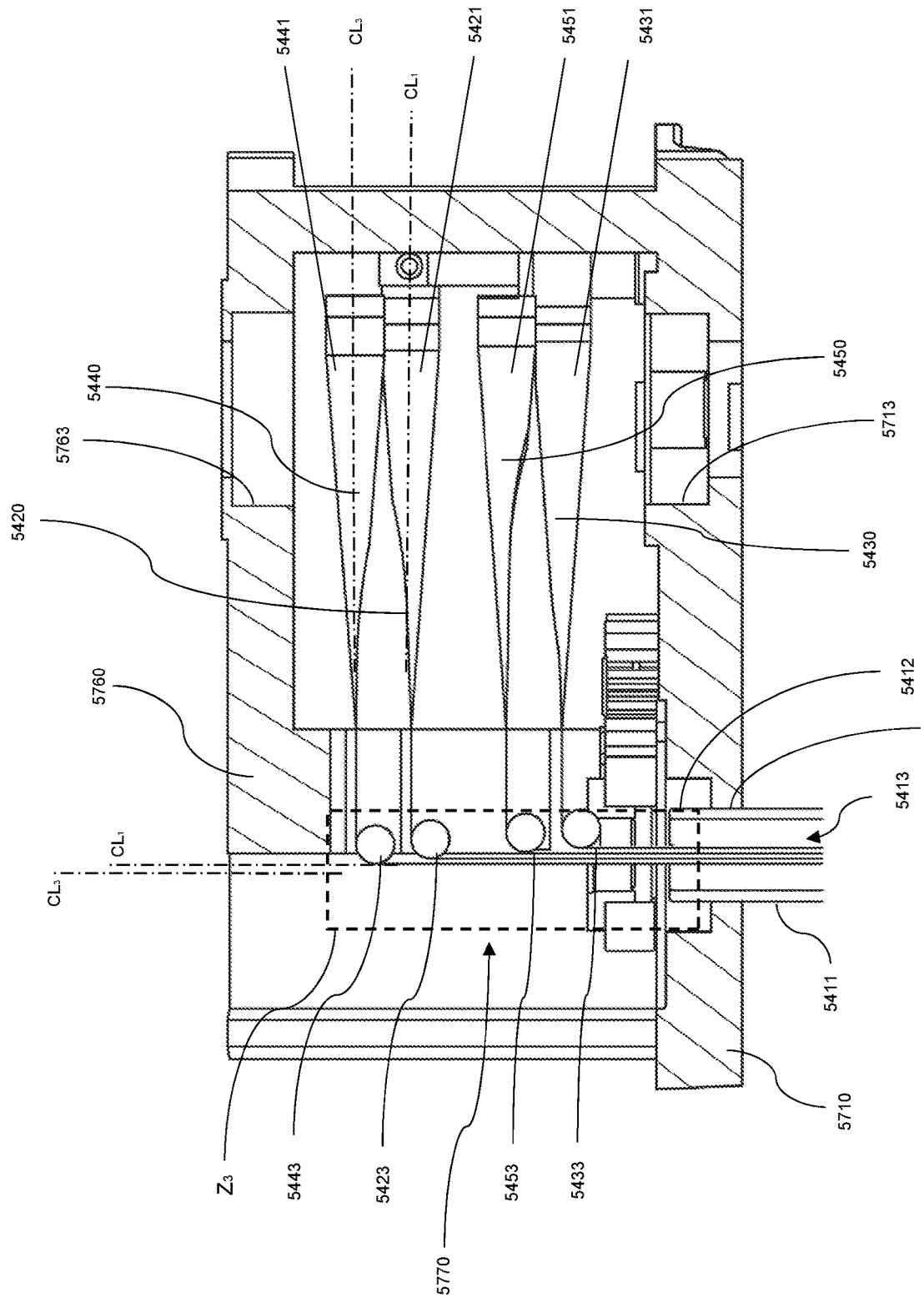
FIG. 30 is a cross-sectional view of a portion of the actuator assembly, the cross-section taken along line $X_2$-$X_2$ in FIG. 18.

As shown in FIGS. 19, 20, 23, 24, and 30, each of the bands 5420, 5430, 5440, 5450 generally travels in a direction along the length (i.e., along the assembly center line $CL_A$ shown in FIGS. 26 and 27) of the housing 5760 from either the first actuator 5800 or the third actuator 5840 to the guide member 5770. As the bands 5420, 5430, 5440, 5450 pass through the guide structure 5821 of the second actuator 5820, a width of each of the bands 5420, 5430, 5440, 5450 is oriented in a vertical direction parallel to the central rotational axis $A_{14}$. In some embodiments, the widths of each of the bands 5420, 5430, 5440, 5450 are each spaced apart from one another relative to the central rotational axis $A_{14}$. Similarly stated, as shown in FIG. 30, the longitudinal center line of each band is offset from the longitudinal center line of the other bands along the central rotational axis $A_{14}$. Similarly, each of the guide elements 5771, 5772, 5773, 5774 is spaced apart from one another relative to the central rotational axis $A_{14}$. For example, the first guide element 5771 is at a first axial distance (i.e., along the center line of the shaft 5410) from the proximal end portion 5411 of the shaft 5410 and the second guide element 5772 is at a second, different axial distance from the proximal end portion 5411 of the shaft 5410.

Figure 19:
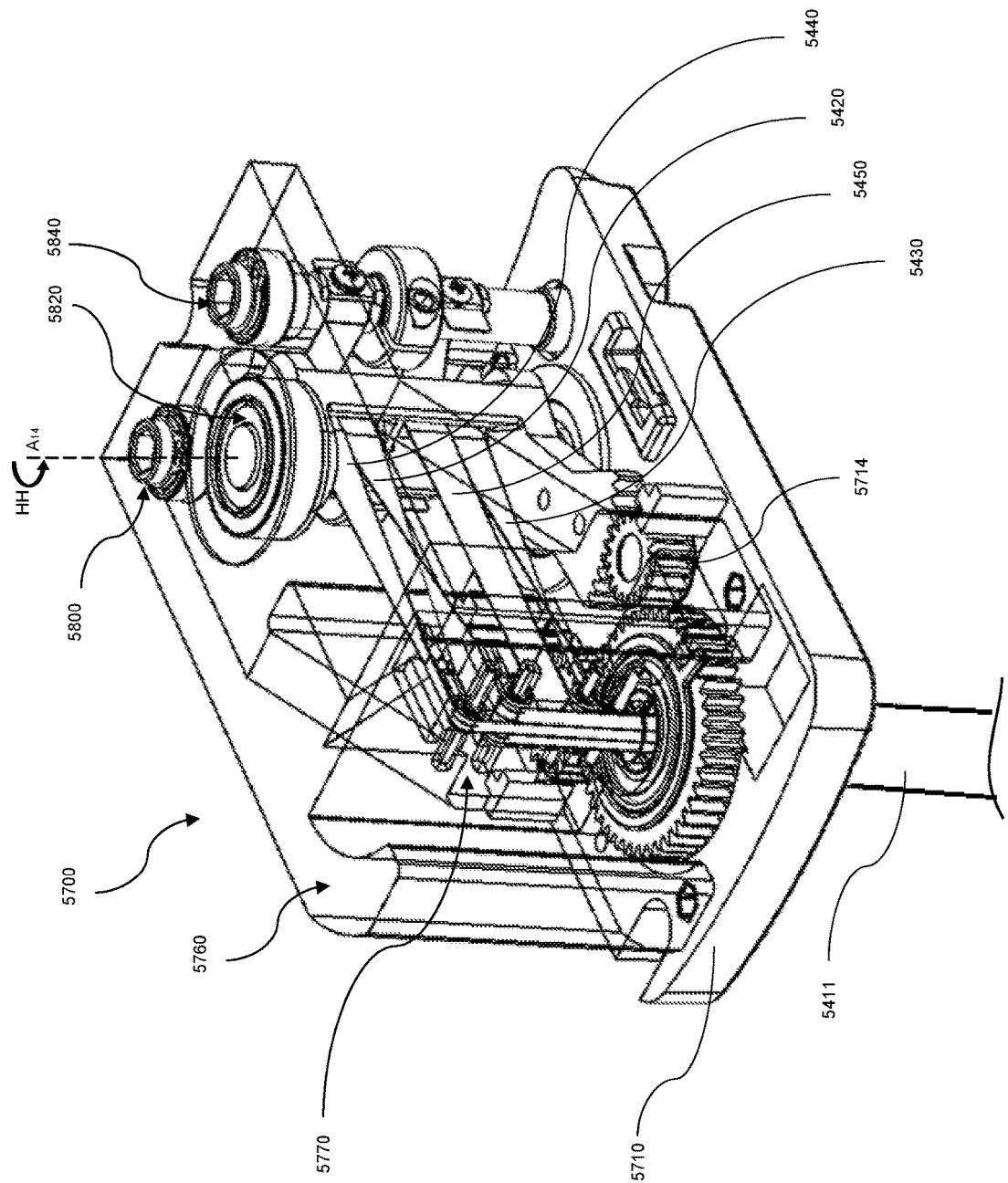
FIG. 19 is an enlarged perspective view of the actuator assembly in FIG. 18, showing a housing and guide member assembly in transparent form to detail the internal arrangement of components.
Figure 31:
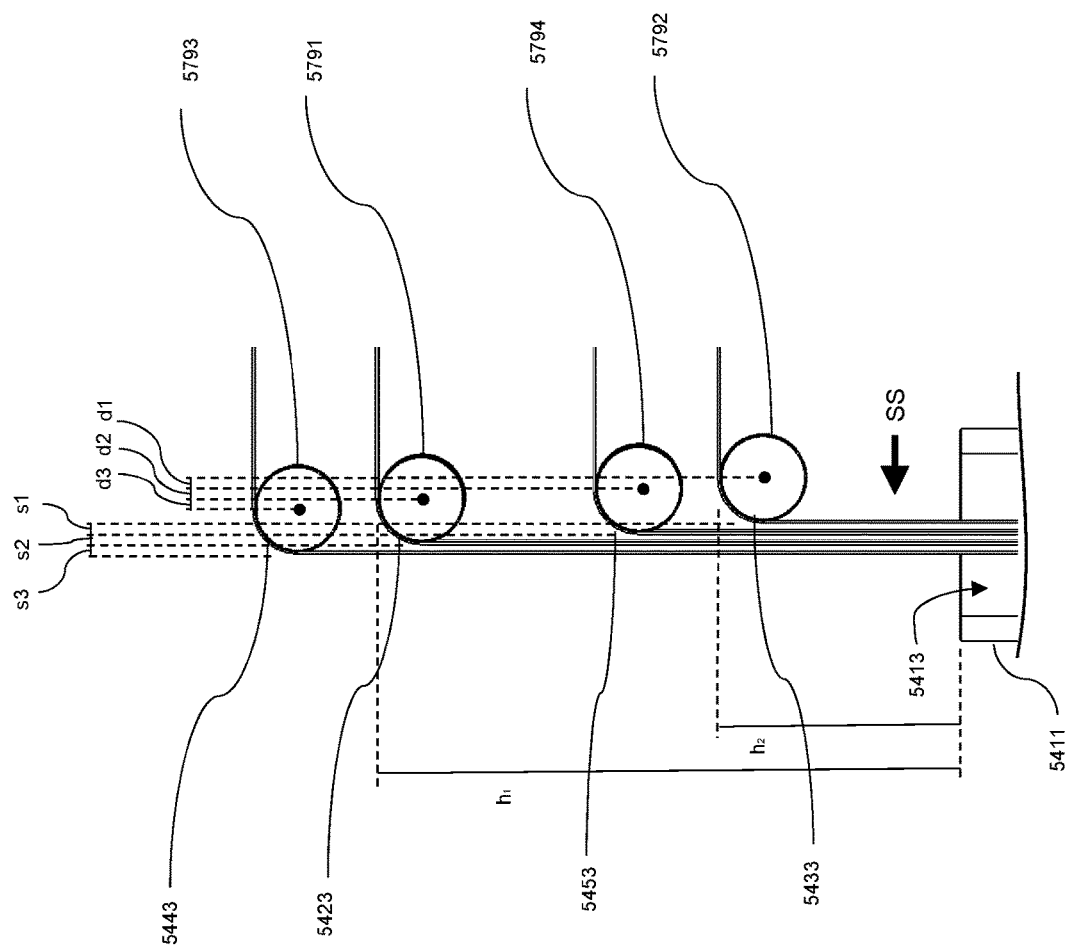
FIG. 31 is an enlarged cross-sectional view of a guide member assembly, bands, and shaft indicted by the region $Z_3$ shown in FIG. 23.

To reduce the amount of space taken up by the bands 5420, 5430, 5440, 5450 as they travel through the shaft 5410, the first, second, third, and fourth guide elements 5771, 5772, 5773, 5774 are radially offset from one another relative to the central axis of the shaft. In this manner, the first, second, third, and fourth guide elements 5771, 5772, 5773, 5774 perform a funneling function, bringing the bands 5420, 5430, 5440, 5450 closer together as they enter the shaft 5410 while maintaining adequate spacing to avoid interference. As shown in FIGS. 19, 30 and 31, a central rotational axis of each of the bearings 5791, 5792, 5793, 5794 can be offset from one another in the direction of the arrow SS, the direction being perpendicular to the central axis of the shaft 5410. For example, the bearings 5792 of the second guide element 5772 can be positioned radially the furthest from the central axis of the shaft 5410. The bearings 5794 of the fourth guide element 5774 can be placed second furthest and is spaced horizontally a first offset distance d1 in the direction SS from the bearings 5793. The bearings 5791 of the first guide element 5771 can be placed third furthest and is spaced horizontally a second offset distance d2 in the direction SS from the bearings 5794. The bearings 5792 of the third guide element 5773 may be placed radially the closest to the central axis of the shaft 5410 and is spaced horizontally a third offset distance d3 in the direction SS from the bearings 5791. In this manner, the bands 5430, 5450, 5420, 5440 can be spaced by corresponding spacing distances s1, s2, s3 in the direction SS. In some embodiment, the offset distances d1, d2, d3 can be selected such that the resulting spacing distances s1, s2, s3 is 0.5 to 3 times the thickness of each corresponding band (or band laminate forming the band), the thickness taken in the direction SS. In some embodiments, the central rotational axis of each of the bearings 5791, 5792, 5793, 5794 can all be aligned horizontally in the direction SS and the diameters of the bearings 5791, 5792, 5793, 5794 varied in order to achieve the resulting spacing distances s1, s2, s3. For example, the diameter of the bearing 5792 can be larger than the diameter of the bearing 5791.

Referring again to FIGS. 29 and 30, with the first, second, third, and fourth guide elements 5771, 5772, 5773, 5774 oriented horizontally along planes parallel to the base 5710, each of the bands 5420, 5430, 5440, 5450 is twisted along its respective longitudinal center line by about 90 degrees such that the width of the bands are reoriented to be parallel with the base 5710 as they enter the guide member 5770. In this manner, the cross-sectional shape of each band is in a first orientation to produce a low area moment of inertia about a first axis (i.e., the central rotational axis $A_{14}$, the first actuator axis $A_{13}$, and the second actuator axis $A_{15}$) and is in a second orientation to produce a low area moment of inertia about a second axis (i.e., the bend axes of the guide elements). This arrangement can allow a single band to be deformed to maintain the desired flexibility about two or more different axes (e.g., to be easily deformed about the central rotational axis $A_{14}$ and the bend axis).

Figure 23:
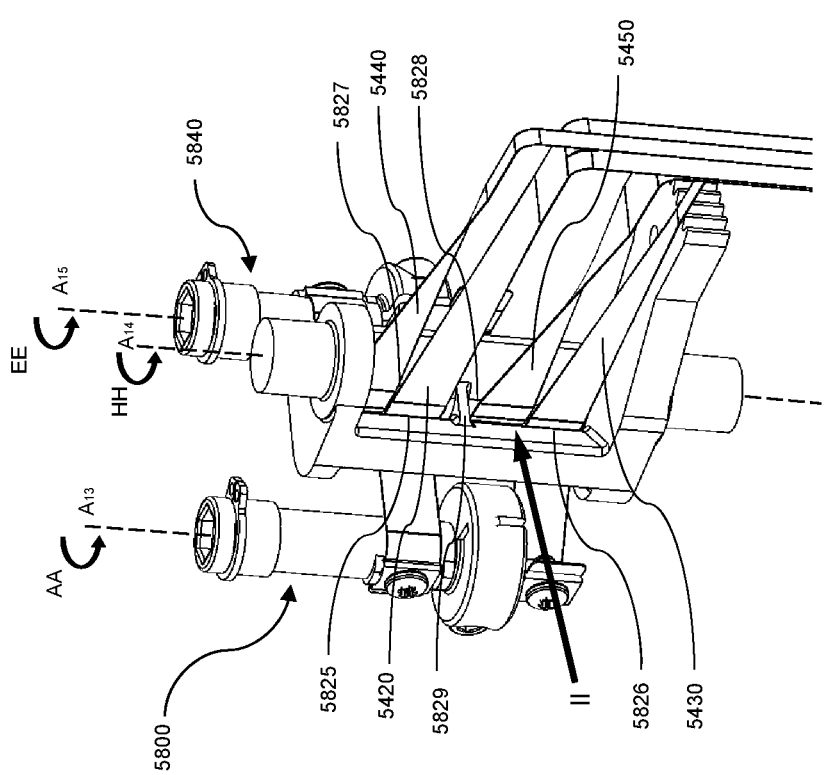

As shown in FIG. 23, the first and second bands 5420, 5430 are twisted +90 degrees relative to their respective longitudinal center line, while the third and fourth bands 5440, 5450 are twisted −90 degrees relative to their respective longitudinal center line. In this manner, the bands 5420, 5430, 5440, 5450 are stacked relative to each along the central axis of the shaft 5410, as shown for example in FIGS. 30 and 31. In some embodiments, the first and second bands 5420, 5430 are twisted −90 degrees relative to their respective longitudinal center line, while the third and fourth bands 5440, 5450 are twisted +90 degrees relative to their respective longitudinal center line. In some embodiments, the angle of twist and the direction of rotation of the twist can each be individually selected for the first, second, third and fourth bands 5420, 5430, 5440, 5450 to adjust a corresponding path of the bands for further length conservation. Each of the bands 5420, 5430, 5440, 5450 is guided over and around respective bearings 5791, 5792, 5793, 5794 to make about a 90 degree turn over and above the opening at the distal end 5412 of the shaft 5410. In other words, each of the bands 5420, 5430, 5440, 5450 exit their respective bearings 5791, 5792, 5793, 5794 aligned with the lumen 5413 of the shaft 5410 and within an inner diameter of the shaft 5410.

FIGS. 32-36 are various views of an instrument 5400', according to an embodiment. Similar to the instrument 5400, as shown with reference to FIGS. 18-20, the instrument 5400' may be coupled to and operable with a MIRS system, such as the MIRS system 1000 described with reference to FIGS. 1-4 above. The instrument 5400' includes an actuator assembly 5700' (which functions as a transmission or back-end mechanism) with a housing 5760' coupled to a base 5710'. The actuator assembly 5700' is operable to actuate the first band 5420, the second band 5430, the third band 5440, the fourth band 5450, and the wrist assembly 5500 in a similar manner as described above. The actuator assembly 5700' includes a first actuator 5800', a second actuator 5820', and a third actuator 5840'. The first actuator 5800' is coupled to and operable to actuate the first band 5420 and the second band 5430 in the same manner as the first actuator 5800 described above, and the third actuator 5840' is coupled to and operable to actuate the third band 5440 and the fourth band 5450 in the same manner as the third actuator 5840 described above.

Figure 32:
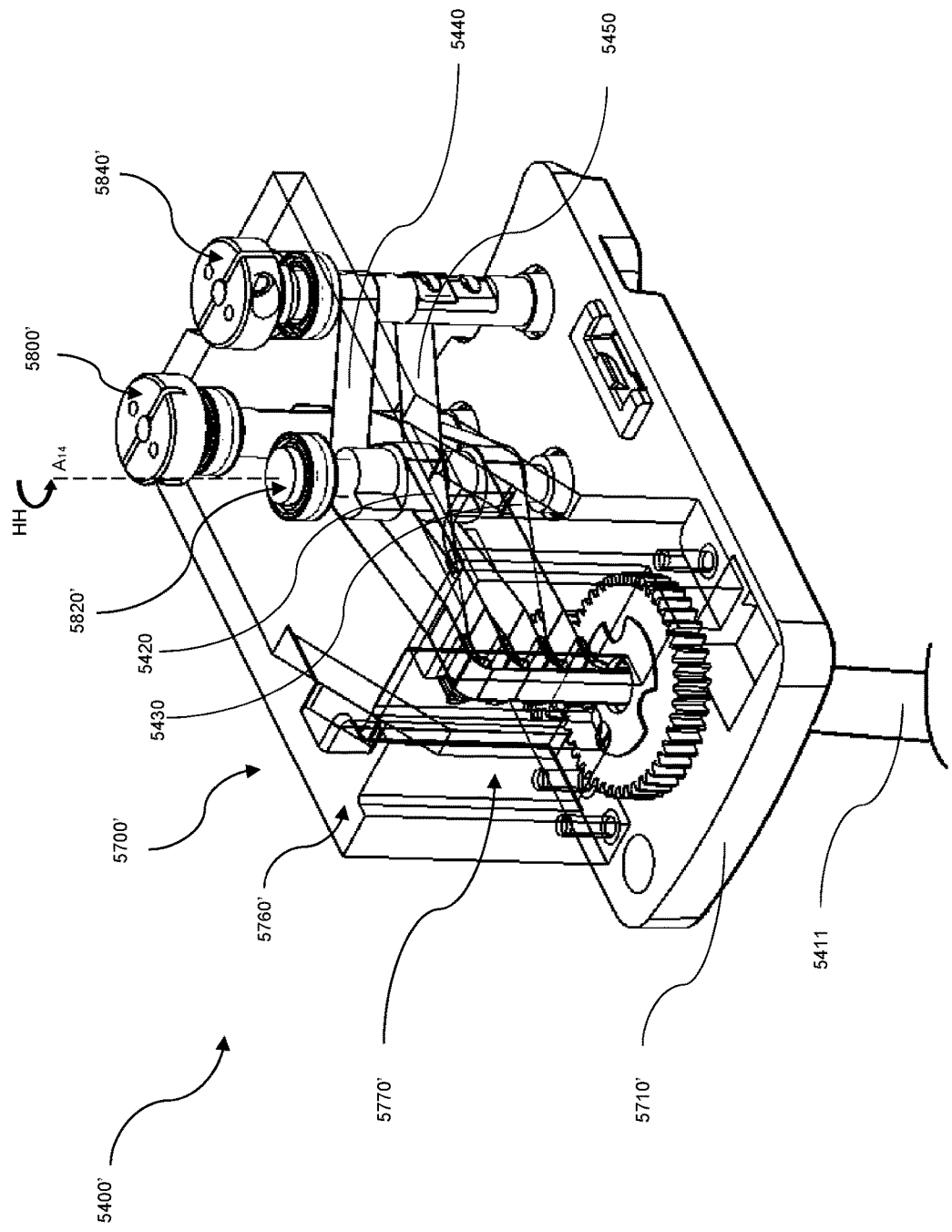
FIG. 32 is a perspective view of an actuator assembly showing a housing and guide member assembly in transparent form to detail the internal arrangement of components, according to an embodiment.
Figure 33:
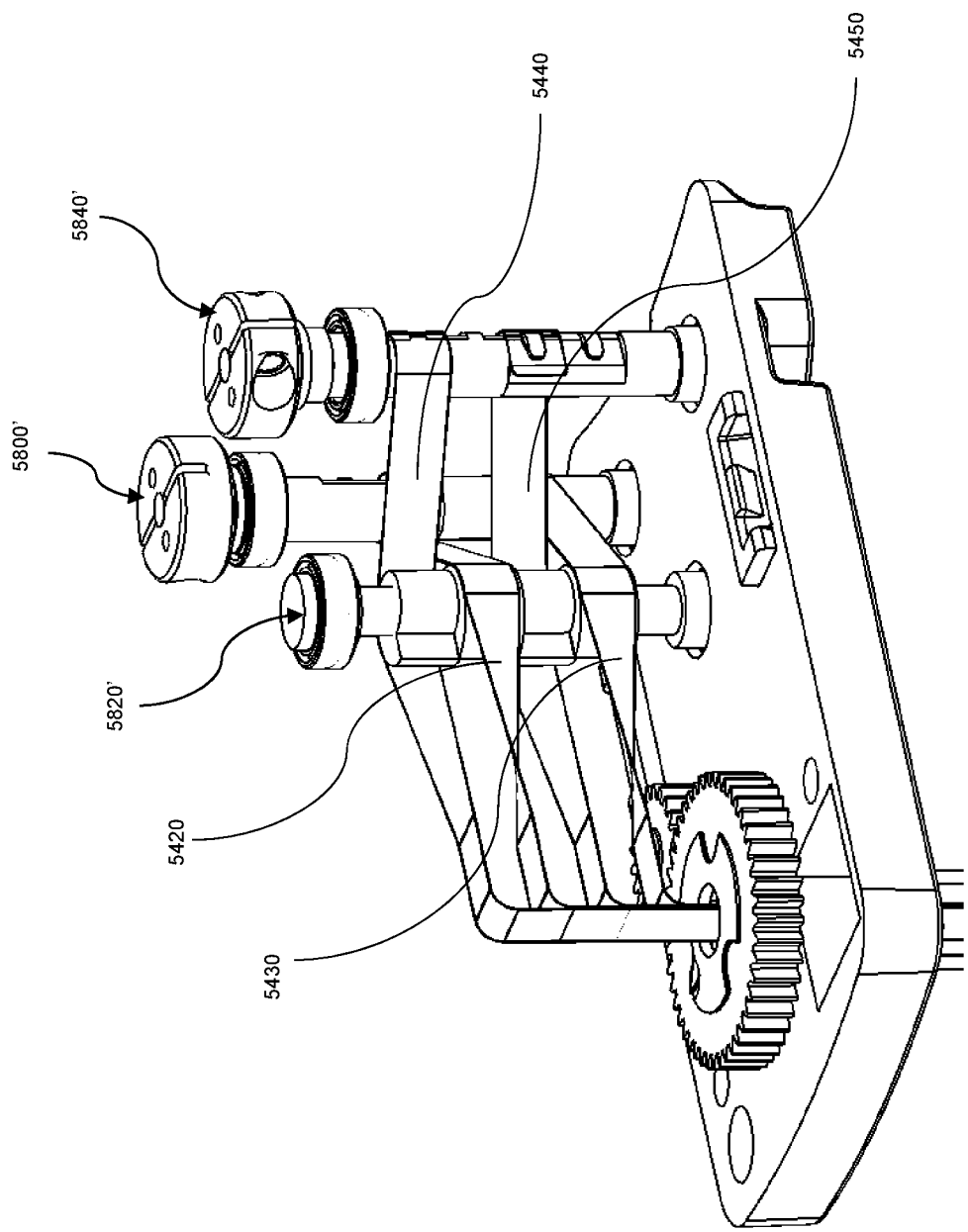
FIG. 33 is an enlarged perspective view of the actuator assembly of FIG. 32, showing the housing and guide assembly removed from the base.
Figure 34:
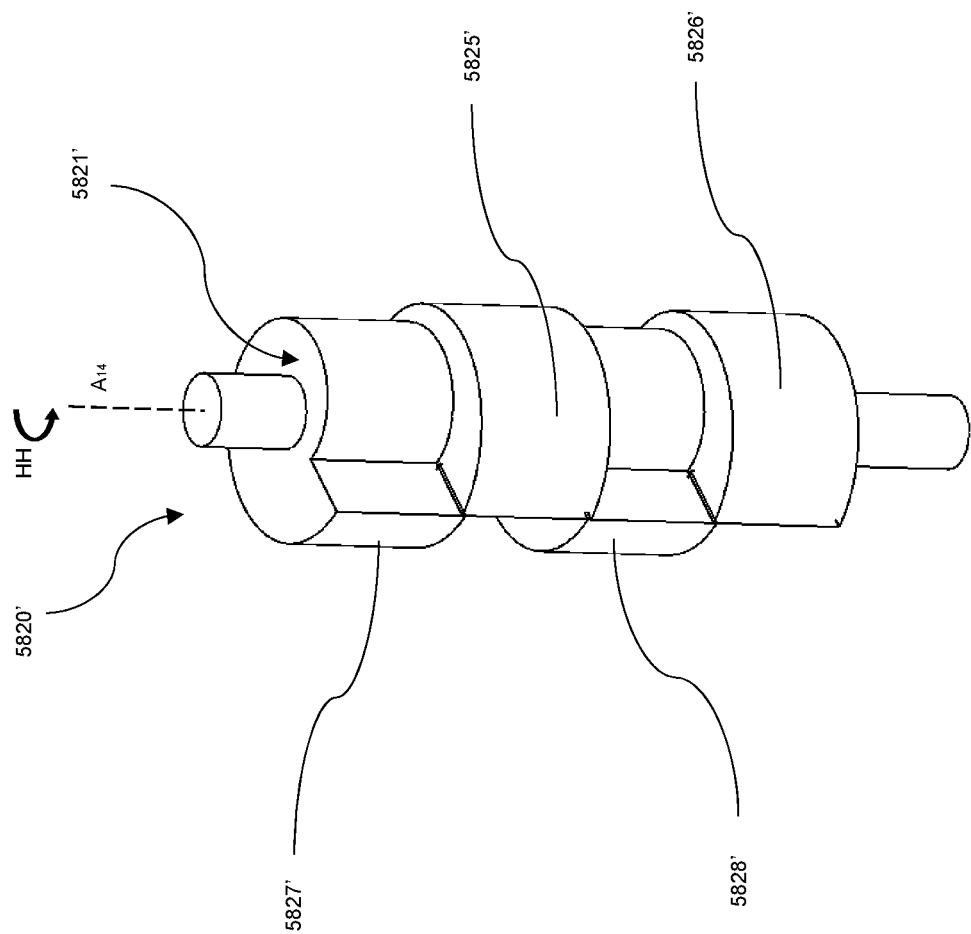
FIGS. 34, 35, and 36 are a front perspective view (FIG. 34), a side view (FIG. 35), and a top view (FIG. 36) of a second actuator of the actuator assembly in FIG. 32.
Figures 35, 36:
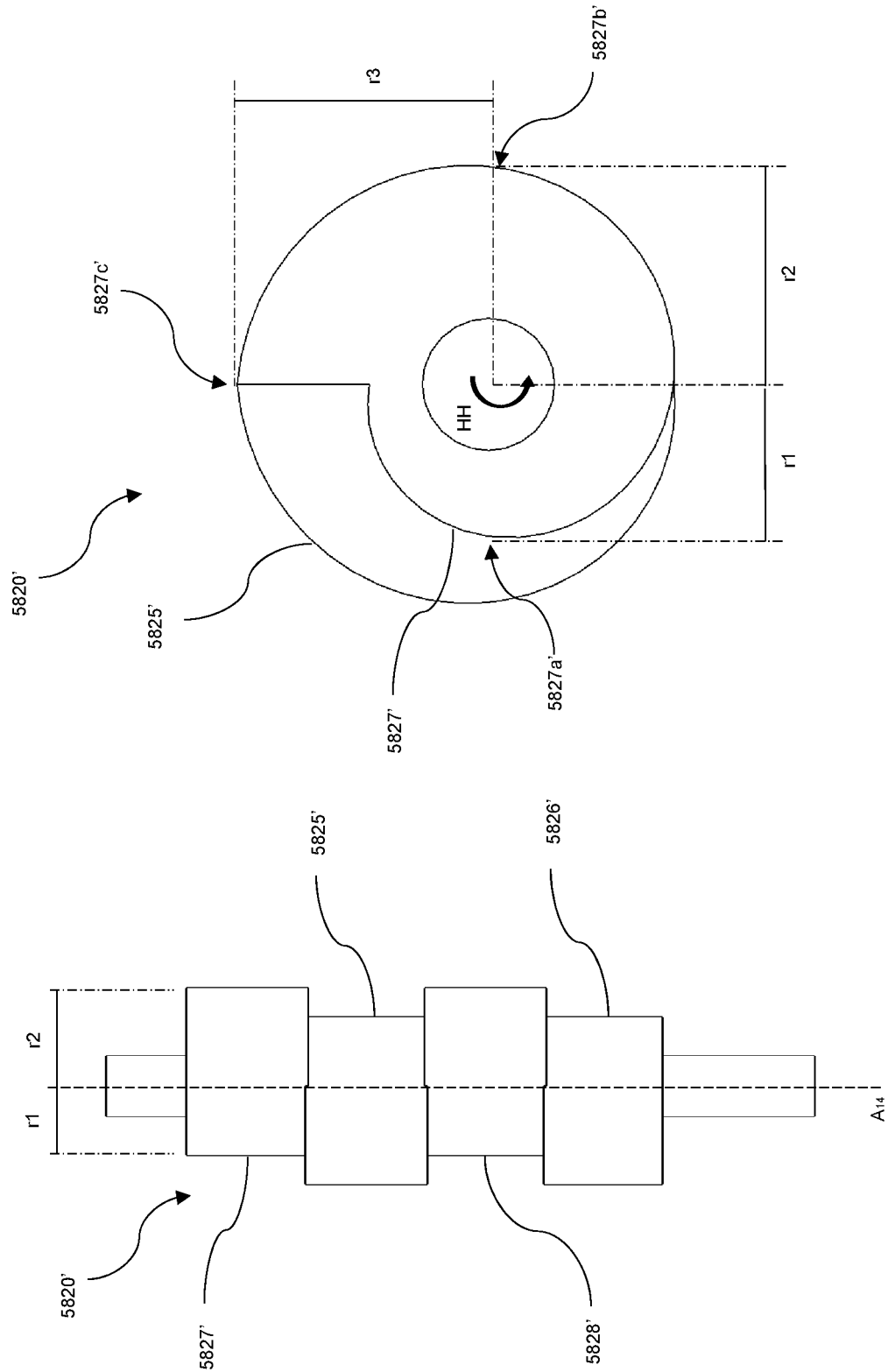

In some embodiments, the second actuator 5820' may include a guide structure 5821' with one or more curved surfaces to increase or decrease a travel path of the first, second, third, and fourth bands 5420, 5430, 5440, 5450. As shown in FIGS. 32 and 33, the bands 5420, 5430, 5440, 5450 may be routed around the guide structure 5821'. With reference to FIGS. 34-36, the guide structure 5821' of the second actuator 5820' may be aligned with the central rotational axis $A_{14}$ and include a first cam guide surface 5825', a second cam guide surface 5826', a third cam guide surface 5827', and a fourth cam guide surface 5828'. Each of the cam guide surfaces 5825', 5826', 5827', 5828' is operable to press on the bands 5420, 5430, 5440, 5450, respectively, in a direction non-parallel to the center lines of the bands 5420, 5430, 5440, 5450. The amount that each of the cam guide surfaces 5825', 5826', 5827', 5828' presses on each respective bands 5420, 5430, 5440, 5450 may be altered by rotating the second actuator 5820' about the central rotational axis $A_{14}$. The amount of deflection on the bands 5420, 5430, 5440, 5450 as a result of the pressing by a corresponding cam surface 5825', 5826', 5827', 5828' in turn increases or decreases the travel path of the bands 5420, 5430, 5440, 5450 within the actuator assembly 5700'.

As shown in FIGS. 34 and 36, each of the cam guide surfaces 5825', 5826', 5827', 5828' may have an eccentric profile defined in a plane perpendicular to and relative to the central rotational axis $A_{14}$ of the second actuator 5820'. For example, the third cam guide surface 5827' may have an outer profile spaced a variable distance away from the central rotational axis $A_{14}$. As shown in FIGS. 35 and 36, a first portion 5827a' of the third cam guide surface 5827' may be spaced a first radial distance r1 from the central rotational axis $A_{14}$, a second portion 5827b' of the third cam guide surface 5827' may be spaced a second radial distance r2, and a third portion 5827c' of the third cam guide surface 5827' may be spaced a third radial distance r3. The third radial distance r3 is greater than the second radial distance r2, and the second radial distance r2 is greater than the first radial distance r1. By way of example, if the third band 5440 initially contacts the third cam guide surface 5827' at the second portion 5827b', the third band 5440 may be further displaced (thereby increasing the travel path) by rotating the second actuator 5820' of FIG. 36 clockwise in the direction opposite of the arrow HH such that the third portion 5827c' approaches a contact point between the second actuator 5820' and the third band 5440. Conversely, displacement of the third band 5440 can be decreased (thereby reducing the travel path) by rotating the second actuator 5820' of FIG. 36 in a counter clockwise direction, in the direction of the arrow HH, such that the first portion 5827a' approaches the contact point between the second actuator 5820' and the third band 5440. In some embodiments, an entirety of one or more of the cam guide surfaces 5825', 5826', 5827', 5828' may be offset from the axis $A_{14}$ such that the axis $A_{14}$ does not intersect any region bounded by the one or more of the guide surfaces 5825', 5826', 5827', 5828'.

Once the bands 5420, 5430, 5440, 5450 pass around the second actuator 5820', the bands 5420, 5430, 5440, 5450 can be routed through a guide member 5770' of the housing 5760' and through the shaft 5410 in a similar fashion as the guide member 5770 described above with reference to FIGS. 18-20, 23-24 and 28-31. Each of the bands 5420, 5430, 5440, 5450 can also be twisted along its respective longitudinal center line, between the second actuator 5820' and the guide member 5770', in various configurations as described above with reference to FIGS. 23, 29, and 30.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, tension members, or components described herein can be constructed from multiple pieces that are later joined together. For example, in some embodiments, a link can be constructed by joining together separately constructed components. In other embodiments however, any of the links, tool members, tension members, or components described herein can be monolithically constructed.

Although the instruments are generally shown as having a second axis of rotation $A_2$ that is normal to the first axis of rotation $A_1$, in other embodiments any of the instruments described herein can include a second axis of rotation $A_2$ that is offset from the first axis of rotation $A_1$ by any suitable angle.

Although the first band 5420 is described as being separate from the second band 5430, in some embodiments, the first band 5420 and the second band 5430 can be monolithically constructed such that their respective distal end portions are a single body that is wrapped about the pulley portion 5467 of the first tool member 5462.

Any of the bands described herein can have any suitable shape. For example, in some embodiments, the bands described herein can have a rectangular cross-sectional shape (taken within a cross-sectional plane normal to the longitudinal center line of the band). In other embodiments, any of the bands described herein can have a trapezoidal shape or any other suitable cross-sectional shape. Moreover, any of the bands described herein can be constructed from any suitable materials. For example, in some embodiments, any of the bands described herein can be constructed from a series of laminates that are bonded together (e.g., via an adhesive). In other embodiments, the laminates can be joined by any other suitable method. The laminates can be constructed from any suitable material, including tungsten, steel, or any suitable polymer. Because the bands includes a width that provides a larger contact patch than a comparable cable or wire, and therefore provide a better load distribution, the surfaces that the bands contact with may be a fixed surface, a fixed surface with a friction-reducing surface coating, a rotatable surface (such as a pulley or bearing), or a rotatable with a friction-reducing surface coating. Additionally, any of the bands can be substituted with or usable together with other types of tension members, including but not limited to, cables, wires, beams, rods, or a combination of one or more of bands, cables, wires, beams or rods.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
a shaft of a medical instrument, the shaft comprising a proximal end and a distal end;
an end effector coupled to the distal end of the shaft;
a housing coupled to the proximal end of the shaft;
a first actuator rotatably supported in the housing;
a second actuator rotatably supported in the housing;
a first tension member comprising a first end portion and a second end portion, the first end portion of the first tension member being coupled to the first actuator, the second end portion of the first tension member being coupled to the end effector;
a second tension member comprising a first end portion and a second end portion, the first end portion of the second tension member being coupled to the first actuator, the second end portion of the second tension member being coupled to the end effector, the first actuator is configured to move the first tension member in a first direction and the second tension member in a second direction, opposite to the first direction, to actuate the end effector in a first degree of freedom;
the second actuator comprising a first guide structure, the first guide structure comprising a first guide surface and a second guide surface, the first guide surface being in contact with the first end portion of the first tension member, the second guide surface being in contact with the first end portion of the second tension member; and
movement of the second actuator actuates both the first tension member and the second tension member in the first direction to actuate the end effector in a second degree of freedom.

2. The apparatus of claim 1, wherein:
the first guide surface is a curved surface monolithically constructed with the second actuator, and the first end portion of the first tension member slides along the first guide surface when the first actuator moves the first tension member; and
the second guide surface is a curved surface monolithically constructed with the second actuator, and the first end portion of the second tension member slides along the second guide surface when the first actuator moves the second tension member.

3. The apparatus of claim 2, wherein:
the first guide surface is curved about a guide structure axis of the second actuator, and the first guide surface is a first width of the second actuator extending along the guide structure axis; and
the second guide surface is curved about the guide structure axis of the second actuator, and the second guide surface is a second width of the second actuator extending along the guide structure axis.

4. The apparatus of claim 1, further comprising:
a third actuator rotatably supported in the housing;
a third tension member comprising a first end portion and a second end portion;
a fourth tension member comprising a first end portion and a second end portion;
the end effector comprises a first jaw member and a second jaw member;
the second end portion of the first tension member and the second end portion of the second tension member are coupled to the first jaw member of the end effector;
the first end portion of the third tension member being coupled to the third actuator, the second end portion of the third tension member being coupled to the second jaw member of the end effector;
the first end portion of the fourth tension member being coupled to the third actuator, the second end portion of the fourth tension member being coupled to the second jaw member of the end effector;
movement of the third actuator actuates the third tension member in the first direction and the fourth tension member in the second direction to actuate the second jaw member of the end effector;
the second actuator comprises a second guide structure comprising a third guide surface and a fourth guide surface, the third guide surface being in contact with the first end portion of the third tension member, the fourth guide surface being in contact with the first end portion of the fourth tension member; and
movement of the second actuator actuates the third tension member and the fourth tension member in the second direction to actuate the end effector in the second degree of freedom.

5. The apparatus of claim 4, wherein:
the second actuator defines a central rotational axis, a first guide structure axis parallel to the central rotational axis, and a second guide structure axis parallel to the central rotational axis;
the first guide surface is curved about the first guide structure axis of the second actuator, and the first guide surface is a first width of the second actuator extending along the first guide structure axis;
the second guide surface is curved about the first guide structure axis of the second actuator, and the second guide surface is a second width of the second actuator along the first guide structure axis;
the third guide surface is curved about the second guide structure axis of the second actuator, and the third guide surface is a third width of the second actuator extending along the second guide structure axis; and
the fourth guide surface is curved about the second guide structure axis of the second actuator, and the fourth guide surface is a fourth width of the second actuator extending along the second guide structure axis.

6. The apparatus of claim 4, wherein the second actuator comprises a bridge portion, the bridge portion extending from a first location between the first guide surface and the second guide surface to a second location between the third guide surface and the fourth guide surface.

7. The apparatus of claim 1, wherein:
the apparatus further comprises a guide member coupled to the housing, the guide member comprising a first guide groove and a second guide groove;

the shaft of the medical instrument defines a lumen extending along a central axis of the shaft from the proximal end to the distal end of the shaft;

at least a portion of the guide member extends over the lumen of the shaft at the proximal end of the shaft;

a central portion of the first tension member being routed within the first guide groove and into the lumen of the shaft;

a central portion of the second tension member is routed within the second guide groove and into the lumen of the shaft; and the first guide groove is at a first distance from the proximal end of the shaft along the central axis of the shaft, the second guide groove is at a second distance from the proximal end of the shaft along the central axis of the shaft, and the first distance is different from the second distance.

8. The apparatus of claim 1, wherein a surface of the first actuator comprises a hook portion, and the first end portion of the first tension member is coupled to the first actuator via the hook portion.

9. The apparatus of claim 1, wherein:

the apparatus further comprises a guide member coupled to the housing;

the shaft of the medical instrument defines a lumen extending along a central axis of the shaft from the proximal end to the distal end of the shaft; and the guide member extends over the lumen of the shaft at the proximal end of the shaft, the guide member comprising a first guide element and a second guide element, a central portion of the first tension member being routed over the first guide element and into the lumen of the shaft, a central portion of the second tension member being routed over the second guide element and into the lumen of the shaft, the first guide element being at a first offset distance from the proximal end of the shaft along the central axis of the shaft, the second guide element being at a second offset distance from the proximal end of the shaft along the central axis of the shaft, and the first offset distance being different from the second offset distance.

10. The apparatus of claim 9, wherein:

the first guide element comprises a first rod and a first bearing, the first bearing being configured to rotate about the first rod when the first tension member moves; and the second guide element comprises a second rod and a second bearing, the second bearing being configured to rotate about the second rod when the second tension member moves.

11. The apparatus of claim 10, wherein:

the first bearing and the second bearing are configured to rotate in opposite directions when the first actuator moves the first tension member in the first direction and the second tension member in the second direction; and the first bearing and the second bearing are configured to rotate in a same direction when the second actuator moves the first tension member and the second tension member in the first direction.

12. The apparatus of claim 9, wherein:

the first guide element is perpendicularly offset from the central axis of the shaft by the first offset distance;

the second guide element is perpendicularly offset from the central axis of the shaft by the second offset distance.

* * * * *